(12) United States Patent
Olson et al.

(10) Patent No.: US 7,060,273 B2
(45) Date of Patent: *Jun. 13, 2006

(54) METHODS FOR INHIBITING HIV-1 INFECTION

(75) Inventors: William C. Olson, Ossining, NY (US); Paul J. Maddon, Scarsdale, NY (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 228 days.

This patent is subject to a terminal disclaimer.

(21) Appl. No.: 10/116,797

(22) Filed: Apr. 5, 2002

(65) Prior Publication Data

US 2003/0044411 A1 Mar. 6, 2003

Related U.S. Application Data

(60) Provisional application No. 60/282,380, filed on Apr. 6, 2001.

(51) Int. Cl.
A61K 39/42 (2006.01)

(52) U.S. Cl. ............... 424/148.1; 424/154.1; 424/139.1

(58) Field of Classification Search ............ 424/148.1, 424/154.1, 139.1
See application file for complete search history.

(56) References Cited

U.S. PATENT DOCUMENTS

| | | | |
|---|---|---|---|
| 6,107,019 | A | 8/2000 | Allaway et al. |
| 6,344,545 | B1 | 2/2002 | Allaway et al. |
| 6,548,636 | B1 | 4/2003 | Dragic et al. |
| 2002/0106374 | A1 | 8/2002 | Olson et al. |
| 2002/0146415 | A1 | 10/2002 | Olson et al. |
| 2003/0092632 | A1 | 5/2003 | Dragic et al. |
| 2003/0228306 | A1 | 12/2003 | Olson et al. |

FOREIGN PATENT DOCUMENTS

| | | |
|---|---|---|
| WO | 9641020 | 12/1996 |
| WO | 9726009 | 7/1997 |
| WO | 9737005 | 10/1997 |
| WO | 9747319 | 12/1997 |
| WO | 9856421 | 12/1998 |
| WO | 0035409 | 6/2000 |
| WO | WO0035409 | 6/2000 |
| WO | 0164710 | 9/2001 |
| WO | 0222077 | 3/2002 |
| WO | 02068608 | 9/2002 |
| WO | 02083172 | 10/2002 |
| WO | 03072766 | 9/2003 |

OTHER PUBLICATIONS

Grene, et al. Anti–CCR5 antibodies in sera of HIV–positive individuals. Human Immunology, vol. 62, No. 2 (Feb. 2001), pp 143–5 (Exhibit B).

Trkola, et al. Potent, broad–spectrum inhibition of human immunodeficiency virus type 1 by the CCR5 monoclonal antibody PRO 140. Journal of Virology, vol. 75, No. 2 (Jan. 2001), pp. 579–588 (Exhibit C).

(Continued)

*Primary Examiner*—J. S. Parkin
(74) *Attorney, Agent, or Firm*—John P. White, Esq.; Cooper & Dunham LLP

(57) ABSTRACT

This invention provides a method of reducing an HIV infected subject's HIV-1 viral load which comprises administering to the subject an effective viral load reducing amount of an antibody which (a) binds to a CCR5 chemokine receptor and (b) inhibits fusion of HIV-1 to a CD4+CCR5+cell, so as to thereby reduce the subject's HIV-1 viral load to 50% or less of the subject's HIV-1 viral load prior to administering the antibody to the subject.

24 Claims, 22 Drawing Sheets

OTHER PUBLICATIONS

Ditzel, et al. The CCR5 receptor acts as an alloantigen in CCR5Delta32 homozygous individuals: identification of chemokine and HIV–1 blocking human anitbodies. Proceedings of the National Academy of Sciences of the United States of America, vol. 95, No. 9 (Apr. 28, 1998), pp. 5241–5245 (Exhibit D).

Vila–Coro, et al. HIV–1 infection through the CCR5 receptor is blocked by receptor di–merization. Proceedings of the National Academy of Sciences of the United States of America, vol. 97, No. 7 (Mar. 28, 2000), pp. 3388–3393 (Exhibit F).

Olson, et al. Differential inhibition of human immunodeficiency virus type 1 fusion, gp120 binding, and CC–chemokine activity by monoclonal antibodies to CCR5. Journal of Virology, vol. 73, No. 5 (May 1999), pp. 4145–4155 (Exhibit G).

U.S. Appl. No. 08/663,616, filed Jun. 14, 1996, Allaway et al.

U.S. Appl. No. 60/019,715, filed Jun. 14, 1996, Allaway et al.

U.S. Appl. No. 08/673,682, filed Jun. 25, 1996, Allaway et al.

U.S. Appl. No. 08/665,090, filed Jun. 14, 1996, Allaway et al.

U.S. Appl. No. 60/019,941, filed Jun. 14, 1996, Allaway et al.

U.S. Appl. No. 08/874,570, filed Jun. 13, 1997, Allaway et al.

U.S. Appl. No. 08/874.618, filed Jun. 13, 1997, Allaway et al.

U.S. Appl. No. 09/724,105, filed Nov. 28, 2000, Allaway et al.

U.S. Appl. No. 09/852,238, filed May 9, 2001, Allaway et al.

U.S. Appl. No. 09/212,793, filed Dec. 16, 1998, Olson et al.

U.S. Appl. No. 60/112,532, filed Dec. 16, 1998, Olson et al.

U.S. Appl. No. 09/464,902, filed Dec. 16, 1999, Olson et al.

U.S. Appl. No. 09/594,983, filed Jun. 15, 2000, Olson et al.

U.S. Appl. No. 09/663,219, filed Sep. 15, 2000, Olson et al.

U.S. Appl. No. 60/266,738, filed Feb. 6, 2001, Olson et al.

U.S. Appl. No. 60/282,380, filed Apr. 6, 2001, Olson et al.

U.S. Appl. No. 09/888,938, filed Jun. 25, 2001, Allaway et al.

U.S. Appl. No. 10/323,314, filed Dec. 19, 2002, Dragic et al.

U.S. Appl. No. 08/627,684, filed Apr. 2, 1996, Allaway et al.

U.S. Appl. No. 60/014,532, filed Apr. 2, 1996, Allaway et al.

Gauduin MC, Parren PW, Weir R, Barbas CF, Burton DR and Koup RA (1997) Passive immunization with a human monoclonal antibody protects hu–PBL–SCID mice against challenge by primary isolates of HIV–1, Nature Medicine 3: 1389–1393; and.

Poignard P, Sabbe R, Picchio GR, Wang M, Gulizia RJ, Katinger H, Parren PW, Mosier DE and Burton DR (1999) Neutralizing antibodies have limited effects on the control of established HIV–1 infection in vivo, Immunity 10: 431–438.

U.S. Appl. No. 10/081,128, filed Feb. 22, 2002, Olson et al.

U.S. Appl. No. 60/358,886, filed Feb. 22, 2002, Olson et al.

U.S. Appl. No. 10/763,545, filed Jan. 23, 2004, Olson et al.

U.S. Appl. No. 09/460,216, filed Dec. 13, 1999, Allaway et al.

FIGURE 1

| mAb | Mean Fluorescence Intensity | | % Gated | |
|---|---|---|---|---|
| | L1.2-CCR5 | PBMC | L1.2-CCR5 | PBMC |
| mouse IgG1 | 10 | 4 | 1 | 1 |
| 2D7 | 75 | 29 | 92 | 36 |
| PA8 | 48 | 9 | 73 | 3 |
| PA9 | 79 | 5 | 96 | 3 |
| PA10 | 80 | 8 | 96 | 5 |
| PA11 | 107 | 8 | 96 | 10 |
| PA12 | 115 | 8 | 96 | 8 |
| PA14 | 81 | 14 | 96 | 22 |

FIGURE 2

| INHIBITOR COMBINATION | CONCENTRATION RATIO | ASSAY | COMBINATION INDEX | |
|---|---|---|---|---|
| | | | 90% Inhibition | 50% Inhibition |
| PA12:2D7 | 10:1 | Entry | 0.043 | 0.291 |
| | 2:1 | Fusion | 0.017 | 0.019 |
| | 10:1 | Fusion | 0.087 | 0.067 |
| | 50:1 | Fusion | 0.158 | 0.046 |
| PA14:PA14 | 10:1 | Entry | 0.437 | 0.535 |
| | 10:1 | Fusion | 0.22 | 0.263 |
| PA14:2D7 | 1:1 | Entry | 2.85 | 1.85 |
| | 1:1 | Fusion | 1.34 | 1.74 |
| PA12:PA11 | 1:1 | Entry | 0.707 | 0.641 |
| PA12:RANTES | 1000:1 | Fusion | 0.331 | 0.156 |
| PA14:RANTES | 100:1 | Fusion | 1.6 | 1.37 |
| 2D7:RANTES | 100:1 | Fusion | 0.972 | 0.962 |
| PA12:CD4-IgG2 | 10:1 | Fusion | 0.3 | 0.31 |
| PA14:CD4-IgG2 | 1:1 | Fusion | 0.957 | 0.566 |
| 2D7:CD4-IgG2 | 1:1 | Fusion | 1.127 | 0.302 |

FIGURE 3

| | | IC$_{50}$ values (µg/ml) | | |
|---|---|---|---|---|
| Epitopes | cell-cell fusion inhibition | viral entry inhibition | gp120-binding inhibition | calcium flux inhibition |
| PA8 | Nt | - | - | - | - |
| PA9 | Nt/ECL2 | - | - | 0.24 | - |
| PA10 | Nt/ECL2 | - | - | 0.13 | - |
| PA11 | Nt | 25.5 | - | 0.33 | - |
| PA12 | Nt | 10.0 | - | 0.24 | - |
| PA14 | Nt/ECL2 | 1.7 | .024 | 1.58 | 6.4 |
| 2D7 | ECL2 | 1.6 | .026 | 1.38 | 45 |

FIGURE 9

|  | Combination Index | | | |
| --- | --- | --- | --- | --- |
|  | CD4-IgG2:T-20 Mass Ratio | | | |
| Percent Inhibition | 25:1 (low) | 25:1 (high) | 5:1 | 1:1 |
| 95 | 0.32 | 0.20 | 0.22 | 0.50 |
| 90 | 0.38 | 0.25 | 0.27 | 0.55 |
| 85 | 0.43 | 0.29 | 0.30 | 0.59 |
| 80 | 0.47 | 0.33 | 0.34 | 0.62 |
| 75 | 0.51 | 0.36 | 0.37 | 0.65 |
| 70 | 0.54 | 0.39 | 0.40 | 0.67 |
| 65 | 0.58 | 0.42 | 0.43 | 0.70 |
| 60 | 0.61 | 0.45 | 0.45 | 0.73 |
| 55 | 0.65 | 0.48 | 0.49 | 0.75 |
| 50 | 0.69 | 0.51 | 0.52 | 0.78 |

FIGURE 10

| Percent Inhibition | T-20 | | | CD4-IgG2 | | |
|---|---|---|---|---|---|---|
| | Concentration, µg/ml | | Dose Reduction | Concentration, µg/ml | | Dose Reduction |
| | Alone | Combination | | Alone | Combination | |
| 99 | 1.1 | 0.17 | 6.6 | 130 | 4.3 | 29 |
| 95 | 0.21 | 0.044 | 4.9 | 19 | 1.10 | 17 |
| 90 | 0.10 | 0.024 | 4.2 | 7.8 | 0.59 | 13 |
| 70 | 0.025 | 0.0076 | 3.3 | 1.6 | 0.19 | 8.4 |
| 50 | 0.011 | 0.0039 | 2.8 | 0.60 | 0.095 | 6.3 |

FIGURE 11A

| Percent Inhibition | Combination Index | PRO 542 Concentration, nM Alone | PRO 542 Concentration, nM Mix | PRO 542 Dose Reduction | PA12 Concentration, nM Alone | PA12 Concentration, nM Mix | PA12 Dose Reduction | T-20 Concentration, nM Alone | T-20 Concentration, nM Mix | T-20 Dose Reduction |
|---|---|---|---|---|---|---|---|---|---|---|
| 95 | 0.41 | 10 | 2.1 | 4.8 | 730 | 2.8 | 260 | 94 | 19 | 4.9 |
| 90 | 0.45 | 7.0 | 1.6 | 4.4 | 320 | 2.1 | 150 | 63 | 14 | 4.5 |
| 70 | 0.47 | 4.1 | 0.92 | 4.5 | 72 | 1.2 | 60 | 30 | 8.1 | 3.7 |
| 50 | 0.48 | 3.1 | 0.66 | 4.7 | 28 | 0.87 | 32 | 19 | 5.8 | 3.3 |

PRO 542, PA12 and T-20 were used in an approximate 1:1:10 molar concentration ratio.

FIGURE 11B

| Percent Inhibition | Combination Index | PRO 542 Concentration, nM Alone | PRO 542 Concentration, nM Mix | PRO 542 Dose Reduction | PRO 140 Concentration, nM Alone | PRO 140 Concentration, nM Mix | PRO 140 Dose Reduction | T-20 Concentration, nM Alone | T-20 Concentration, nM Mix | T-20 Dose Reduction |
|---|---|---|---|---|---|---|---|---|---|---|
| 95 | 0.40 | 8.5 | 1.9 | 4.5 | 19 | 1.0 | 19 | 140 | 17 | 8.2 |
| 90 | 0.39 | 7.1 | 1.5 | 4.7 | 13 | 0.77 | 17 | 100 | 13 | 7.7 |
| 70 | 0.37 | 5.3 | 0.87 | 6.1 | 7.2 | 0.46 | 16 | 57 | 7.7 | 7.4 |
| 50 | 0.35 | 4.6 | 0.63 | 7.3 | 4.9 | 0.34 | 14 | 40 | 5.6 | 7.1 |

PRO 542, PRO 140 and T-20 were used in an approximate 2:1:20 molar concentration ratio.

FIGURE 11C

| Percent Inhibition | Combination Index | PRO 542 Concentration, nM Alone | PRO 542 Concentration, nM Mix | PRO 542 Dose Reduction | PRO 140 Concentration, nM Alone | PRO 140 Concentration, nM Mix | PRO 140 Dose Reduction | T-20 Concentration, nM Alone | T-20 Concentration, nM Mix | T-20 Dose Reduction |
|---|---|---|---|---|---|---|---|---|---|---|
| 95 | 0.24 | 61 | 2.5 | 24 | 11.9 | 0.72 | 17 | 156 | 22 | 7.1 |
| 90 | 0.22 | 32 | 1.4 | 23 | 8.4 | 0.40 | 21 | 96 | 13 | 7.4 |
| 70 | 0.19 | 9.8 | 0.50 | 20 | 4.5 | 0.14 | 32 | 40 | 4.5 | 8.9 |
| 50 | 0.18 | 4.7 | 0.26 | 18 | 3.0 | 0.074 | 41 | 23 | 2.3 | 10 |

PRO 542, PRO 140 and T-20 were used in an approximate 4:1:30 molar concentration ratio.

FIGURE 11D

| Percent Inhibition | Combination Index | PRO 140 | | | | T-20 | | | |
|---|---|---|---|---|---|---|---|---|---|
| | | Concentration, nM | | | Dose Reduction | Concentration, nM | | | Dose Reduction |
| | | Alone | Mix | | | Alone | Mix | | |
| 95 | 0.56 | 12 | 1.8 | | 6.7 | 156 | 55 | | 2.8 |
| 90 | 0.55 | 8.4 | 1.1 | | 7.4 | 96 | 35 | | 2.7 |
| 70 | 0.55 | 4.5 | 0.51 | | 8.8 | 40 | 16 | | 2.5 |
| 50 | 0.56 | 3.0 | 0.31 | | 9.9 | 23 | 10 | | 2.4 |

PRO 140 and T-20 were used in an approximate 1:30 molar concentration ratio.

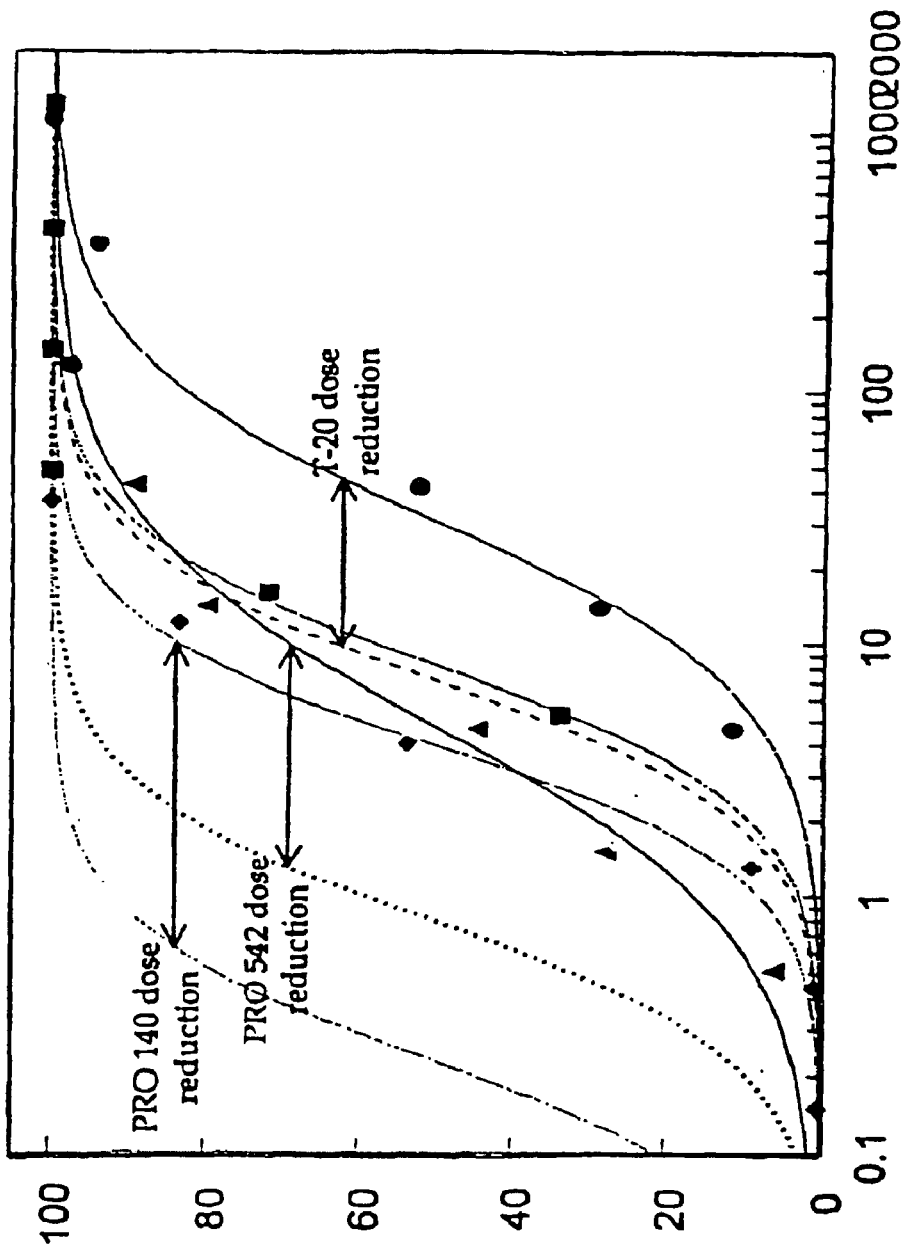
FIGURE 12 *Triple Combination Synergistically Blocks HIV-1 Entry (I)*

US 7,060,273 B2

METHODS FOR INHIBITING HIV-1 INFECTION

This application claims the benefit of Provisional application Ser. No. 60/282,380, filed Apr. 6, 2001.

Throughout this application, various publications are referenced by Arabic numerals. Full citations for these publications may be found at the end of the specification immediately preceding the claims. The disclosure of these publications is hereby incorporated by reference into this application to describe more fully the art to which this invention pertains.

BACKGROUND OF THE INVENTION

Human immunodeficiency virus type 1 (HIV-1) induces viral-to-cell membrane fusion to gain entry into target cells (8, 15, 66). The first high-affinity interaction between the virion and the cell surface is the binding of the viral surface glycoprotein gp120 to the CD4 antigen (13, 30, 41, 42). This in turn induces conformational changes in gp120, which enable it to interact with one of several chemokine receptors (4, 5, 21, 36). The CC-chemokine receptor CCR5 is the major co-receptor for macrophage-tropic (R5) strains, and plays a crucial role in the sexual transmission of HIV-1 (4, 5, 21, 36). T cell line-tropic (X4) viruses use CXCR4 to enter target cells, and usually, but not always, emerge late in disease progression or as a consequence of virus propagation in tissue culture (4, 5, 21, 36). Some primary HIV-1 isolates are dual-tropic (R5X4) since they can use both co-receptors, though not always with the same efficiency (11, 57). Mutagenesis studies coupled with the resolution of the gp120 core crystal structure demonstrated that the co-receptor-binding site on gp120 comprises several conserved residues (32, 53, 65).

It has been demonstrated that tyrosines and negatively charged residues in the amino-terminal domain (Nt) of CCR5 are essential for gp120 binding to the co-receptor, and for HIV-1 fusion and entry (6, 18, 20, 22, 28, 31, 52, 54). Residues in the extracellular loops (ECL) 1-3 of CCR5 were dispensable for co-receptor function, yet the CCR5 inter-domain configuration had to be maintained for optimal viral fusion and entry (24). This led to the conclusion either that gp120 forms interactions with a diffuse surface on the ECLs, or that the Nt is maintained in a functional conformation by bonds with residues in the ECLs. Studies with chimeric co-receptors and anti-CCR5 monoclonal antibodies have also shown the importance of the extracellular loops for viral entry (5, 54, 64).

Molecules that specifically bind to CCR5 and CXCR4 and block interactions with their ligands are a powerful tool to further probe the structure/function relationships of the co-receptors. Characterizing such compounds could also assist in designing effective therapeutic agents that target co-receptor-mediated steps of viral entry. Inhibitors of CCR5 or CXCR4 co-receptor function identified to date are diverse in nature and include small molecules, peptides, chemokines and their derivatives, and monoclonal antibodies (mAbs). The mechanisms of action of the small molecules that block entry by interfering with CXCR4 co-receptor function are not well understood (17, 49, 55, 68). One such inhibitor, the anionic small molecule AMD3100, depends on residues in ECL2 and the fourth trans-membrane (TM) domain of CXCR4 to inhibit viral entry, but it is not clear whether it does so by disrupting gp120 binding to CXCR4 or post-binding steps leading to membrane fusion (16, 34, 55). To date, no small molecules have been reported that specifically block CCR5-mediated HIV-1 entry. Inhibition of HIV-1 entry by chemokines is mediated by at least two distinct mechanisms: blockage of the gp120 /co-receptor interaction and internalization of the chemokine/receptor complex (3, 26, 59, 63). The variant AOP-RANTES also inhibits recycling of CCR5 to the cell surface (40, 56). Variants such as RANTES 9-68 and Met-RANTES only prevent the gp120/CCR5 interaction and do not down-regulate CCR5 (67). SDF-1 variants presumably act through a similar mechanism to block viral entry mediated by CXCR4 (12, 27, 39). Only one anti-CXCR4 mAb, 12G5, has been characterized for its anti-viral properties. The efficiency of 12G5 inhibition of viral entry has been reported to be both cell- and isolate-dependent (43, 58). This mAb binds to the ECL2 of CXCR4, but the mechanism by which it inhibits entry is unknown (7). Few of the anti-CCR5 mabs characterized to date efficiently prevent HIV-1 entry (28, 64). Interestingly, mabs whose epitopes lie in the Nt domain of CCR5, which contains the gp120-binding site, inhibit viral fusion and entry less efficiently than mAb 2D7, whose epitope lies in ECL2. 2D7 also antagonizes CC-chemokine activity (64).

A panel of six murine mAbs, designated PA8, PA9, PA10, PA11, PA12 and PA14 have been isolated and characterized.

All six mAbs specifically bound to CCR5$^+$ cells but with different efficiencies that were cell type-dependent. Epitope mapping studies identified the residues that are important for mAb binding and also revealed information about the folding and interactions of the CCR5 extracellular domains. All mabs inhibited HIV-1 fusion and entry, but there was no correlation between the ability of a mAb to inhibit fusion and entry and its ability to inhibit binding of gp120/sCD4 to CCR5$^+$ cells.

SUMMARY OF THE INVENTION

This invention provides a method of reducing an HIV infected subject's HIV-1 viral load which comprises administering to the subject an effective viral load reducing amount of an antibody which (a) binds to a CCR5 chemokine receptor and (b) inhibits fusion of HIV-1 to a CD4+ CCR5+ cell, so as to thereby reduce the subject's HIV-1 viral load to 50% or less of the subject's HIV-1 viral load prior to administering the antibody to the subject.

This invention provides a composition for inhibiting HIV-1 infection comprising at least two compounds in synergistically effective amounts for inhibiting HIV-1 infection, wherein at least one of the compounds prevents the productive interaction between HIV-1 and an HIV-1 fusion co-receptor.

This invention also provides a composition which inhibits fusion of HIV-1 or an HIV-1 envelope glycoprotein$^+$ cell to a target cell, comprising at least two compounds in synergistically effective amounts for inhibiting fusion of HIV-1 or an HIV-1 envelope glycoprotein$^+$ cell to a target cell, wherein at least one of the compounds prevents the productive interaction between HIV-1 and HIV-1 fusion co-receptor.

This invention also provides a method of treating a subject afflicted with HIV-1 which comprises administering to the subject an effective dose of said compositions.

This invention also provides a method of preventing a subject from contracting HIV-1 which comprises administering to the subject an effective dose of said compositions.

This invention also provides an anti-CCR5 monoclonal antibody selected from the group consisting of PA8, PA9, PA10, PA11, PA12, and PA14.

This invention provides a composition which comprises an admixture of two compounds, wherein: (a) one compound is an antibody or portion thereof which binds to a CCR5 receptor; and (b) one compound retards gp41 from adopting a conformation capable of mediating fusion of HIV-1 to a CD4+ cell by binding noncovalently to an epitope on a gp41 fusion intermediate; wherein the relative mass ratio of the compounds in the admixture ranges from about 100:1 to about 1:100, the composition being effective to inhibit HIV-1 infection of the CD4+ cell.

This invention provides a composition which comprises an admixture of three compounds, wherein: (a) one compound is an antibody or portion thereof which binds to a CCR5 receptor; (b) one compound retards attachment of HIV-1 to a CD4+ cell by retarding binding of HIV-1 gp120 envelope glycoprotein to CD4 on the surface of the CD4+ cell; and (c) one compound retards gp41 from adopting a conformation capable of mediating fusion of HIV-1 to a CD4+ cell by binding noncovalently to an epitope on a gp41 fusion intermediate; wherein the relative mass ratio of any two of the compounds in the admixture ranges from about 100:1 to about 1:100, the composition being effective to inhibit HIV-1 infection of the CD4+ cell.

This invention provides a method of inhibiting HIV-1 infection of a CD4+ cell which comprises contacting the CD4+ cell with an amount of the composition of the subject invention effective to inhibit HIV-1 infection of the CD4+ cell so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor and (2) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor, (2) an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell, and (3) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

BRIEF DESCRIPTION OF THE FIGURES

FIG. 1:

Binding of anti-CCR5 monoclonal antibodies to $CCR5^+$ cells:

Flow cytometry was used to detect CCR5 protein expression on the surface of $L1.2-CCR5^+$ cells and freshly isolated, PHA/IL-2-stimulated PBMC. Cells were incubated with saturating concentrations of each mAb, which were detected with a PE-labeled anti-mouse IgG reporter antibody. Results from a representative experiment are shown. Results for each mAb are expressed both in mean fluorescence intensities (m.f.i.) and in % gated cells. Since PA8-PA12 and PA14 are all of the IgG1 subclass, their m.f.i. are directly comparable. 2D7 is an IgG2a.

Figure 7:
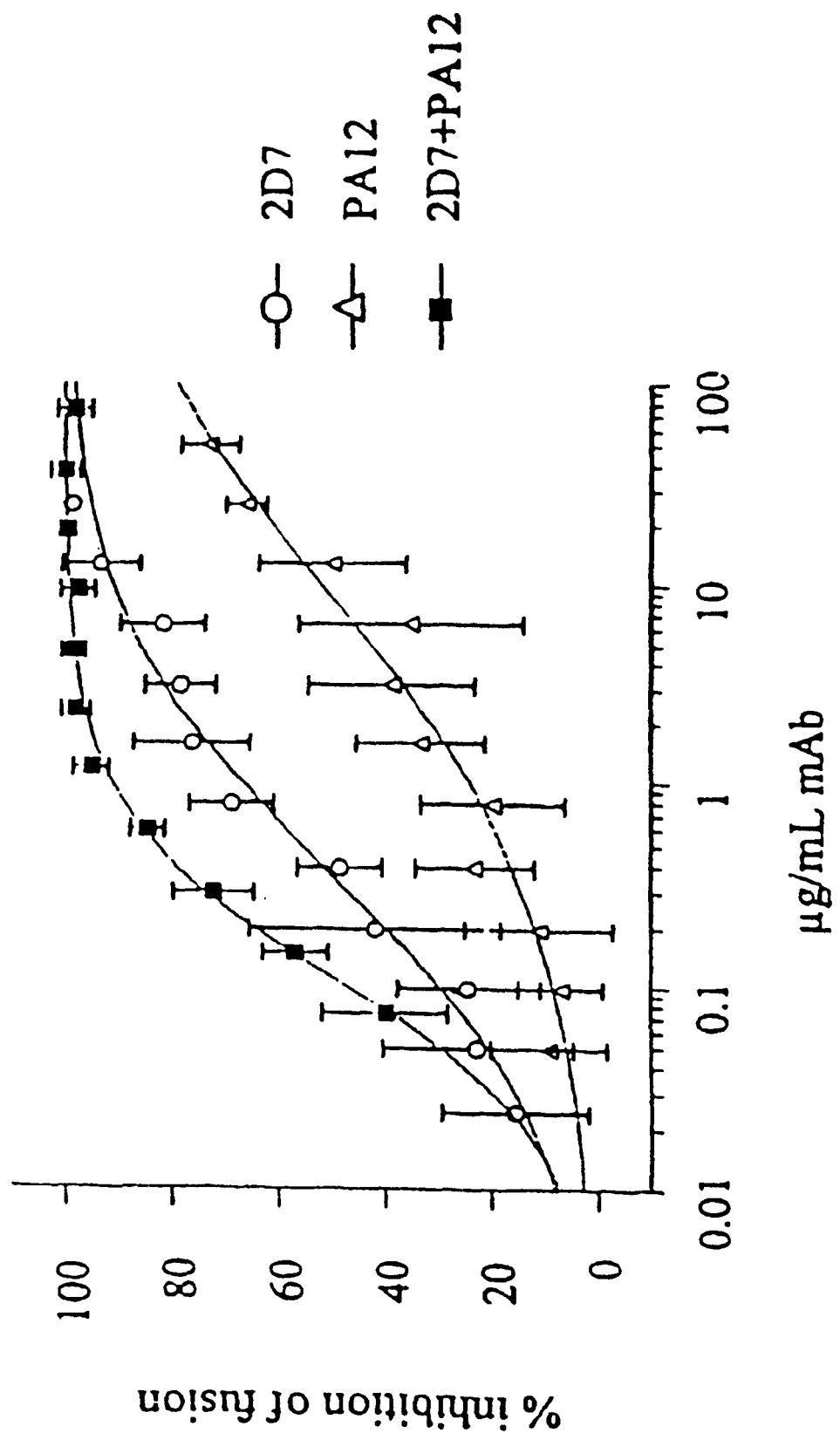

FIG. 2:

CI values for different combinations of mabs and viral inhibitors:

Experiments like those described in the legend of FIG. 7 were performed for different combinations of viral entry inhibitors. Anti-CCR5 mAbs were tested in combination with each other, CC-chemokines, and CD4-IgG2, which inhibits HIV-1 attachment to target cells. The PA11 and PA12 concentration range was 0-250 μg/ml; the 2D7 and PA14 concentration range was 0-25 μg/ml; the RANTES concentration range was 0-250 ng/ml; the CD4-IgG2 concentration range was 0-25 μg/ml. The concentrations of single-agents or their mixtures required to produce 50% and 90% inhibition of fusion or entry were quantitatively compared in a term known as the Combination Index (CI).

FIG. 3

$IC_{50}$ values for inhibition of cell-cell fusion, viral entry and gp120/sCD4 binding by anti-CCR5 mabs:

For comparative purposes we have summarized the $IC_{50}$ values obtained in the different assays that the anti-CCR5 mabs were tested in. $IC_{50}$ values were only calculated for mabs that could inhibit >90% of fusion, entry or binding.

FIG. 4

Epitope mapping of anti-CCR5 mabs:

A two color staining protocol was used to assess binding of mAbs to mutant CCR5 proteins, tagged at the C-terminus with the HA peptide. HeLa cells expressing CCR5 point mutants were incubated with saturating concentrations of each mAb followed by detection with a PE-labeled anti-mouse IgG. Cell surface co-receptor expression was measured by double-staining of the cells with a FITC labeled anti-HA mAb. The four grids correspond to the four extracellular domains of CCR5. The first row of every grid indicates the amino acid sequence of the corresponding CCR5 extracellular domain. Binding of anti-CCR5 mAbs to the alanine mutant of each residue is expressed as a percentage of binding to wild-type CCR5, as described in Materials and Methods.

FIG. 5

Inhibition of calcium mobilization into $CCR5^+$ cells by anti-CCR5 mAbs:

L1.2-$CCR5^+$ cells were loaded with Indo-1AM and stimulated sequentially with an anti-CCR5 mAb or PBS, followed with PANTES (a). Fluorescence changes were measured with a spectrofluorometer and the tracings are from a representative experiment. Calcium flux inhibition by PA14 and 2D7 was tested for a wide range of mAb concentrations (b). Results are plotted as % inhibition of calcium influx=[1−(relative fluorescence in the presence of mAb÷relative fluorescence in the absence of mAb)]×100%, and are means of values from three independent experiments.

FIG. 6

Inhibition of CCR5 co-receptor function by anti-CCR5 mAbs:

Inhibition of cell-cell fusion by anti-CCR5 mAbs was tested in the RET assay (a). 0-250 μg/ml of PA8-PA12, or 0-25 μg/ml of PA14 or 2D7, were added to a mix of HeLa-$Env_{JR-FL}^+$ and PM1 cells, labeled with F18 and R18 respectively. Fluorescence RET was measured after 4 h of incubation. Results are mean values from three independent experiments and are expressed as % inhibition of fusion=[1−(% RET in the presence of mAb÷% RET in the absence of mAb)]×100%. Inhibition of HIV-1 entry by anti-CCR5 mAbs was tested in a single round of replication luciferase based entry assay (b). U87-CD4$^+$CCR5$^+$ cells were infected with NLluc$^+$env$^-$ reporter virus carrying the JR-FL envelope in the presence of 0-250 µg/ml of PA8-PA12, or 0-25 µg/ml PA14 or 2D7. Luciferase activity (relative light units, r.l.u.) was measured in cell lysates 72 h post-infection. Results are from a representative experiment and are expressed as % inhibition of entry=[1−(r.l.u. in the presence of mAb÷r.l.u. in the absence of mAb)]×100%. Binding of biotinylated [b] gp120, sCD4 and b-gp120-CD4 complexes to L1.2-CCR5$^+$ cells (c). Strong binding is observed when gp120 derived from the R5 virus HIV-1$_{JR-FL}$ is complexed with an equimolar amount of sCD4. No binding is observed in the absence of sCD4 or for gp120 derived from the X4 virus HIV-1$_{LAI}$. Background binding to CCR5-L1.2 cells has been subtracted from all curves. Inhibition of gp120/sCD4 binding to L1.2-CCR5$^+$ cells was tested in the presence of varying concentrations of each antibody (d). Cells were pre-incubated in 96-well plates with an anti-CCR5 mAb followed by an incubation with a saturating concentration of biotinylated gp120/sCD4. Finally, binding of PE-labeled streptavidin to cells was measured using a fluorescence plate reader. Results are from a representative experiment and are expressed as % inhibition of gp120/sCD4 binding=[1−(m.f.i. in the presence of mAb m.f.i. in the absence of mAb)]×100%.

FIG. 7:

Synergistic inhibition of cell-cell fusion by PA12 and 2D7: Dose-response curves were obtained for the mAbs used individually and in combination. 0-50 µg/ml of PA12, 0-25 µg/ml 2D7, or a combination of the two in a 2:1 ratio, were added to a mix of HeLa-Env$_{JR-FL}{}^+$ and PM1 cells, labeled with R18 and F18 respectively. Fluorescence RET was measured after 4 hours of incubation. Results are expressed as % inhibition of fusion and are the means of values from three independent experiments. Data were analyzed using the median effect principle, which can be written $$f=1/[1+(K/c)^m] \tag{1}$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1. In the present case, K is equal to the IC$_{50}$ value. K and m were determined by curve-fitting the dose-response curves and Equation (1) was rearranged to allow calculation of c for a given f. The best-fit parameters for K and c are 8.8 µg/ml and 0.54 for PA12, 0.36 µg/ml and 0.68 for 2D7, and 0.11 µg/ml and 1.1 for their combination. These curves are plotted and indicate a reasonable goodness-of-fit between experiment and theory.

FIG. 8

Synergistic inhibition of HIV-1 entry CD4-IgG2 (-■-), T-20 (-●-), and a 25:1 CD4-IgG2:T-20 combination ( . . . ▲ . . . ) were analyzed for inhibition of HIV-1 entry in an env-mediated membrane fusion (RET) assay. Inhibitors were added to a mix of HeLa-Env$_{JR-FL}{}^+$ and PM1 cells previously labeled with F18 and R18 respectively. Fluorescence RET was measured after 4h of incubation, and percent inhibition was calculated as described [19]. Results are mean values from three independent experiments. The data were analyzed according to the median effect principle described in Equation (1). The best-fit parameters for K and m are 0.31 µg/ml and 0.73 for CD4-IgG2, 0.017 µg/ml and 0.92 for T-20, and 0.11 µg/ml and 1.0 for their combination. These curves are plotted and indicate a reasonable goodness-of-fit between experiment and theory ($r^2$=0.983, 0.998, and 0.996 for CD4-IgG2, T-20, and their combination, respectively). To normalize for the differences in potencies of the compounds, separate concentrations scales are used for CD4-IgG2 and the 25:1 CD4-IgG2:T-20 mixture and for T-20, as indicated.

FIG. 9

Combination indices for inhibition of HIV-1 entry by combinations of CD4-IgG2 and T-20. CD4-IgG2, T-20 and fixed mass ratios thereof were analyzed in the RET assay for the ability to inhibit env-mediated membrane fusion. The 25:1 (high) combination examined 10 three-fold serial dilutions of 250 µg/ml CD4-IgG2, 10 µg/ml T-20 and their combination. The 25:1 (low) combination examined 10 three-fold serial dilutions of 50 µg/ml CD4-IgG2, 2 µg/ml T-20 and their combination. The 5:1 combination examined 10 three-fold serial dilutions of 50 µg/ml CD4-IgG2, 2 µg/ml T-20, and their combination. The 1:1 combination examined 10 three-fold serial dilutions of 10 µg/ml CD4-IgG2, 10 µg/ml T-20 and their combination. Inhibition data from three or more independent assays were averaged prior to analysis. Dose-response curves for the various inhibitors and combinations were fit to Equation (1), which was then rearranged to calculate the inhibitor concentrations required to effect a given percent inhibition. The concentrations of the individual agents in an inhibitory mixture were calculated from their known mass ratios. These values were then used to calculate the Combination Index (CI) according to Equation (2). CI<1 indicates synergy, CI=1 indicates additive effects, and CI>1 indicates antagonism.

FIG. 10

Dose reductions observed for synergistic combinations of CD4-IgG2 and T-20. CD4-IgG2, T-20 and a 25:1 fixed mass ratio thereof were tested in the RET assay for the ability to inhibit env-mediated membrane fusion. Inhibition data from six independent assays were averaged. K and m were determined by curve-fitting the dose-response curves, and Equation (1) was rearranged to allow calculation of c for a given f for the single agents and their combination. Dose Reduction is the ratio of the inhibitor concentrations required to achieve a given degree of inhibition when the inhibitor is used alone v. in a synergistic combination.

FIG. 11

Dose reductions observed for combinations of CD4-IgG2, PRO 140, PA12 and T-20. The agents were tested individually and in combination for the ability to inhibit HIV env-mediated membrane fusion in the RET assay. a.) CD4-IgG2, PA12, T-20 and a ~1:1:10 fixed molar ratio thereof. b.) CD4-IgG2, PRO 140, T-20 and a ~2:1:20 fixed molar ratio thereof, c.) CD4-IgG2, PRO 140, T-20 and a ~4:1:30 fixed molar ratio thereof, and d.) PRO 140, T-20 and a 1:30 fixed molar ratio thereof where Dose Reduction is the ratio of the inhibitor concentrations required to achieve a given degree of inhibition when the inhibitor is used alone v. in a synergistic combination. 6-8 three-fold serial dilutions of a.) 125 nM CD4-IgG2, 167 nM PA12, 1100 nM T-20 and their combination, b.) 125 nM CD4-IgG2, 67 nM PRO 140, 1100 nM T-20 and their combination, c.) 125 nM CD4-IgG2, 33 nM PRO 140, 1100 nM T-20 and their combination, and d.) 36 nM PRO 140, 1100 nM T-20 and their combination were examined. The inhibitor concentrations required to effect a given percent inhibition were calculated. The concentrations of the individual agents in an inhibitory mixture were calculated from their known molar ratios. These values were then used to calculate the Combination Index (CI) according to Equation (2). CI<1 indicates synergy, CI =1 indicates additive effects, and CI>1 indicates antagonism.

FIG. 12:

Triple combination of PRO 542, PRO 140 and T-20 Synergistically Blocks HIV-1 Entry. PRO 542, PRO 140 and T-20 were used alone and in ~3:1:30 molar combination to inhibit HIV-1$_{JR-FL}$ env-mediated cell-cell fusion. The methodology for this assay is described in Litwin et al. (67).

FIG. 13:

PA14 treatment of JR-CSF infected hu-PBL-SCID mice. SCID mice were reconstitued with normal human PBMC and infected with HIV-1 JR-CSF. When viral steady state was reached, animals were treated with a single 1 milligram i.p. dose of PA14 or isotype control antibody and monitored for plamsa HIV RNA. (PA14-■-); (PA14-♦-); (PA14-●-); (control IgG -▲-).

FIGS. 14-15:

Plasma levels of viral RNA in HIV-1$_{JR-CSF}$ infected hu-PBL-SCID mice after administration of PRO 140.

Figure 14:
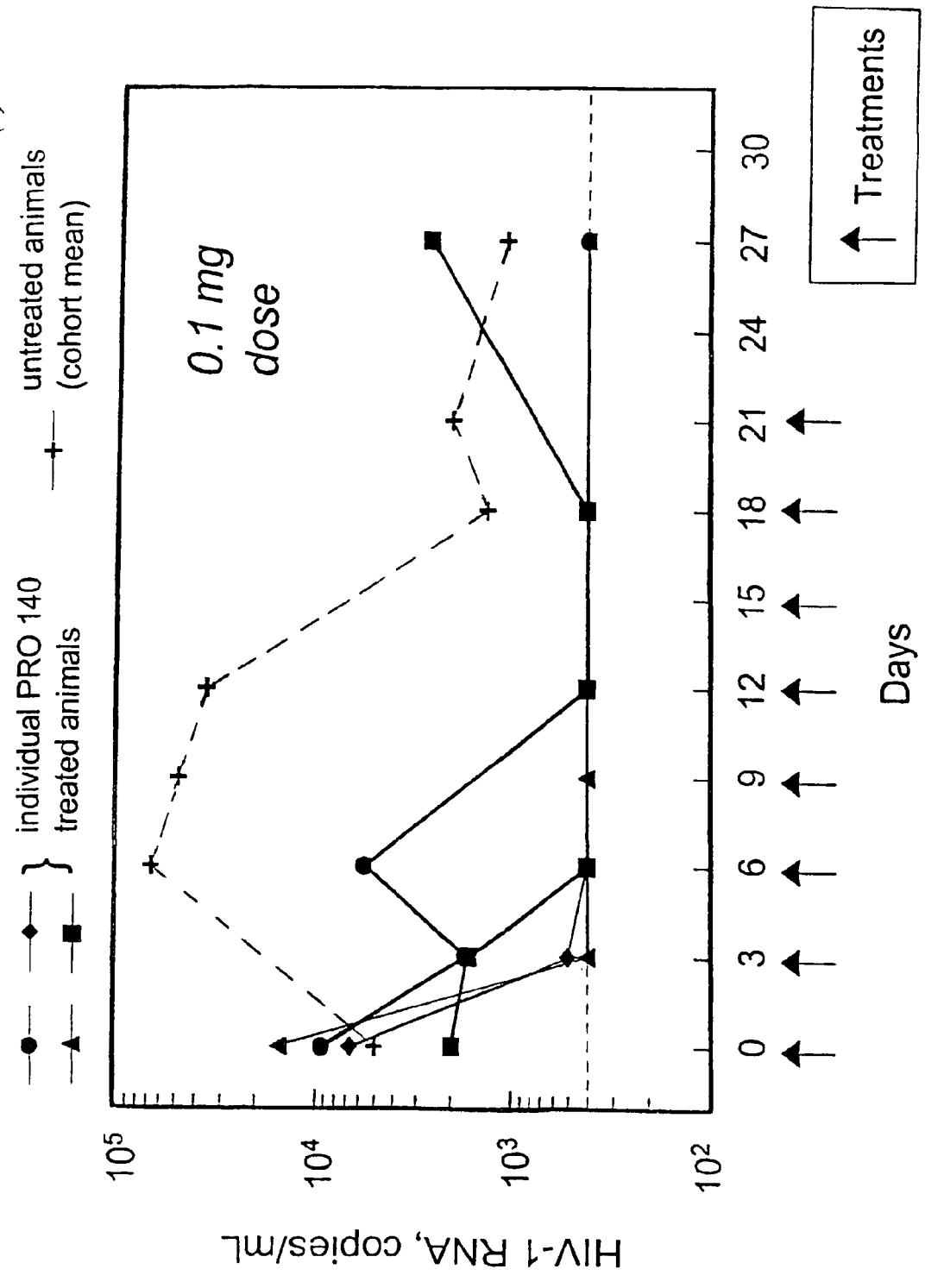
Figure 15:
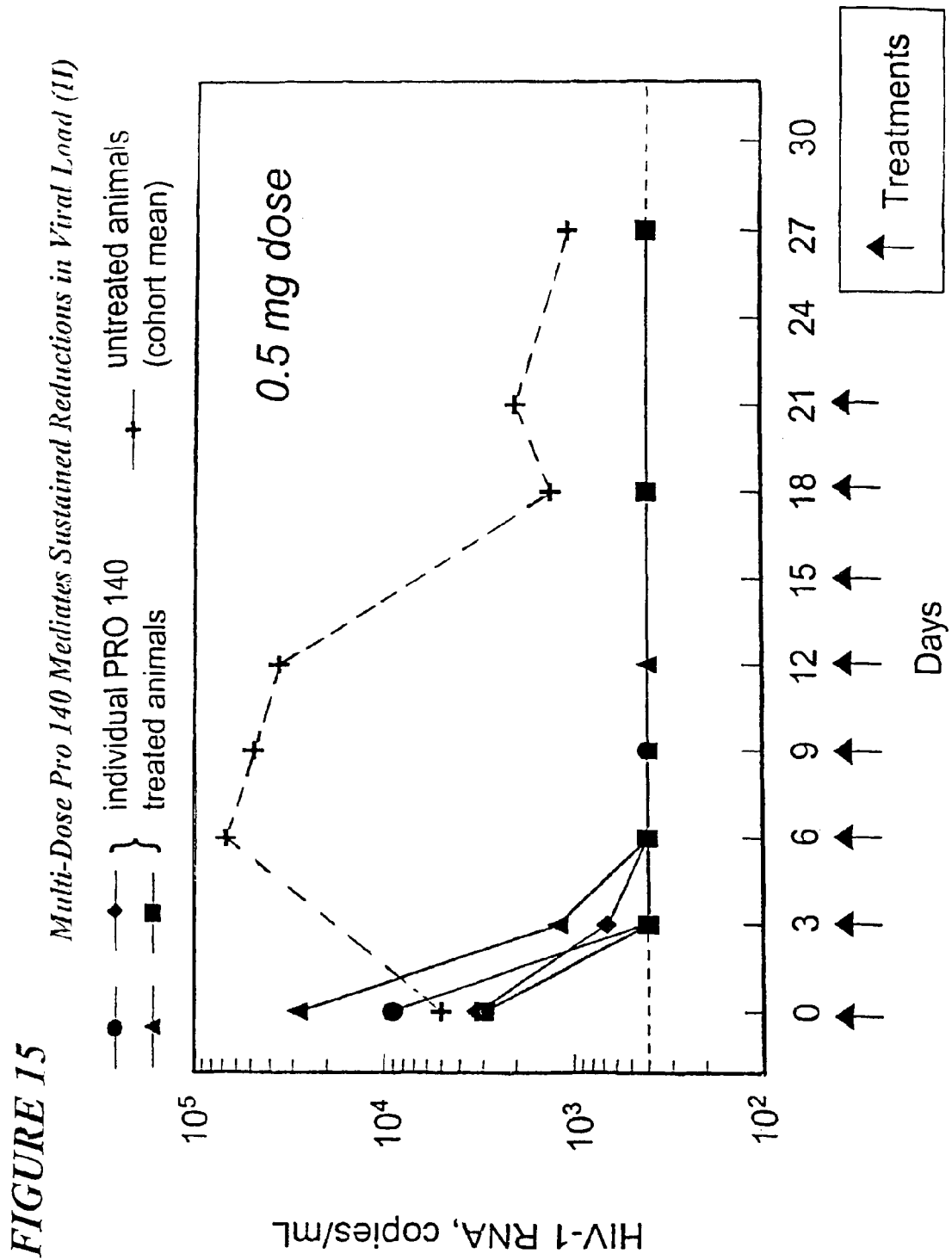

Hu-PBL-SCID mice with an established HIV-1$_{JR-CSF}$ infection were injected i.p. with multi-dose PRO 140 (solid line, FIGS. 14-15), or left untreated (dashed line). Injections are indicated by arrows. Each curve represents the values for a single animal. Plasma HIV-1 RNA levels were measured using quantitative Roche Amplicor RT-PCT assay. The limit of HIV-1 RNA detection, as indicated by the horizontal arrow, was 400 copies/ml.

DETAILED DESCRIPTION OF THE INVENTION

The plasmids CD4-IgG2-HC-pRcCMV and CD4-kLC-pRcCMV were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 10801 University Blvd, Manassas, Va. 20110-2209 under ATCC Accession Nos. 75193 and 75194, respectively. The plasmids were deposited with ATCC on Jan. 30, 1992. The plasmid designated pMA243 was similarly deposited in accordance with the Budapest Treaty with ATCC under Accession No. 75626 on Dec. 16, 1993.

The murine hybridomas PA8, PA9, PA10, PA11, PA12 and PA14 were deposited pursuant to, and in satisfaction of, the requirements of the Budapest Treaty on the International Recognition of the Deposit of Microorganisms (the "Budapest Treaty") for the Purposes of Patent Procedure with the American Type Culture Collection (ATCC), 10801 University Blvd, Manassas, Va. 20110-2209 under the following ATCC Accession Nos.: PA8 (ATCC No. HB-12605), PA9 (ATCC No. HB-12606), PA10 (ATCC No. HB-12607), PA11 (ATCC No. HB-12608), PA12 (ATCC No. HB-12609) and PA14 (ATCC No. HB-12610). The hybridomas were deposited on Dec. 2, 1998.

This invention provides a method of reducing an HIV infected subject's HIV-1 viral load which comprises administering to the subject an effective viral load reducing amount of an antibody which (a) binds to a CCR5 chemokine receptor and (b) inhibits fusion of HIV-1 to a CD4+ CCR5+ cell, so as to thereby reduce the subject's HIV-1 viral load to 50% or less of the subject's HIV-1 viral load prior to administering the antibody to the subject.

In one embodiment, the antibody is a monoclonal antibody. In one embodiment, the antibody includes but is not limited to PA8 (ATCC Accession No. HB-12605), PA9 (ATCC Accession No. HB-12606), PA10 (ATCC Accession No.HB-12607), PA11 (ATCC Accession No. HB-12608), PA12 (ATCC Accession No. HB-12609), and PA14 (ATCC Accession No. HB-12610). In a preferred embodiment, the antibody is PA14 (ATCC Accession No. HB-12610).

In one embodiment, the subject's HIV-1 viral load is reduced to 33% or less of the subject's HIV-1 viral load prior to administering the antibody to the subject.

In one embodiment, the subject's HIV-1 viral load is reduced to 10% or less of the subject's HIV-1 viral load prior to administering the antibody to the subject.

In one embodiment, the reduction of the subject's HIV-1 viral load is sustained for a period of time. In one embodiment, the period of time is at least one day. In one embodiment, the period of time is at least three days. In one embodiment, the period of time is at least seven days.

In one embodiment, the effective amount of the antibody is between about 1 mg and about 50 mg per kg body weight of the subject. In one embodiment, the effective amount of the antibody is between about 2 mg and about 40 mg per kg body weight of the subject. In one embodiment, the effective amount of the antibody is between about 3 mg and about 30 mg per kg body weight of the subject. In one embodiment, the effective amount of the antibody is between about 4 mg and about 20 mg per kg body weight of the subject. In one embodiment, the effective amount of the antibody is between about 5 mg and about 10 mg per kg body weight of the subject.

In one embodiment, the antibody is administered at least once per day. In one embodiment, the antibody is administered daily. In one embodiment, the antibody is administered every other day. In one embodiment, the antibody is administered every 6 to 8 days. In one embodiment, the antibody is administered weekly. The route of administration of the antibody includes but is not limited to intravenous, subcutaneous, intramuscular, intraperitoneal, oral and topical.

In one embodiment, the subject is a human being and the antibody is a humanized antibody.

This invention provides a composition for inhibiting HIV-1 infection comprising at least two compounds in synergistically effective amounts for inhibiting HIV-1 infection, wherein at least one of the compounds prevents with the productive interaction between HIV-1 and an HIV-1 fusion co-receptor.

As used herein, "composition" means a mixture. The compositions include but are not limited to those suitable for oral, rectal, intravaginal, topical, nasal, opthalmic, or parenteral, intravenous, subcutaneous, intramuscular, and intraperitoneal administration to a subject. As used herein, "parenteral" includes but is not limited to subcutaneous, intravenous, intramuscular, or intrasternal injections or infusion techniques.

As used herein, "HIV" means the human immunodeficiency virus and "HIV-1" means the human immunodeficiency virus type-1. HIV-1 includes but is not limited to extracellular virus particles and the forms of HIV-1 associated with HIV-1 infected cells. HIV-1$_{JR-FL}$ is a strain that was originally isolated at autopsy from the brain tissue of an AIDS patient [47]. The virus was co-cultured with lectin-stimulated normal human peripheral blood mononuclear cells. The virus has been cloned and the DNA sequences of its envelope glycoproteins are known (Genbank Accession #U63632). In terms of sensitivity to inhibitors of viral entry, HIV-1$_{JR-FL}$ is known to be highly representative of primary HIV-1 isolates [11,14,15,48-50].

As used herein, "HIV-1 infection" means the introduction of HIV-1 genetic information into a target cell, such as by fusion of the target cell membrane with HIV-1 or an HIV-1 envelope glycoprotein$^+$ cell. The target cell may be a bodily cell of a subject. In the preferred embodiment, the target cell is a bodily cell from a human subject.

As used herein, "inhibiting HIV-1 infection" means the reduction of the amount of HIV-1 genetic information introduced into a target cell population as compared to the amount that would be introduced without said composition.

As used herein, "compound" means a molecular entity, including but not limited to peptides, polypeptides, and other organic or inorganic molecules and combinations thereof.

As used herein, "synergistically effective" means that the combined effect of the compounds when used in combination is greater than their additive effects when used individually.

As used herein, "productive interaction" means that the interaction of HIV-1 and the HIV-1 co-receptor would lead to the fusion of said HIV-1 or HIV-1 envelope glycoprotein* cell and the membrane bearing the co-receptor. As used herein, "prevents the productive interaction" means that the amount of interaction is reduced as compared to the amount that would occur without the compound. The interactions may be prevented by masking or altering interactive regions on the co-receptor or HIV-1 or by altering the expression, aggregation, conformation, or association state of the co-receptor.

As used herein, "HIV-1 fusion co-receptor" means a cellular receptor that mediates fusion between the target cell expressing the receptor and HIV-1 or an HIV-1 envelope glycoprotein$^+$ cell. HIV-1 fusion co-receptors include but are not limited to CCR5, CXCR4 and other chemokine receptors.

This invention also provides a composition which inhibits fusion of HIV-1 or an HIV-1 envelope glycoprotein$^+$ cell to a target cell, comprising at least two compounds in synergistically effective amounts for inhibiting fusion of HIV-1 or an HIV-1 envelope glycoprotein$^+$ cell to a target cell, wherein at least one of the compounds prevents the productive interaction between HIV-1 and an HIV-1 fusion co-receptor.

As used herein, "fusion" means the joining or union of the lipid bilayer membranes found on mammalian cells or viruses such as HIV-1. This process is distinguished from the attachment of HIV-1 to a target cell. Attachment is mediated by the binding of the HIV-1 exterior glycoprotein to the human CD4 receptor, which is not a fusion co-receptor.

As used herein, "inhibits" means that the amount is reduced as compared with the amount that would occur without the composition.

As used herein, "target cell" means a cell capable of being infected by or fusing with HIV-1 or HIV-1 infected cells.

As used herein, "chemokine" means a cytokine that can stimulate leukocyte movement. They may be characterized as either cys-cys or cys-X-cys depending on whether the two amino terminal cysteine residues are immediately adjacent or separated by one amino acid. It includes but is not limited to RANTES, MIP-1α, MIP-1β, SDF-1 or another chemokine which blocks HIV-1 infection.

In one embodiment of the compositions described herein, the co-receptor is a chemokine receptor. In the preferred embodiment of the above compositions, the chemokine receptor is CCR5 or CXCR4. Several other chemokine and related receptors are known to function as HIV coreceptors including but not limited to CCR2, CCR3, CCR8, STRL33, GPR-15, CX3CR1 and APJ (69).

As used herein, "chemokine receptor" means a member of a homologous family of seven-transmembrane spanning cell surface proteins that bind chemokines. As used herein, "CCR5" is a chemokine receptor which binds members of the C-C group of chemokines and whose amino acid sequence comprises that provided in Genbank Accession Number 1705896 and related polymorphic variants. As used herein, "CXCR4" is a chemokine receptor which binds members of the C-X-C group of chemokines and whose amino acid sequence comprises that provided in Genbank Accession Number 400654 and related polymorphic variants.

In one embodiment of the compositions described herein, at least one of the compounds is a nonpeptidyl molecule. In one embodiment, the nonpeptidyl molecule is the bicyclam compound AMD3100. (16).

As used herein, "nonpeptidyl molecule" means a molecule that does not consist in its entirety of a linear sequence of amino acids linked by peptide bonds. A nonpeptidyl molecule may, however, contain one or more peptide bonds.

In one embodiment of the compositions described herein, at least one of the compounds is an antibody. In one embodiment, the antibody is a monoclonal antibody. In another embodiment, the antibody is a anti-chemokine receptor antibody. In one embodiment, the antibody is an anti-CXCR4 antibody. In a further embodiment, the anti CXCR4 antibody is 12G5. (43). In a preferred embodiment, the antibody is an anti-CCR5 antibody. The anti-CCR5 antibody includes but is not limited to PA8, PA9, PA10, PA11, PA12, PA14 and 2D7. In this composition the compounds are in an appropriate ratio. The ratio ranges from 1:1 to 1000:1.

The monoclonal antibodies PA8, PA9, PA10, PA11, PA12 and PA14 were deposited pursuant to and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Virginia 20110-2209 on Dec. 2, 1998 under the following Accession Nos.: ATCC Accession No. HB-12605 (PA8), ATCC Accession No. HB-12606 (PA9), ATCC Accession No.HB-12607 (PA10), ATCC Accession No. HB-12608 (Pl1), ATCC Accession No. HB-12609 (PA12 ) ATCC Accession No. HB-12610 (PA14 ).

In another embodiment of the compositions described herein, two or more of the compounds are antibodies. In one embodiment of the invention, the antibodies include but are not limited to PA8, PA9, PA10, PA11, PA12, PA14 and 2D7. In this composition the antibodies are in an appropriate ratio. The ratio ranges from 1:1 to 50:1.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgGl, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. Optionally, an antibody can be labeled with a detectable marker. Detectable markers include, for example, radioactive or fluorescent markers. The antibody may be a human or nonhuman antibody. The nonhuman antibody may be humanized by recombinant methods to reduce its immunogenicity in man. Methods for humanizing antibodies are known to those skilled in the art. As used herein, "monoclonal antibody," also designated as mAb, is used to describe antibody molecules whose primary sequences are essentially identical and which exhibit the same antigenic specificity. Monoclonal antibodies may be produced by hybridoma, recombinant, transgenic or other techniques known to one skilled in the art. As used herein, "anti-chemokine receptor antibody" means an antibody which recognizes and binds to an epitope on a chemokine receptor. As used herein, "anti-CCR5 antibody" means a monoclonal antibody which recognizes and binds to an epitope on the CCR5 chemokine receptor.

As used herein, "appropriate ratio" means mass or molar ratios wherein the compounds are synergistically effective.

In one embodiment of the compositions described herein, at least one compound is a chemokine or chemokine derivative. The chemokines include but are not limited to RANTES, MIP-1α, MIP-1β, SDF-1 or a combination thereof. In this composition, the compounds are in an appropriate ratio. The chemokine derivatives include but are not limited to Met-RANTES, AOP-RANTES, RANTES 9-68, or a combination thereof.

As used herein, "chemokine derivative" means a chemically modified chemokine. The chemical modifications include but are not limited to amino acid substitutions, additions or deletions, non-peptidyl additions or oxidations. One skilled in the art will be able to make such derivatives.

In another embodiment of the compositions described herein, at least one compound is an antibody and at least one compound is a chemokine or chemokine derivative. In this composition, the compounds are in an appropriate ratio. The ratio ranges from 100:1 to 1000:1.

In another embodiment of the compositions described herein, at least one compound binds to the gp41 subunit of the HIV-1 envelope glycoprotein. In one embodiment, at least one compound is the T-20 peptide inhibitor of HIV-1 entry (70).

In another embodiment of the compositions described herein, at least one of the compounds inhibits the attachment of HIV-1 to a target cell. In one embodiment, at least one compound binds CD4. In one embodiment, at least one compound is an HIV-1 envelope glycoprotein. In one embodiment, at least one compound is an anti-CD4 antibody. In one embodiment, at least one compound binds to the HIV-1 envelope glyoprotein. In one embodiment, at least one compound is an antibody to the HIV-1 envelope glycoprotein. In one embodiment, at least one compound is a CD4-based protein. In one embodiment, at least one compound is CD4-IgG2.

In another embodiment of the compositions described herein, at least one compound is an antibody and at least one compound binds to an HIV-1 envelope glycoprotein. In one embodiment, the compound is a CD4-based protein. In one embodiment, the compound is CD4-IgG2. In this composition, the compounds are in an appropriate ratio. The ratio ranges from 1:1 to 10:1. As used herein, "attachment" means the process that is mediated by the binding of the HIV-1 envelope glycoprotein to the human CD4 receptor, which is not a fusion co-receptor.

As used herein, "CD4" means the mature, native, membrane-bound CD4 protein comprising a cytoplasmic domain, a hydrophobic transmembrane domain, and an extracellular domain which binds to the HIV-1 gp120 envelope glycoprotein.

As used herein, "HIV-1 envelope glycoprotein" means the HIV-1 encoded protein which comprises the gp120 surface protein, the gp41 transmembrane protein and oligomers and precursors thereof.

In one embodiment of the compositions described herein at least one of the compounds comprises a polypeptide which binds to a CCR5 epitope. In one embodiment, the epitope is located in the N-terminus, one of the three extracellular loop regions or a combination thereof. In one embodiment, the epitope is located in the N-terminus. The epitope can comprise N13 and Y15 in the N-terminus. The epitope can comprise comprises Q4 in the N-terminus. In another embodiment, the epitope includes residues in the N-terminus and second extracellular loop. The epitope can comprise D2, Y3, Q4,S7, P8 and N13 in the N-terminus and Y176 and T177 in the second extracellular loop. The epitope can comprise D2, Y3, Q4, P8 and N13 in the N-terminus and Y176 and T177 in the second extracellular loop. The epitope can comprise D2 in the N-terminus and R168 and Y176 in the secona extracellular loop. In one embodiment, the epitope is located in the second extra cellular loop. The epitope can comprise Q170 and K171 in the second extracellular loop. The epitope can comprise Q170 and E172 in the second extra cellular loop.

As used herein, the following standard abbreviations are used throughout the specification to indicate specific amino acids: A=ala=alanine; R=arg=arginine; N=asn=asparagine D=asp=aspartic acid; C=cys=cysteine; Q=gln=glutamine; E=glu=glutamic acid; G=gly=glycine; H=his=histidine; I=ile=isoleucine; L=l e u=l e u c i n e; K=lys=lysine; M=met=methionine; F=phe=phenylalanine; P=pro=proline; S=ser=serine; T=thr=threonine; W=trp=tryptophan; Y=tyr=tyrosine; and V=val=valine.

As used herein, "polypeptide" means two or more amino acids linked by a peptide bond. As used herein, "epitope" means a portion of a molecule or molecules that forms a surface for binding antibodies or other compounds. The epitope may comprise contiguous or noncontiguous amino acids, carbohydrate or other nonpeptidyl moieties or oligomer-specific surfaces. As used herein, "N-terminus" means the sequence of amino acids spanning the initiating methionine and the first transmembrane region. As used herein, "second extra cellular loop" means the sequence of amino acids that span the fourth and fifth transmembrane regions and are presented on the surface.

In one embodiment of the compositions described herein at least one of the compounds comprises a light chain of an antibody. In another embodiment of the above compositions at least one of the compounds comprises a heavy chain of an antibody. In another embodiment of the above compositions at least one of the compounds comprises the Fab portion of an antibody. In another embodiment of the above compositions at least one of the compounds comprises the variable domain of an antibody. In another embodiment, the antibody is produced as a single polypeptide or "single chain" antibody which comprises the heavy and light chain variable domains genetically linked via an intervening sequence of amino acids. In another embodiment of the above compositions at least one of the compounds comprises one or more CDR portions of an antibody.

As used herein, "heavy chain" means the larger polypeptide of an antibody molecule composed of one variable domain (VH) and three or four constant domains (CH1, CH2, CH3, and CH4), or fragments thereof.

As used herein, "light chain" means the smaller polypeptide of an antibody molecule composed of one variable domain (VL) and one constant domain (CL), or fragments thereof.

As used herein, "Fab" means a monovalent antigen binding fragment of an immunoglobulin that consists of one light chain and part of a heavy chain. It can be obtained by brief papain digestion or by recombinant methods.

As used herein, "F(ab')2 fragment" means a bivalent antigen binding fragment of an immunoglobulin that consists of both light chains and part of both heavy chains. It cen be obtained by brief pepsin digestion or recombinant methods.

As used herein, "CDR" or "complementarity determining region" means a highly variable sequence of amino acids in the variable domain of an antibody.

This invention provides a composition described herein and a pharmaceutically acceptable carrier. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method of treating a subject afflicted with HIV-1 which comprises administering to the subject an effective dose of a composition described herein.

This invention provides a method of treating a subject afflicted with HIV-1 which comprises administering to the subject an effective amount of an antibody described herein so as to treat the subject. In one embodiment, the antibody may be enough to decrease the subject's viral load. In one embodiment, the antibody is an anti-CCR5 antibody described herein.

As used herein, "subject" means any animal or artificially modified animal capable of becoming HIV-infected. Artificially modified animals include, but are not limited to, SCID mice with human immune systems. The animals include but are not limited to mice, rats, dogs, guinea pigs, ferrets, rabbits, and primates. In the preferred embodiment, the subject is a human.

As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1. As used herein, "afflicted with HIV-1" means that the subject has at least one cell which has been infected by HIV-1.

The dose of the composition of the invention will vary depending on the subject and upon the particular route of administration used. Dosages can range from 0.1 to 100,000 μg/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming HIV-1 infected. A person of ordinary skill in the art can perform simple titration experiments to determine what amount is required to treat the subject. As used herein, "contracting HIV-1" means becoming infected with HIV-1, whose genetic information replicates in and/or incorporates into the host cells.

This invention provides a method of preventing a subject from contracting HIV-1 which comprises administering to the subject an effective dose of a composition described herein.

This invention provides humanized forms of the antibodies described herein As used herein, "humanized" describes antibodies wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody would retain a similar antigenic specificity as the original antibody, i.e., in the present invention, the ability to bind CCR5.

One skilled in the art would know how to make the humanized antibodies of the subject invention. Various publications, several of which are hereby incorporated by reference into this application, also describe how to make humanized antibodies. For example, the methods described in U.S. Pat. No. 4,816,567 (71) comprise the production of chimeric antibodies having a variable region of one antibody and a constant region of another antibody.

U.S. Pat. No. 5,225,539 (72) describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 (73) and 5,693,761 go (74) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The above U.S. Pat. Nos. 5,585,089 and 5,693,761, and WO 90/07861 (75) also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3Å of the CDRs in a three dimensional model of the antibody and is predicted to be capable of interacting with the CDRs. The above methods are merely illustrative of some of the methods that one skilled in the art could employ to make humanized antibodies.

This invention provides isolated nucleic acid molecules encoding these anti-CCR5 monoclonal antibodies or their humanized versions. The nucleic acid molecule can be RNA, DNA or cDNA. In one embodiment, the nucleic acid molecule encodes the light chain. In one embodiment, the nucleic acid molecule encodes the heavy chain. In one embodiment, the nucleic acid encodes both the heavy and light chains. In one embodiment, one or more nucleic acid molecules encode the Fab portion. In one embodiment, one or more nucleic acid molecules encode CDR portions. In one embodiment, the nucleic acid molecule encodes the variable domain.

This invention provides a composition which comprises an admixture of two compounds, wherein: (a) one compound is an antibody or portion thereof which binds to a CCR5 receptor; and (b) one compound retards gp41 from adopting a conformation capable of mediating fusion of HIV-1 to a CD4+ cell by binding noncovalently to an epitope on a gp41 fusion intermediate; wherein the relative mass ratio of the compounds in the admixture ranges from about 100:1 to about 1:100, the composition being effective to inhibit HIV-1 infection of the CD4+ cell.

This invention provides a composition which comprises an admixture of three compounds, wherein: (a) one compound is an antibody or portion thereof which binds to a CCR5 receptor; (b) one compound retards attachment of HIV-1 to a CD4+ cell by retarding binding of HIV-1 gp120 envelope glycoprotein to CD4 on the surface of the CD4+ cell; and (c) one compound retards gp41 from adopting a conformation capable of mediating fusion of HIV-1 to a CD4+ cell by binding noncovalently to an epitope on a gp41 fusion intermediate; wherein the relative mass ratio of any two of the compounds in the admixture ranges from about 100:1 to about 1:100, the composition being effective to inhibit HIV-1 infection of the CD4+ cell.

As used herein, "gp41 fusion intermediates" includes structures, conformations, and oligomeric states that are preferentially and transiently presented or exposed on the HIV-1 envelope glycoprotein gp41 during the process of HIV-1 env-mediated membrane fusion. These intermediates may form upon interaction of HIV-1 with cellular receptors or may be present in partially or fully occluded states on HIV-1 prior to its interaction with cellular receptors. "gp41 fusion intermediates" do not include fusogenic gp41 conformations that cannot provide targets for therapeutic intervention.

The gp41 fusion intermediates may contain multiple epitopes that are transiently exposed during fusion and can provide targets for therapeutic intervention. As used herein, an "N-terminal gp41 epitope" may comprise all or portions of the sequences from amino acid A541 to Q590. As used herein, a "C-terminal gp41 epitope" may comprise all or portions of the sequences from amino acid W628 to L663. These epitopes have the potential to form coiled-coils of interacting alpha helical segments by virtue of heptad (sequence of seven amino acids) repeats containing hydrophobic amino acids at positions 1 and 4 of the heptad. The amino acid numbering system is for the HxB2 isolate of HIV-1 (Genbank Protein Accession No. AAB50262). Because of the sequence variability of HIV-1 envelope proteins, the composition, size and precise location of such sequences may be different for different viral isolates. The gp41 fusion intermediates may also present other linear or conformational epitopes that are transiently expressed during HIV-1 entry. An inhibitor may target multiple epitopes present on gp41 fusion intermediates. Alternatively, separate inhibitors may be used in combination to target one or more epitopes present on gp41 fusion intermediates.

As used herein, "fusogenic" means capable of mediating membrane fusion. As used herein, "HIV-1 fusion coreceptor" means a cellular receptor that mediates fusion between the target cell expressing the receptor and HIV-1 or an HIV-1 envelope glycoprotein$^+$ cell. HIV-1 fusion co-receptors include but are not limited to CCR5, CXCR4 and other chemokine receptors. As used herein, "fusion" means the joining or union of the lipid bilayer membranes found on mammalian cells or viruses such as HIV-1. This process is distinguished from the attachment of HIV-1 to a target cell. Attachment is mediated by the binding of the HIV-1 exterior glycoprotein to the human CD4 receptor, which is not a fusion co-receptor.

As used herein, "retards" means that the amount is reduced. As used herein, "attachment" means the process that is mediated by the binding of the HIV-1 envelope glycoprotein to the human CD4 receptor, which is not a fusion co-receptor. As used herein, "CD4" means the mature, native, membrane-bound CD4 protein comprising a cytoplasmic domain, a hydrophobic transmembrane domain, and an extracellular domain which binds to the HIV-1 gp120 envelope glycoprotein.

As used herein, "epitope" means a portion of a molecule or molecules that form a surface for binding antibodies or other compounds. The epitope may comprise contiguous or noncontiguous amino acids, carbohydrate or other nonpeptidyl moities or oligomer-specific surfaces.

The compounds of the subject invention have shown to demonstrate a synergistic effect. As used herein, "synergistic" means that the combined effect of the compounds when used in combination is greater than their additive effects when used individually.

In one embodiment of the composition of this invention, the compound which retards attachment of HIV-1 to the CD4+ cell by retarding binding of HIV-1 gp120 envelope glycoprotein to CD4 on the surface of the CD4+ cell is a CD4-based protein. As used herein, "CD4-based protein" means any protein comprising at least one sequence of amino acid residues corresponding to that portion of CD4 which is required for CD4 to form a complex with the HIV-1 gp120 envelope glycoprotein. In one embodiment the CD4-based protein is a CD4-immunoglobulin fusion protein. In one embodiment the CD4-immunoglobulin fusion protein is CD4-IgG2, wherein the CD4-IgG2 comprises two heavy chains and two lights chains, wherein the heavy chains are encoded by an expression vector designated CD4-IgG2HC-pRcCMV (ATCC Accession No. 75193) and the light chains are encoded by an expression vector designated CD4-kLC-pRcCMV (ATCC Accession No. 75194). As used herein, CD4-IgG2 is also referred to as PRO 542.

In one embodiment of the composition of this invention, the compound which retards attachment of HIV-1 to the CD4+ cell by retarding binding of HIV-1 gp120 envelope glycoprotein to CD4 on the surface of the CD4+ cell is a protein, the amino acid sequence of which comprises that of a protein found in HIV-1 as an envelope glycoprotein.

In one embodiment, the protein binds to an epitope of CD4 on the surface of the CD4+ cell. In one embodiment the envelope glycoprotein is selected from the group consisting of gp120, gp160, and gp140.

In one embodiment of the composition of this invention, the compound which retards the attachment of HIV-1 to the CD4+ cell by retarding binding of HIV-1 gp120 envelope glycoprotein to CD4 on the surface of the CD4+ cell is an antibody or portion of an antibody. In one embodiment, the antibody is a monoclonal antibody. In one embodiment, the monoclonal antibody is a human, humanized or chimeric antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. In one embodiment, the monoclonal antibody is an IgG, IgM, IgD, IgA, or IgE monoclonal antibody.

As used herein, "antibody" means an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. It includes, by way of example, both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man. Methods for humanizing antibodies are known to those skilled in the art.

In one embodiment, the antibody binds to an HIV-1 envelope glycoprotein. In one embodiment, the HIV-1 envelope glycoprotein is selected from the group consisting of gp120 and gp160. In one embodiment, the HIV-1 envelope glycoprotein is gp120 and the monoclonal antibody which binds to gp120 is IgG1b12 or F105. IgG1b12 is listed as item #2640 in the NIH AIDS Research and Reference Reagent Program Catalog. F105 is listed as item #857 in the NIH AIDS Research and Reference Reagent Program Catalog. In one embodiment, the antibody binds to an epitope of CD4 on the surface of the CD4+ cell.

In one embodiment of the composition of this invention, the compound which retards attachment of HIV-1 to the CD4+ cell by retarding binding of HIV-1 gp120 envelope glycoprotein to CD4 on the surface of the CD4+ cell is a peptide. In one embodiment of the composition of this invention, the compound which retards attachment of HIV-1 to the CD4+ cell by retarding binding of HIV-1 gp120 envelope glycoprotein to CD4 on the surface of the CD4+ cell is a nonpeptidyl agent. As used herein, "nonpeptidyl" means that the agent does not consist in its entirety of a linear sequence of amino acids linked by peptide bonds. A nonpeptidyl agent may, however, contain one or more peptide bonds.

In one embodiment of the composition of this invention, the compound which retards gp41 from adopting a conformation capable of mediating fusion of HIV-1 to a CD4+ cell by binding noncovalently to an epitope on a gp41 fusion intermediate is an antibody. In one embodiment the antibody is a monoclonal antibody. In one embodiment, the antibody is a polyclonal antibody.

In one embodiment of the composition of this invention, the compound which retards gp41 from adopting a conformation capable of mediating fusion of HIV-1 to a CD4+ cell by binding noncovalently to an epitope on a gp41 fusion intermediate is a peptide.

In one embodiment of the composition of this invention, the compound which retards gp41 from adopting a conformation capable of mediating fusion of HIV-1 to a CD4+ cell by binding noncovalently to an epitope on a gp41 fusion intermediate is a fusion protein which comprises a peptide which inicudes but is not limited to T-20 (SEQ ID NO: 1), DP107 (SEQ ID NO: 2), N34 (SEQ ID NO: 3), C28 (SEQ ID NO: 4), and N34(L6)C28 (SEQ ID NO: 5). In one embodiment the peptide is selected from the group consisting of T-20 (SEQ ID NO: 1), DP107 (SEQ ID NO: 2), N34 (SEQ ID NO: 3), C28 (SEQ ID NO: 4), and N34 (L6) C28 (SEQ ID NO: 5). In one embodiment, the peptide is T-20 (SEQ ID NO: 1).

As used herein, "T-20" and "DP178" are used interchangeably to denote a peptide having the following amino acid sequence: YTSLIHSLIEESQNQQEKNEQELLELDK-WASLWNWF (SEQ ID NO: 1) and as described [29,32]. DP107 has the following amino acid sequence: NNLL-RAIEAQQHLLQLTVWGIKQLQARILAVERYLKDQ (SEQ ID NO: 2). N34 has the following amino acid sequence: SGIVQQQNNLL-RAIEAQQHLLQLTVWGIKQLQAR (SEQ ID NO: 3). C28 has the following amino acid sequence: WMEWDREINNY-TSLIHSLIEESQNQQEK (SEQ ID NO: 4). N34 (L6) C28 has the following amino acid sequence: SGIVQQQNNLL-RAIEAQQHLLQLTVWGI KQLQARSGGRGGWMEW-DREINNYTSLI HSLIEESQNQQEK (SEQ ID NO: 5).

In one embodiment of the above composition, the peptide is a mutant peptide which (1) consists of amino acids having a sequence identical to that of a wildtype peptide selected from the group consisting of T-20 (SEQ ID NO: 1), DP-107 (SEQ ID NO: 2), N34 (SEQ ID NO: 3), C28 (SEQ ID NO: 4), and N34 (L6)C28 (SEQ ID NO: 5), except for an addition of at least one glycine residue to a 5' end of the peptide, to a 3' end of the peptide, or to both ends of the peptide and (2) retards gp41 from adopting a conformation capable of mediating fusion of HIV-1 to a CD4+ cell by binding noncovalently to an epitope on a gp41 fusion intermediate.

In one embodiment of the compnosition of this invention, the compound which retards gp41 from adopting a conformation capable of mediating fusion of HIV-1 to a CD4+ cell by binding noncovalently to an epitope on a gp41 fusion intermediate is a non-peptidyl agent.

In one embodiment of the composition of this invention, the antibody which binds to a CCR5 receptor includes but is not limited to PA8 (ATCC Accession No. HB-12605), PA10 (ATCC Accession No.12607), PA11 (ATCC Accession No. HB-12608), PA12 (ATCC Accession No. HB-12609), and PA14 (ATCC Accession No. HB-12610). In one embodiment, the antibody is a monoclonal antibody. In one embodiment, the monoclonal antibody is a human, humanized or chimeric antibody. In one embodiment, the portion of the antibody is a Fab fragment of the antibody. In one embodiment, the portion of the antibody comprises the variable domain of the antibody. In one embodiment, the portion of the antibody comprises a CDR portion of the antibody. In one embodiment, the monoclonal antibody is an IgG, IgM, IgD, IgA, or IgE monoclonal antibody.

In one embodiment of the composition of this invention, the relative mass ratio of each such compound in the admixture ranges from about 25:1 to about 1:1. In one embodiment, the mass ratio is about 25:1. In one embodiment, the mass ratio is about 5:1. In one embodiment, the mass ratio is about 1:1.

In one embodiment of the composition of this invention, the composition is admixed with a carrier. The carriers of the subject invention include but are not limited to aerosol, intravenous, oral or topical carriers. Pharmaceutically acceptable carriers are well known to those skilled in the art. Such pharmaceutically acceptable carriers may include but are not limited to aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/ aqueous solutions, emulsions or suspensions, saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention provides a method of inhibiting HIV-1 infection of a CD4+ cell which comprises contacting the CD4+ cell with an amount of the composition of the subject invention effective to inhibit HIV-1 infection of the CD4+ cell so as to thereby inhibit HIV-1 infection of the CD4+ cell.

In one embodiment, the CD4+ cell is present in a subject and the contacting is effected by administering the composition to the subject.

As used herein, "subject" includes any animal or artificially modified animal capable of becoming HIV-infected. Artificially modified animals include, but are not limited to, SCID mice with human immune systems. The animals include but are not limited to mice, rats, dogs, cats, guinea pigs, ferrets, rabbits, and primates. In the preferred embodiment, the subject is a human.

As used herein, "administering" may be effected or performed using any of the methods known to one skilled in the art, which includes intralesional, intraperitoneal, intramuscular, subcutaneous, intravenous, liposome mediated delivery, transmucosal, intestinal, topical, nasal, oral, anal, ocular or otic delivery. The compounds may be administered separately (e.g., by different routes of administration, sites of injection, or dosing schedules) so as to combine in synergistically effective amounts in the subject.

The dose of the composition of the invention will vary depending on the subject and upon the particular route of administration used. Dosages can range from 0.1 to 100,000 µg/kg. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

As used herein, "effective dose" means an amount in sufficient quantities to either treat the subject or prevent the subject from becoming infected with HIV-1. A person of ordinary skill in the art can perform simple titration experiments to determine what amount is required to treat the subject.

In one embodiment, the effective amount of the composition comprises from about 0.000001 mg/kg body weight to about 100 mg/kg body weight of the subject.

This invention provides a method of inhibiting HIV-1 infection of a CD4+ cell which comprises contacting the CD4+ cell with (1) an amount of an antibody which binds to a CCR5 receptor and (2) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

This invention provides a method of inhibiting HIV-1 infection of a CD4+ cell which comprises contacting the CD4+ cell with (1) an amount of an antibody which binds to a CCR5 receptor, (2) an amount of a compound which retards attachment of HIV-1 to the CD4+ cell by retarding binding of HIV-1 gp120 envelope glycoprotein to CD4 on the surface of the CD4+ cell effective to inhibit HIV-1 infection of the CD4+ cell, and (3) an amount of a compound which retards gp41 from adopting a conformation capable of mediating fusion of HIV-1 to a CD4+ cell by binding noncovalently to an epitope on a gp41 fusion intermediate, so as to thereby inhibit HIV-1 infection of the CD4+ cell.

In one embodiment, the CD4+ cell is present in a subject and the contacting is effected by administering the compounds to the subject. In one embodiment, the compounds are administered to the subject simultaneously. In one embodiment, the compounds are administered to the subject at different times. In one embodiment, the compounds are administered to the subject by different routes of administration.

The subject invention has various applications which includes HIV treatment such as treating a subject who has become afflicted with HIV. As used herein, "afflicted with HIV-1" means that the subject has at least one cell which has been infected by HIV-1. As used herein, "treating" means either slowing, stopping or reversing the progression of an HIV-1 disorder. In the preferred embodiment, "treating" means reversing the progression to the point of eliminating the disorder. As used herein, "treating" also means the reduction of the number of viral infections, reduction of the number of infectious viral particles, reduction of the number of virally infected cells, or the amelioration of symptoms associated with HIV-1. Another application of the subject invention is to prevent a subject from contracting HIV. As used herein, "contracting HIV-1" means becoming infected with HIV-1, whose genetic information replicates in and/or incorporates into the host cells. Another application of the subject invention is to treat a subject who has become infected with HIV-1. As used herein, "HIV-1 infection" means the introduction of HIV-1 genetic information into a target cell, such as by fusion of the target cell membrane with HIV-1 or an HIV-1 envelope glycoprotein$^+$ cell. The target cell may be a bodily cell of a subject. In the preferred embodiment, the target cell is a bodily cell from a human subject. Another application of the subject invention is to inhibit HIV-1 infection. As used herein, "inhibiting HIV-1 infection" means reducing the amount of HIV-1 genetic information introduced into a target cell population as compared to the amount that would be introduced without said composition.

The nucleic acids, polypeptides and antibodies described herein may be isolated and/or purified. One skilled in the art would know how to isolate and/or purify them.

This invention will be better understood from the Experimental Details that follow. However, one skilled in the art will readily appreciate that the specific methods and results discussed are merely illustrative of the invention as described more fully in the claims that follow thereafter.

FIRST SERIES OF EXPERIMENTS

Experimental Details:

A. Materials and Methods Reagents

MAb 2D7 was purchased from Pharmingen (San Diego, Calif.) and CC- and CXC-chemokines were obtained from R&D Systems (Minneapolis, Minn.). CD4-IgG2 (1), soluble(s) CD4 (2) and recombinant HIV-1$_{JR-FL}$ gp120, were produced by Progenics Pharmaceuticals, Inc. (59).

Isolation and purification of anti-CCR5 mAbs

L1.2-CCR5$^+$ cells (63) were incubated for 16 h in the presence of 5 mM sodium butyrate, which activates transcription from the cytomegalovirus (CMV) promoter that controls CCR5 expression, resulting in a 10-fold increase in cell surface co-receptor density. Female Balb/c mice were immunized intraperitoneally with $10^7$ L1.2-CCR5$^+$ cells at 3-week intervals, and administered an intravenous boost of $10^7$L1.2-CCR5$^+$ cells three days prior to splenectomy. Splenocytes were fused with the Sp2/0 cell line. In a primary screen, supernatants from ten thousand hybridoma cultures were tested; one hundred and twenty of these inhibited HIV-1 envelope-mediated fusion between PM1 cells (10), which naturally express CCR5 and CD4, and HeLa-Env$_{JR-FL}$$^+$ cells in a resonance energy transfer (RET) assay, as previously described (19, 38). Hybridomas that produced the most potently inhibitory supernatants and that also stained CCR5$^+$ cells were sub-cloned by limiting dilution. Ascites fluids were prepared by Harlan Bioproducts for Science, Inc. (Indianapolis, Ind.) from Balb/c mice that were injected with hybridomas producing the anti-CCR5 mAbs PA8, PA9, PA10, PA11, PA12 and PA14. The mAbs were individually purified to >95% homogeneity by precipitation with ammonium sulfate followed by protein-A chromatography. All mAbs were resuspended in phosphate buffered saline (PBS) at a final concentration of 5 mg/ml.

Fluorescence activated cell sorting (FACS) analysis and epitope mapping of anti-CCR5 mabs Flow cytometry was used to detect cell-surface reactivity of mAbs PA8-PA12 and PA14 with CCR5. Sodium butyrate treated L1.2-CCR5$^+$ cells ($10^6$) were incubated with 0.25 µg of antibody, for 20 min at 4° C. in 0.1% sodium azide (NaN$_3$) in 50 µl of Dulbecco's PBS (DPBS). The CCR5 mAb 2D7 was used as a positive control, a non-specific murine IgG1 was used as a negative control. The cells were spun down, washed and incubated with phycoerythrin (PE)-labeled goat anti-mouse IgG (Caltag, Burlingame, Calif.) diluted 1:100, under the same conditions as the first antibody incubation. Finally, cells were analyzed by flow cytometry. PBMC were isolated and stimulated as previously described (60) and stained using similar methods.

A similar procedure was used for epitope mapping of the anti-CCR5 mabs. A panel of seventy CCR5 point mutants has been described (20, 24, 52). The coding sequences of these proteins are sub-cloned into the pcDNA3.1 vector (Stratagene) from which transcription can be driven by a 5' T7-polymerase promoter. The CCR5 mutants carry a 9-residue hemaglutinin (HA) tag at the C-terminus for detection of protein in cell lysates or by flow cytometry. HeLa cells ($2\times10^6$) were incubated for 5 h with 20 µg/ml lipofectin and an equal amount of wild-type or mutant CCR5-expressing plasmid in OPTI-MEM (Life Technologies, Gaithersburg, Md.). The cells were then infected for 12 h with $2\times10^7$ p.f.u. of vTF7 (23) to boost CCR5 expression, detached with 2 mM ethylenediamine tetracetic acid (EDTA) in PBS and washed once with binding buffer (1% BSA, 0.05% NaN$_3$ in DPBS). Cells ($1\times10^6$) were surface labeled with mAbs as described in the previous paragraph, washed once with the incubation buffer and resuspended in 1 ml of 1×FACSlyse in water (Becton Dickinson) for 30 min at room temperature, to permeabilize the cell membranes. The cells were then spun down, washed with the incubation buffer and incubated for 1 h at 37° C. with 4 µg/ml of a fluorescein isothiocyanate (FITC)-labeled mouse anti-HA mAb (BabCo, Richmond, Calif.) for intracellular labeling. Finally, cells were washed once with binding buffer and once with DPBS, resuspended in 1% formaldehyde in PBS and analyzed by flow cytometry. The extent of binding of a mAb to mutant CCR5 was determined by the equation (mutant CCR5 PE m.f.i./wt CCR5 PE m.f.i.)/(mutant CCR5 FITC m.f.i./wt CCR5 FITC m.f.i.)× 100%. This normalizes mAb binding for mutant coreceptor expression levels.

gp120/sCD4-binding assay gp120 was biotinylated using NHS-biotin (Pierce, Rockford, Ill.) according to the manufacturer's instructions, and uncoupled biotin was removed by diafiltration. Sodium butyrate-treated L1.2-CCR5$^+$ cells were incubated with varying dilutions of an equimolar mixture of sCD4 and biotinylated gp120, or 1.25 µg/ml of sCD4 and 2.5 µg/ml of biotinylated gp120 in the presence of varying concentrations of anti-CCR5 mAbs PA8-PA12, PA14, 2D7 or a non-specific murine IgG1, for 1 h at room temperature in 0.1% NaN$_3$ in DPBS. Cells were washed with the incubation buffer and incubated with streptavidin-PE (Becton Dickinson) diluted 1:50, for 1 h at room temperature. Finally, cells were washed with binding buffer and analyzed using a fluorescence plate reader (Perspective Biosystems, Framingham, Mass.).

Inhibition of envelope-mediated cell-cell fusion and HIV-1 entry by anti-CCR5 mabs HIV-1 envelope-mediated fusion between HeLa-Env$_{JR-FL}$$^+$ and PM1 cells was detected using the RET assay. Equal numbers ($2\times10^4$) of fluorescein octadecyl ester (F18)-labeled envelope-expressing cells and octadecyl rhodamine (R18)-labeled PM1 cells were plated in 96-well plates in 15% fetal calf serum in DPBS and incubated for 4 h at 37° C. in the presence of varying concentrations of the anti-CCR5 mabs, PA8-PA12, PA14, 2D7 or a non-specific murine IgG1. Fluorescence RET was measured with a Cytofluor plate-reader (PerSeptive Biosystems) and % RET was determined as previously described (38).

NLluc$^+$env$^-$ viruses complemented in trans by envelope glycoproteins from JR-FL or Gun-1 were produced as previously described (20). U87MG-CD4$^+$CCR5$^+$ cells (14)

were infected with chimeric, reporter viruses containing 50-100 ng/ml p24 in the presence of varying concentrations of the individual mabs. After 2 h at 37° C., virus-containing media were replaced by fresh, mAb-containing media. Fresh media, without antibodies, were added again after 12 hours. After a total of 72 h, 100 µl of lysis buffer (Promega) were added to the cells and luciferase activity (r.l.u.) was measured as described (20). The % inhibition of HIV-1 infection is defined as [1−(r.l.u in the presence of antibody/r.l.u in the absence of antibody)]×100%.

Calcium signaling assays

The fluorochrome Indo-1AM (Molecular Probes, Eugene, Oreg.) was added to sodium butyrate treated L1.2-CCR5$^+$ cells at a final concentration of 5 µM. After incubation at 37° C. for 30 min, the cells were washed once and resuspended in Hank's buffered saline. Cells ($10^6$) were stimulated sequentially with an anti-CCR5 mAb or PBS, followed 60 s later with PANTES. MAbs PA8-PA12 and PA14 were used at a concentration of 100 µg/ml, 2D7 at 20 µg/ml and RANTES at 250 ng/ml. Calcium flux inhibition by PA14 and 2D7 was also tested for a wide range of mAb concentrations, ranging from 0-100 µg/ml. Intracellular calcium levels were monitored using a Perkin-Elmer LS-50S fluorescence spectrophotometer by measuring the ratio of fluorescence emissions at 402 nm (bound dye) and 486 nm (free dye) following excitation at 358 nm.

B. Results and Discussion

Isolating anti-CCR5 monoclonal antibodies PA8 PA9, PA10, PA11, PA12 and PA14

It was found that peptides corresponding to the extracellular domains of CCR5 are inefficient at raising specific, high-titer antibody responses against the native, cell surface receptor (50). Balb/C mice were immunized, therefore, with L1.2-CCR5$^+$ cells and hybridoma culture supernatants were tested for their ability to inhibit JR-FL envelope-mediated membrane fusion with CD4$^+$CCR5$^+$ PM1 cells in the RET assay (19, 38). Even though well over a hundred supernatants inhibited cell-cell fusion by >50%, only six - designated PA8, PA9, PA10, PA11, PA12 and PA14- specifically and intensely stained L1.2-CCR5$^+$ but not the parental L1.2 cells, as demonstrated by flow cytometry (data not shown). Based on previous experience, it was assumed that the other mAbs capable of inhibiting cell-cell fusion were probably directed against cell surface adhesion molecules such as LFA-1 (37). Hybridomas PA8-PA12 and PA14 were determined by isotyping ELISA (Cappell, Durham, N.C.) to secrete IgG1 mAbs. Ascites fluids were prepared from Balb/C mice that were injected with the six hybridomas and the IgG1 fractions were purified. PA8, PA9, PA11, PA12 and PA14 exhibited distinct isoelectric focussing profiles, whereas PA10 had a very similar profile to that of PA9 and therefore may be a second isolate of the same mAb (data not shown).

MAb binding to CCR5$^+$ cells

None of the purified anti-CCR5 mabs stained the parental L1.2 cell line (data not shown). However, mabs PA9 -PA12 and PA14 stained >90%, and PA8 stained ~70%, of L1.2-CCR5$^+$ cells as determined by flow cytometry, showing they recognized CCR5 (FIG. 1). The anti-CCR5 mAb 2D7, which was a positive control in our experiments, also stained >90% of L1.2-CCR5$^+$ cells. PA8-PA12 and PA14 are all IgG1, and react equally well with a goat anti-mouse IgG, whereas 2D7 is an IgG2a and may react differently with the reporter antibody. Only mean fluorescence intensities (m.f.i.) measured with mabs PA8-PA12 and PA14 therefore are directly comparable. The rank order of mean fluorescence intensities (m.f.i.) was PA12~PA11>(2D7=) PA14~PA10~PA9>PA8. The difference between PA12 m.f.i. and PA8 m.f.i. was three-fold. Differences in staining intensity between PA8 and the other mabs remained constant over a wide range of concentrations (data not shown) and probably do not correspond to differences in mAb affinities for CCR5. This implies that PA8 interacts only with a subset of CCR5 molecules present on the surface of L1.2-CCR5$^+$ cells.

Compared with L1.2-CCR5$^+$ cells, mitogen-stimulated PBMC exhibited different patterns of staining by the anti-CCR5 mAbs. 2D7 and PA14 stained >20%, PA11 and PA12 stained ~10%, PA8, PA9 and PA10 stained <5% of PBMC (FIG. 1). The mean fluorescence intensities of the stained PBMC were about ten-fold lower than those obtained with L1.2-CCR5$^+$ cells for each mAb; their rank order was (2D7>) PA14>PA12~PA11~PA10~PA9~PA8. Again, this differed somewhat from the order of reactivities observed on CCR5 transfectants. The difference between PA9 m.f.i. and PA14 m.f.i. was seven-fold. Other groups have observed similar differences in the ability of anti-CCR5 mAbs to stain stable, CCR5$^+$ cell lines versus PBMC (28). This may be due to cell-specific differences in CCR5 conformation, post-translational modification or oligomerization. Alternatively, association with other cell surface molecules may differ between cells. Since an obvious choice for such a molecule would be the CD4 cell surface antigen, which is absent from L1.2-CCR5$^+$ cells and present on PBMCs, we also tested the ability PA8-PA12, PA14 and 2D7 to stain HeLa cells transiently expressing CCR5 alone or with CD4. No differences were observed in the ability of any of the mabs to stain cell surface CCR5 in the presence of CD4 (data not shown). If there is an association between these two proteins, it does not involve epitopes recognized by the anti-CCR5 mAbs available to us. Alternatively, an association between CCR5 and CD4 might only occur on primary lymphocytes.

Epitope mapping of the mabs using CCR5 alanine mutants

Figure 4:
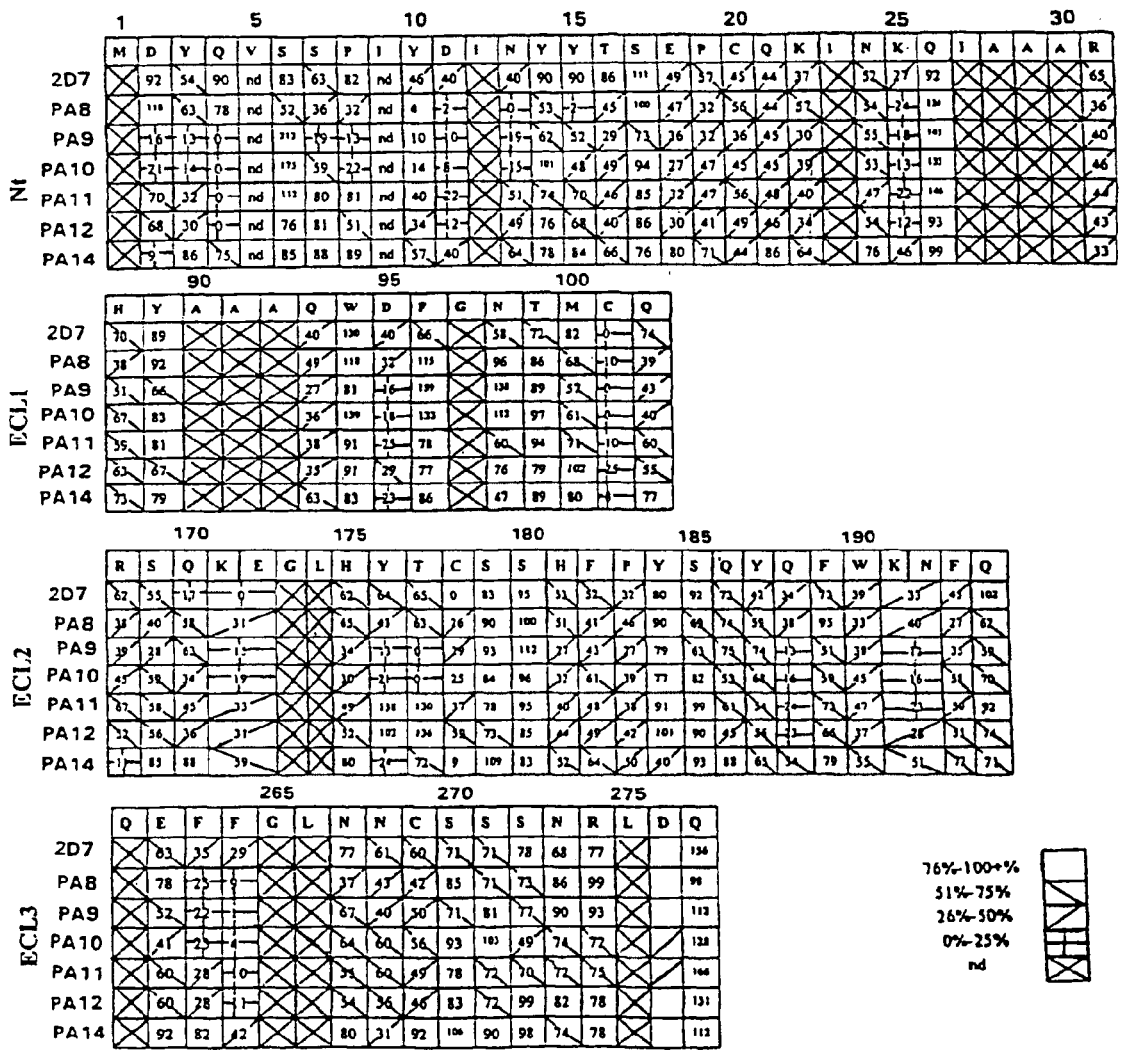

None of the antibodies were able to detect reduced and denatured CCR5 protein by Western blotting indicating that they recognize conformationally sensitive epitopes (data not shown). MAb epitope mapping studies were performed using a panel of seventy alanine point mutants of residues in the Nt and ECLs of CCR5. HeLa cells were lipofected with mutant or wild type CCR5 coding sequences appended with C-terminal HA tags, and infected with vTF7 (23) to boost co-receptor expression. The cells were then incubated with the anti-CCR5 mAbs and their binding was revealed by a PE-labeled goat anti-mouse IgG. A second, intracellular stain was performed with a FITC-labeled anti-HA mAb (BabCo). This internal control allowed us to directly normalize staining by the anti-CCR5 mAbs for mutant co-receptor expression levels on the cell surface. Hence, mAb binding to each mutant is expressed as a percentage of binding to wild-type CCR5 (FIG. 4).

Certain point mutations reduced the binding of all of the antibodies to CCR5 by >50%. In general, PA8-PA12 were the most affected, PA14 and 2D7 the least affected by this class of mutants, which included the cysteine pair C101A and C178A, the Nt mutants Y10A, D11A, K25A, the ECL1 mutant D95A, the ECL2 mutants K171A/E172A, Q188A, K191A/N192A, and the ECL3 mutants F263A and F264A (FIG. 4). One interpretation is that these residues are not part of the mAb epitopes per se, but that changing them to alanines causes conformational perturbations that have a common effect on binding of all mabs. We assumed that if a mutation lowered binding of an individual mAb by >75%, and did not also lower binding of most of the other antibodies, the residue was probably a direct contributor to the epitope recognized by the mAb. Using these stringent guidelines, it was concluded that the seven anti-CCR5 mAbs recognize overlapping but distinct epitopes (FIG. 4). MAb PA8 binding to CCR5 depended on N13 and Y15 in the Nt. MAb PA9 and PA10 required D2, Y3, Q4, P8 and N13 in the Nt, and Y176 and T177 in ECL2. MAb PA9 also required S7 in the Nt. MAb PA11 and PA12 binding depended on Q4 in the Nt. PA14 required D2 in the Nt, and R168 and Y176 in ECL2. Finally, mAb 2D7 required Q170 and K171/E172 in ECL2 in order to bind to CCR5.

Chemokine signaling in the presence of anti-CCR5 mAbs

Figure 5A:
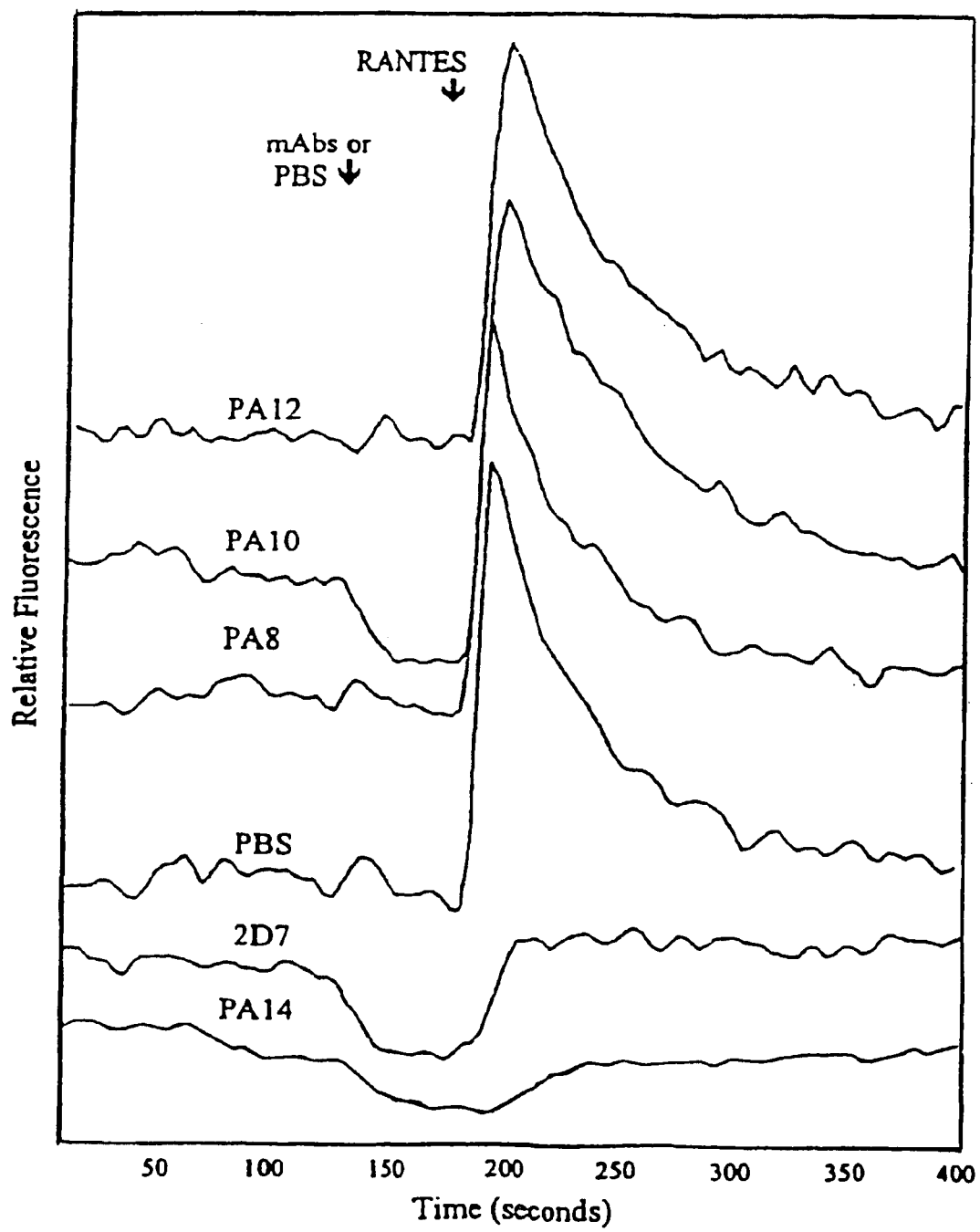
Figure 5B:
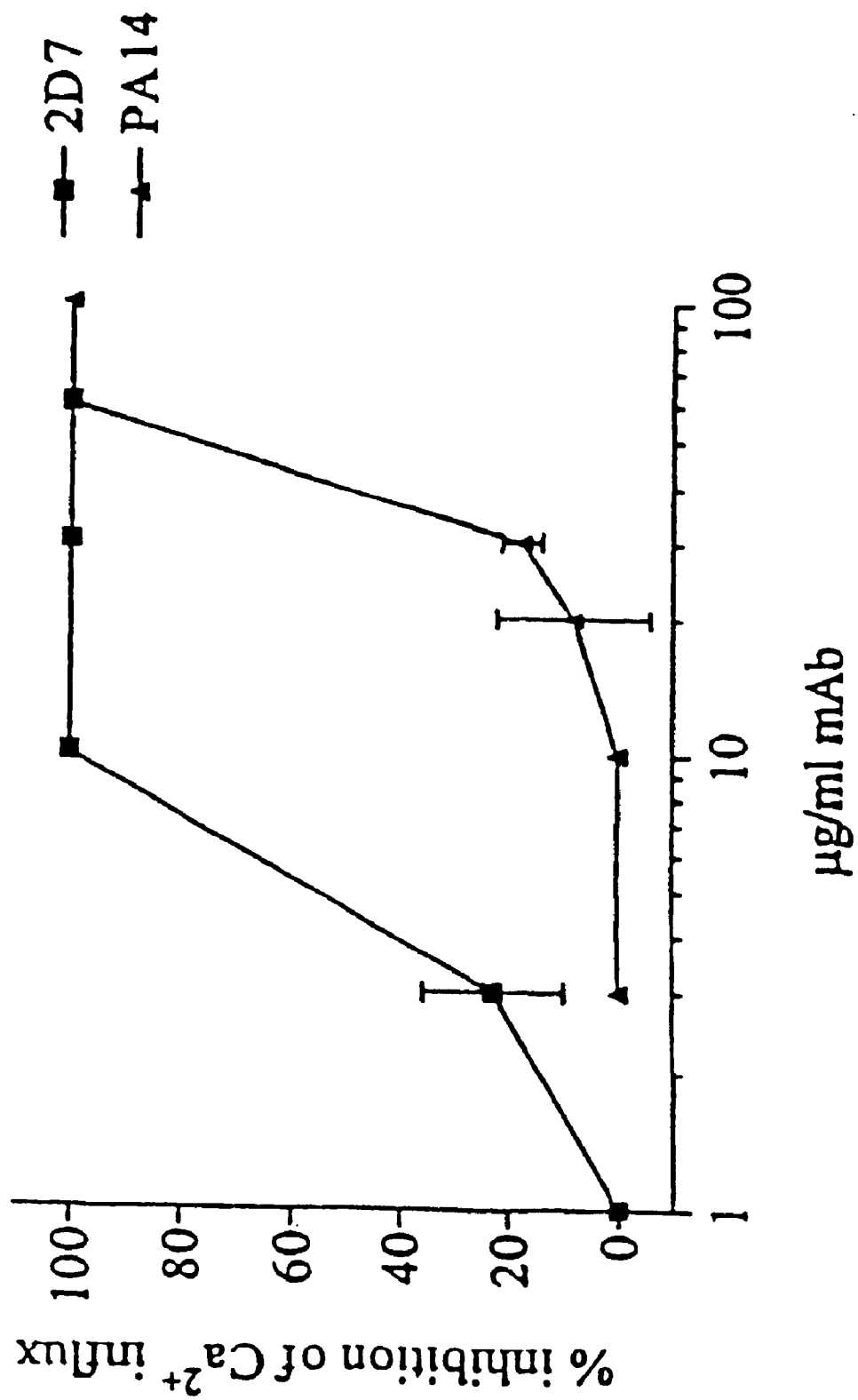

Chemokine receptor-binding agents can be antagonists or, more rarely, agonists of receptor-mediated intracellular signaling. Alternatively, they could have no effect on signaling. CCR5 is able to bind three CC-chemokines, RANTES, MIP-1α and MIP-1β, and transduce a signal that modulates cytosolic calcium levels. We therefore tested the agonist/antagonist activity of various concentrations of mAbs PA8-PA12, PA14 and 2D7. Changes in intracellular calcium concentrations, $(Ca^{2+})i$, were measured in Indo-1-loaded L1.2-CCR5$^+$ cells. None of the mAbs stimulated a change in $(Ca^{2+})i$, indicating that they are not agonists for CCR5. PA8-PA12 were also unable to inhibit $Ca^{2+}$ fluxes induced by RANTES (FIG. 5a and data not shown), even at concentrations as high as 100 μg/ml, showing they are not antagonists either. These concentrations provide saturating binding of the mAbs to L1.2-CCR5$^+$ cells, as shown by flow cytometry and the gp120/CCR5 binding assay (FIG. 3d and data not shown). MAbs PA14 and 2D7, however, blocked calcium mobilization induced by RANTES, although with different potencies (FIG. 5a, b). The IC$_{50}$ for PA14 calcium influx inhibition was 50 μg/ml, which was approximately 8-fold higher than the IC$_{50}$ for 2D7 (FIG. 5b). RANTES-, MIP-1α- and MIP-1β-induced calcium fluxes were each inhibited by similar concentrations of PA14 (data not shown). None of the mAbs affected SDF-1-induced calcium mobilization in L1.2-CCR5$^+$ cells, which endogenously express CXCR4 (data not shown). Finally, neither mabs nor CC-chemokines affected cytosolic calcium levels in parental L1.2 cells (data not shown).

Inhibition of CCR5 co-receptor function by the mabs

Figure 6A:
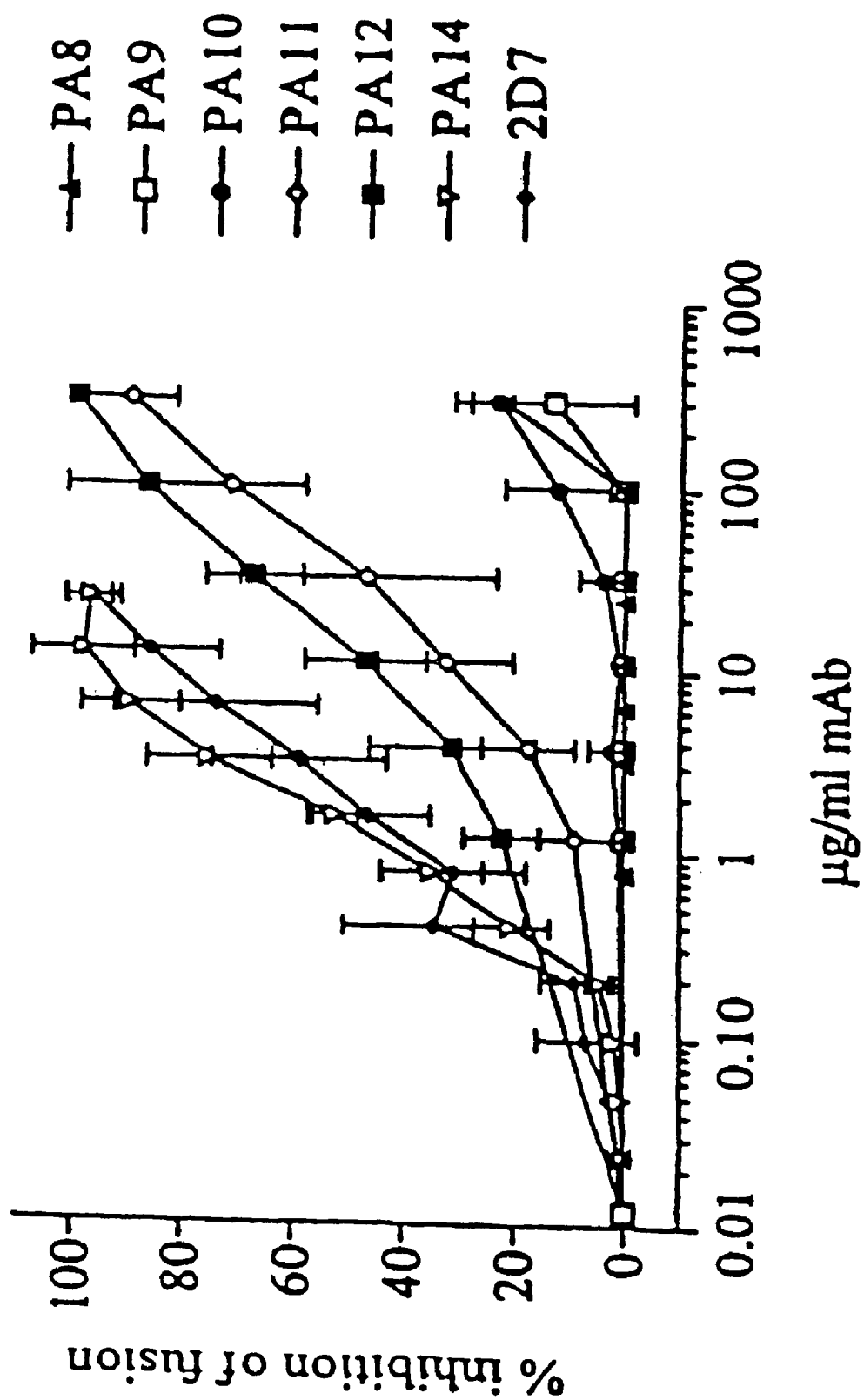
Figure 6B:
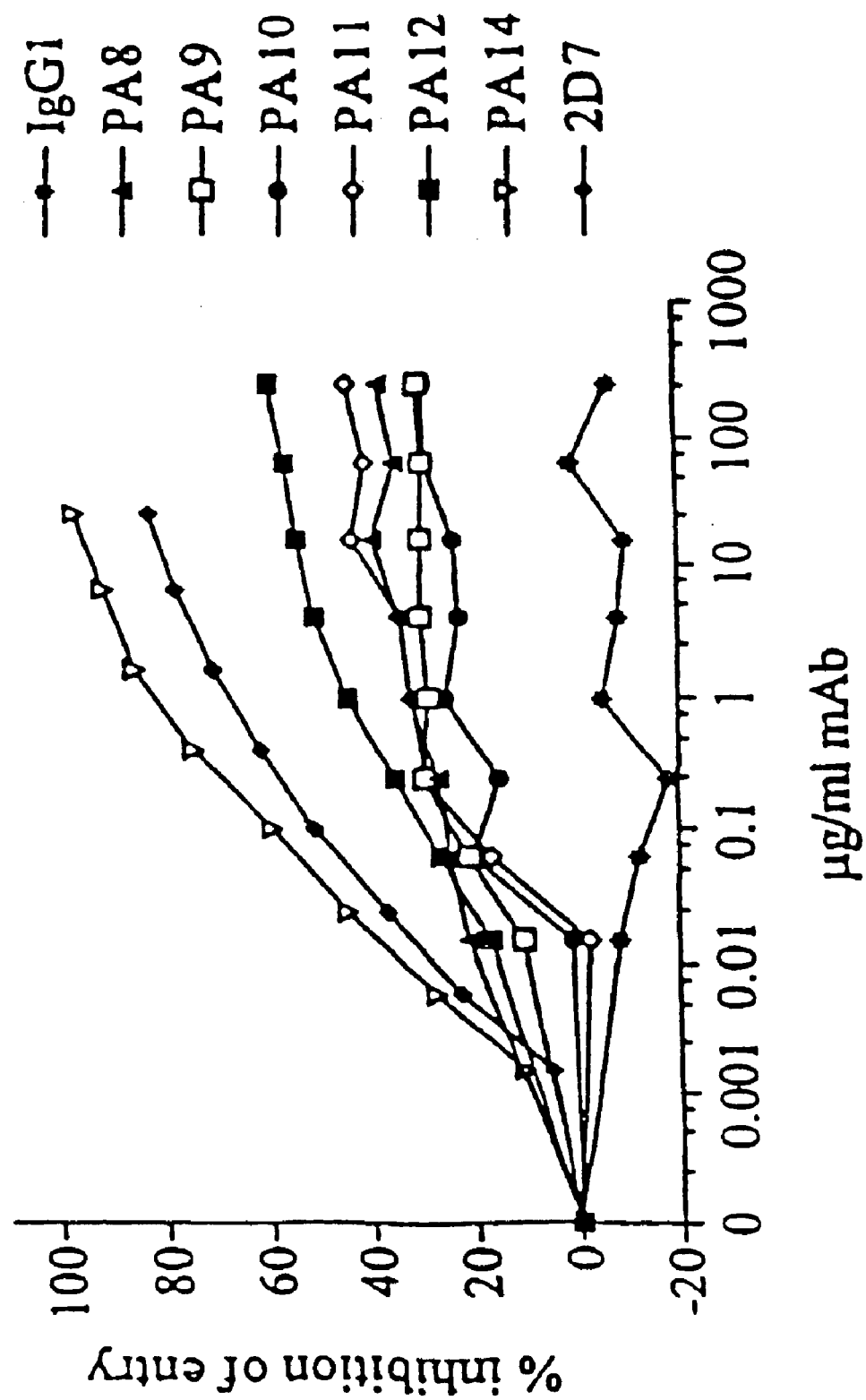

MAbs PA8-PA12 and PA14 were initially selected on the basis of their ability to inhibit HIV-1 envelope-mediated cell-cell fusion. This activity was confirmed and quantified for the purified mabs. As expected, all six mAbs, as well as mAb 2D7, blocked fusion between CD4$^+$CCR5$^+$ PM1 cells and HeLa-Env$_{JR-FL}$$^+$ cells in the RET assay. The rank order of potency was 2D7~PA14>PA12>PA11>PA10~PA9~PA8 (FIG. 6a). IC$_{50}$ values for PA14 and 2D7 were 1.7 μg/ml and 1.6 μg/ml respectively, for PA11 and PA12 these were 25.5 μg/ml and 10.0 μg/ml respectively (FIG. 3). PA8, PA9 and PA10 inhibited fusion by only 10-15% at 300 μg/ml. None of the mabs affected fusion between PM1 cells and HeLa-Env$_{LAI}$$^+$ cells, which express the full length envelope protein from an X4 virus (data not shown).

The ability of the different anti-CCR5 mabs to inhibit entry of a prototypic R5 virus, JR-FL, and a R5 X4 virus, Gun-1, in a single-round of replication, luciferase-based entry assay was also tested. The rank order of potency in the entry assay was similar to the one determined in the cell-cell fusion assay (FIG. 3b). A >50% inhibition of JR-FL or Gun-1 entry with PA8-PA11 was unable to be obtained. The IC$_{50}$ value for PA12 was 2.5 μg/ml. However, inhibition of entry by >60% with this mAb was unable to be obtained. The IC$_{50}$ values for PA14 and 2D7 inhibition of JR-FL entry were determined to be 0.024 and 0.026 μg/ml respectively (Table 3), and were 60-fold lower then those obtained in the fusion assay. Entry of dual-tropic Gun-1 was 2-3-fold more sensitive to inhibition by anti-CCR5 mabs than JR-FL entry (data not shown).

Figure 6C:
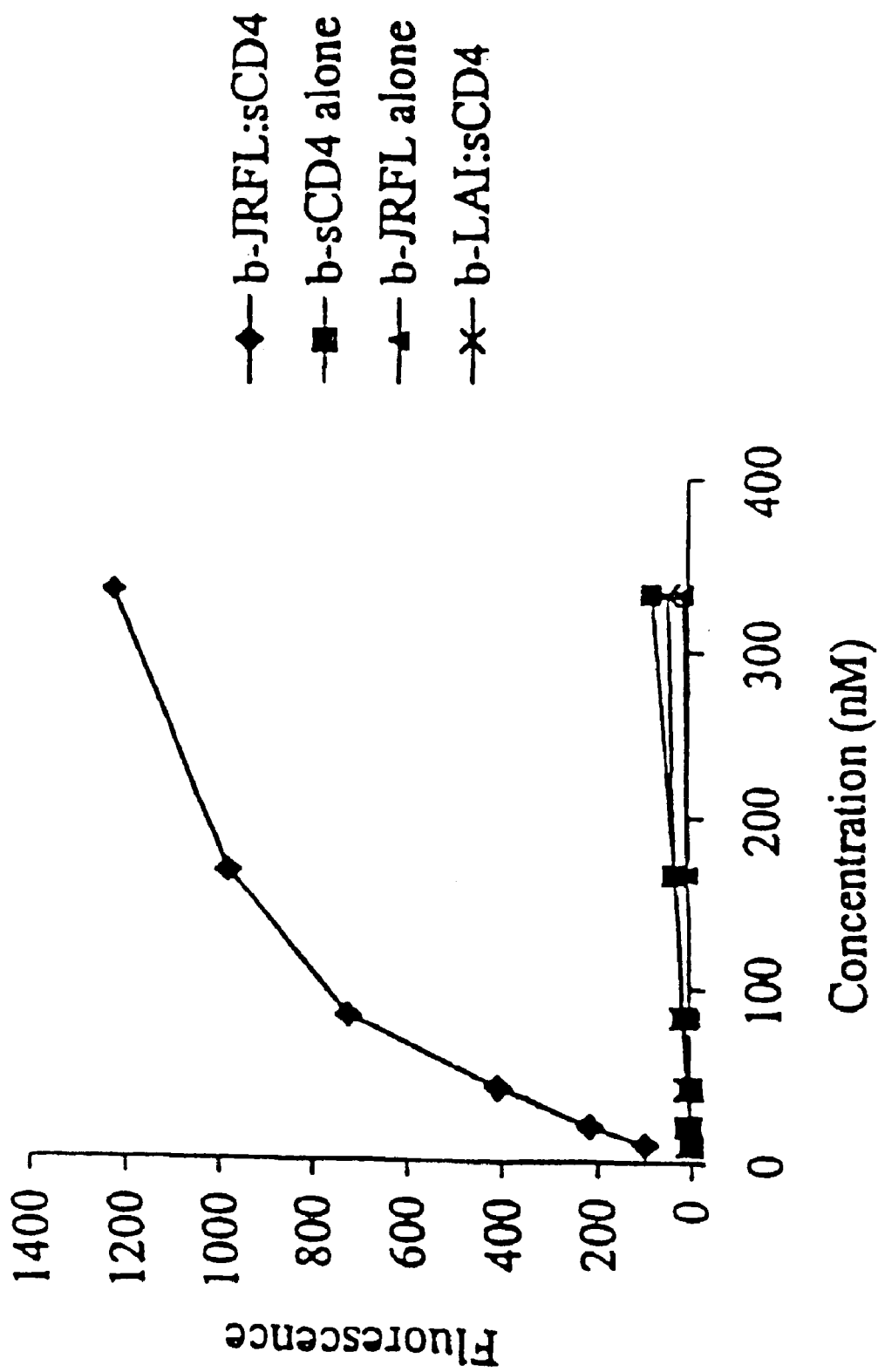

Anti-co-receptor mabs might inhibit envelope-mediated fusion either by directly affecting the gp120/CCR5 interaction or by impeding post-binding steps involved in the formation of an active fusion complex. To determine the mechanism of inhibition of viral fusion and entry by PA8-PA12 and PA14, the ability of the different mAbs to block the gp120/CCR5 interaction was tested. For this an assay that detects binding to L1.2-CCR5$^+$ cells of biotinylated HIV-1$_{JR-FL}$ gp120 complexed with sCD4 was used. No binding of biotinylated gp120 was observed in the absence of sCD4 or CCR5, or when HIV-1$_{LAI}$ gp120 was used (FIG. 6c).

Figure 6D:
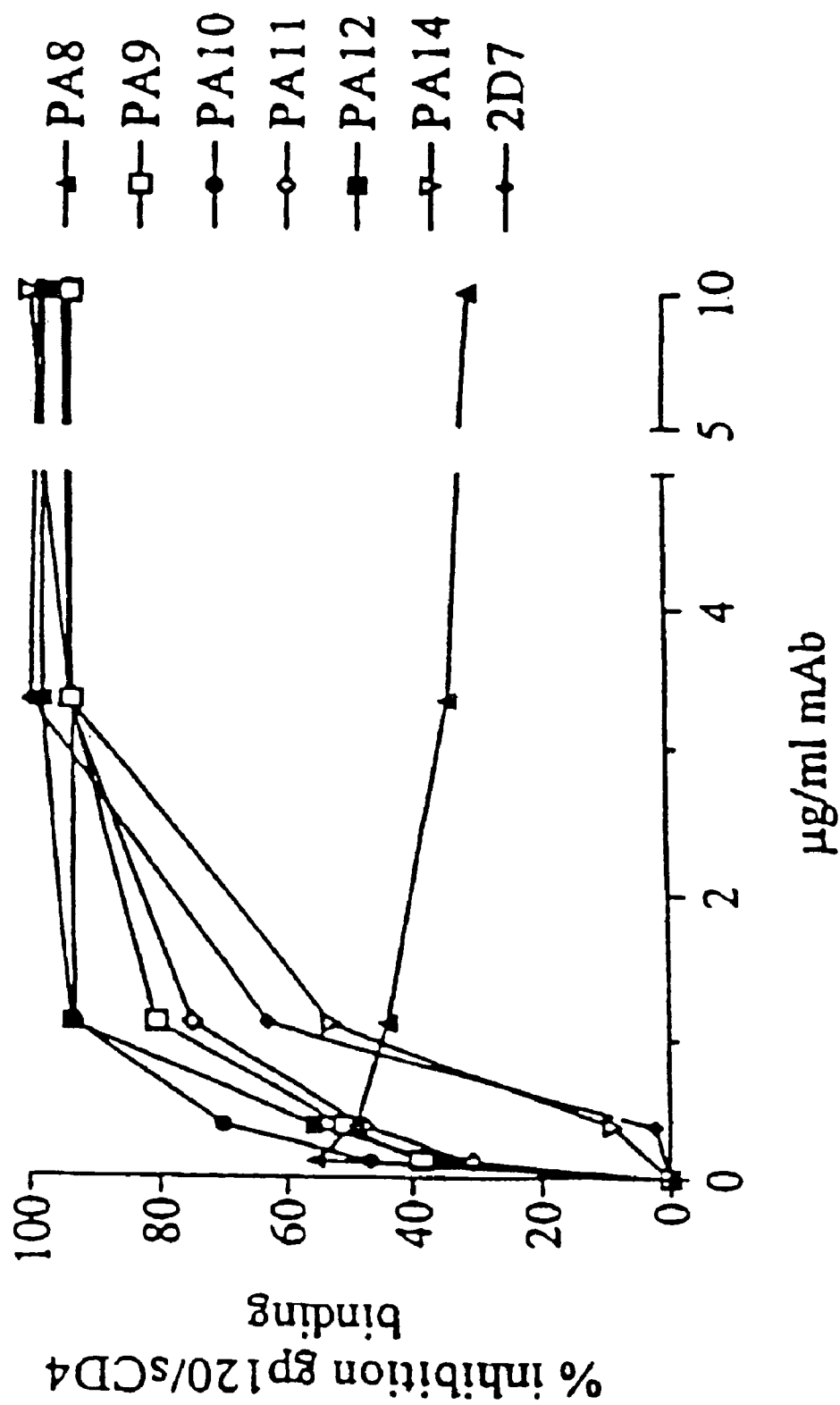

With the exception of PA8, all mabs abrogated gp120/sCD4 binding to L1.2-CCR5$^+$ (FIG. 6d). Inhibition by PA8 saturated at ~40%, which concurs with flow cytometry data (FIG. 1) in suggesting that this mAb binds only to a subset of CCR5 molecules on L1.2-CCR5$^+$ cells. MAbs PA9, PA10, PA11 and PA12 inhibited binding with IC$_{50}$ values of 0.24, 0.13, 0.33, 0.24 μg/ml respectively (FIG. 3). Surprisingly, mAbs PA14 and 2D7 were the two least efficient inhibitors of gp120/sCD4 binding, with IC$_{50}$ values of 1.58 and 1.38 μg/ml respectively (FIG. 3). Therefore, there was no correlation between the ability of a mAb to inhibit gp120/CD4/CCR5-mediated membrane fusion and entry and its ability to block gp120/sCD4 binding to the co-receptor.

Synergistic inhibition of HIV-1 fusion by combinations of anti-CCR5 mabs and other viral entry inhibitors Co-receptor-specific agents may act at multiple stages of the entry process and exhibit non-additive effects when used in combination. From a clinical perspective, it is important to determine the interactions of co-receptor-specific drug candidates with endogenous chemokines, which may afford some level of protection against disease progression. CCR5 mAbs were therefore tested in combination with each other or with RANTES, or with CD4-IgG2, which binds to HIV-1 gp120 to inhibit attachment to target cells. Dose-response curves were obtained for the agents used individually and in combination in viral fusion and entry assays. Data were analyzed using the median effect principle (9). The concentrations of single-agents or their mixtures required to produce a given effect were quantitatively compared in a term known as the Combination Index (CI). A CI value greater than 1 indicates antagonism, CI~1 indicates an additive effect, and CI<1 indicates a synergistic effect wherein the presence of one agent enhances the effect of another.

Combinations of PA12 and 2D7 were the most potently synergistic, with CI values ranging between 0.02 and 0.29, depending on the ratio of the antibodies (FIG. 7 and FIG. 2). The degree of synergy is known to vary with the stoichiometry of the agents. The viral entry and fusion assays were generally consistent in identifying mAb combinations that are highly synergistic, PA12 and 2D7; moderately synergistic, PA12 and PA14; additive, PA11 and PA12; and weakly antagonistic, PA14 and 2D7. The lack of synergy between PA14 and 2D7 is not surprising given that these mAbs cross-compete for binding to CCR5$^+$ cells as determined by flow cytometry (data not shown). The observation of an additive effect of PA11 and PA12 may be an indication that these mAbs bind to slightly different epitopes in CCR5, while sharing a dependency on residue Q4 in the Nt.

The ability of mAbs PA12, PA14 and 2D7 to synergize with RANTES in blocking cell-cell fusion was also tested. PA12 and RANTES combinations exhibited moderate synergy (FIG. 2). PA14 and 2D7 exhibited no synergy with RANTES, which is consistent with these mabs being inhibitory of RANTES binding and signaling (FIG. 5a, b). Finally, we tested synergy between mabs PA12, PA14, 2D7 and CD4-IgG2, which interacts with gp120. We observed moderate synergy between PA12 and CD4-IgG2 but no synergy between PA14 or 2D7 and CD4-IgG2 (FIG. 2).

Experimental Discussion

Six murine anti-CCR5 IgG1 mAbs were isolated and characterized. Whereas PA8, PA9, PA11, PA12 and PA14 are distinct molecular species, PA9 and PA10 are indistinguishable by the analyses and therefore are probably the same mAb. All of the mabs that were isolated recognize complex conformational epitopes, as is often the case with mabs raised against native, cell surface proteins. Epitope mapping was performed for all mabs using a panel of CCR5 alanine point mutants. Residues that affected binding of all mAbs similarly were assumed to cause conformational perturbations in the co-receptor and not to constitute part of the mAb epitopes. Only two such residues, Y10 and D11, have been shown to affect HIV-1 entry (20, 52). The PA8, PA11 and PA12 epitopes are located exclusively in the Nt domain. Consistent with this result, PA8 was able to bind a biotinylated Nt peptide, containing residues D2 through R31, in an ELISA (data not shown). However, PA11 and PA12, whose binding strongly depended only on Q4, did not bind the Nt peptide in solution (data not shown). One possibility is that the Nt peptide does not assume the proper conformation for recognition by PA11 and PA12, whereas PA8 binding may be less conformation-dependent. Alternatively, PA11 and PA12 might interact with residues that we have not mutated, or form weak bonds with amino acids located in other domains of CCR5, or bind peptide backbone atoms whose presentation may be unchanged by mutagenesis. Antibodies PA9, PA10 and PA14 recognized epitopes that included residues in both the Nt and ECL2 domains of CCR5, whereas the 2D7 epitope was located exclusively in ECL2.

The PA14 epitope comprises both D2 in the Nt and R168 in ECL2 indicating that these two residues are proximal to one another within the context of a mAb footprint. They may even directly interact with one another through their opposite charges.

MAbs PA8-PA12 and PA14 stained CCR5+ cells with different intensities and in a cell type-dependent manner. All mAbs except PA8 stained >90% L1.2-CCR5+ cells, the highest mean fluorescence intensity being observed with PA11 and PA12. However, PA14 and 2D7 stained the highest percentage of PBMC and also yielded the highest mean fluorescence intensities on these cells. Hill et al. (28) have recently characterized a panel of anti-CCR5 mabs that similarly stained transfected cells, but only two of eight stained PBMC, and none stained primary monocytes. A low affinity for CCR5 probably accounted for the nonreactivity of two of the mAbs with primary cells, but this was unlikely to be the explanation for the failure of the other four to react. In our mAb panel, we observe the most intense staining of PBMC by mabs 2D7 and PA14 that have epitopes located entirely or partially in the first ten residues of ECL2. Hill et al. report, however, that mAbs specific for the Nt and ECL1 stain PBMCs, while mabs to ECL2 and ECL3 do not stain PBMC, so a consistent pattern of reactivity has not been identified. One explanation for cell type-specific staining by mabs would be that activated PBMCs (and monocytes) secrete CC-chemokines that bind to cell surface CCR5, masking some mAb epitopes. However, one would expect this to be especially true for PA14 and 2D7, which are antagonists of chemokine-induced calcium mobilization and presumably compete with CC-chemokines for binding to CCR5. Yet these rnAbs stain PBMC the most intensely. Alternatively, differential CCR5 epitope exposure may reflect cell type-specific receptor oligomerization, association with other cell-surface molecules, or different post-translational modifications such as glycosylation. We have shown that differences in mAb binding probably do not reflect cell type-specific differences in CD4/CCR5 interactions.

MAbs PA8-PA12 did not inhibit CC-chemokine induced calcium mobilization in CCR5+ cells, nor did they mediate signaling through CCR5. MAbs 2D7 and PA14 were inhibitors of CC-chemokine induced calcium mobilization, but 2D7 was almost an order of magnitude more potent than PA14. This may be because the PA14 epitope overlaps less with the CC-chemokine binding domain on CCR5 than the 2D7 epitope. All of the mAbs also blocked HIV-1 entry and envelope-mediated membrane fusion, but inhibition of cell-cell fusion required in some cases almost two orders of magnitude more antibody than what was needed to block viral entry. Presumably, more gp120/CD4/CCR5 interactions as well as interactions between adhesion molecules are established and act cooperatively during cell-cell fusion, compared to virus-cell fusion, making it more difficult to inhibit. This is commonly observed with antibodies to LFA-1 or to the HIV-1 envelope glycoprotein (45, 51). PA8, PA9 and PA10 were unable to block cell-cell fusion by >15% and viral entry by >40%, even at the highest antibody concentrations. However, >90% inhibition of fusion could be attained with PA11, PA12 and PA14, and >90% inhibition of entry could be attained with PA14. The most potent of the six mabs in blocking fusion and entry was PA14, which was as effective as 2D7. Surprisingly, PA14 and 2D7 were among the least potent inhibitors of gp120/sCD4 binding to L1.2-CCR5+ cells, whereas PA9-PA12 blocked with similar potencies, and PAS was unable to block >40% of gp120/sCD4 binding. These observations raise questions about the nature of the CCR5 molecules presented on different cells and about the mechanisms of inhibition of viral fusion and entry. It may be that CCR5 on L1.2 cells, used in the mAb and gp120-binding assays, is not in an identical conformation to CCR5 on PBMC, used in the mAb-binding assay, or to CCR5 on PM1 and U87MG cells used in the fusion and entry assays.

The low staining of PBMC and the partial inhibition of fusion and entry by some of our mAbs indicate that they are only able to bind to a subset of CCR5 molecules expressed on primary lymphocytes, PM1 and U87MG-CD4+CCR5+ cell lines. Yet, other than PA8, all mAbs are able to stain >90% L1.2-CCR5+ cells and to completely block binding of the gp120/sCD4 complex to these cells. At least one difference between L1.2-CCR5+ and the other cells that we have used is the density of co-receptor protein on the cell surface. Indeed, we estimate that the L1.2-CCR5+ cells express 10- to 100-fold more cell surface co-receptor than PM1 and U87MG-CD4+CCR5+ cells. But when HeLa cells are engineered to transiently express as much co-receptor as the L1.2-CCR5+ cell line, we are still unable to detect gp120/sCD4 binding to them (data not shown). Over-expression of CCR5 on L1.2, along with other cell-specific factors therefore, might favor a co-receptor conformation that prominently exposes the Nt, making it more accessible to both mAbs and gp120. Such a conformation might be induced by receptor oligomerization, by diminished or altered associations with cell surface proteins or by receptor interactions with G proteins (25, 62). Do multiple conformations of CCR5 co-exist on the cell surface, and are they all permissive for viral entry? The patterns of mAb reactivity would suggest so, since HIV-1 entry and fusion can occur, albeit at reduced levels, in the presence of mAb concentrations that saturate epitopes required for gp120 binding to L1.2-CCR5$^+$ cells. We favor the hypothesis that the co-receptor molecules present on L1.2-CCR5$^+$ cells possess one HIV-1 entry-competent conformation whereas CCR5 molecules on PBMC, PM1 and CCR5$^+$ U87MG exist in multiple, entry-competent states that display different mAb reactivities. Whereas PA14 and 2D7 may recognize all conformations, other mabs may not. Why L1.2 cells are conducive to a particular fusion-competent conformation remains to be determined.

It has recently been demonstrated that the gp120-binding domain lies in the first twenty residues of the CCR5 Nt domain. MAbs to the gp120-binding domain on CCR5 potently block this interaction but are not nearly as efficient at inhibiting HIV-1 fusion and entry into target cells as PA14 and 2D7, whose epitopes lie outside this region. PA14 recognizes the tip of the Nt and residues in ECL2, whereas the 2D7 epitope is located exclusively in ECL2. At the mechanism of action of these mAbs can only be speculated. It may be that their binding to the first few residues of ECL2 induces conformational changes in the co-receptor that prevent membrane fusion. Alternatively, obstruction of ECL2 epitopes might impede co-receptor oligomerization and the formation of a fusion-competent protein complex. Yet another possibility is that residues in ECL2 face the inside of the fusion pore and binding of the mabs impedes gp4i from inserting the fusion peptide into the plasma membrane. In contrast, mAbs PA8-PA12 probably inhibit fusion and entry only by directly competing for binding with gp120/CD4 complexes. We do not know if parameters other than epitope exposure and affinity for CCR5 determine the efficacy of viral entry inhibition by these mAbs. It is unclear why inhibiting steps subsequent to the gp120/co-receptor interaction would be more efficient than directly blocking that interaction. One way to explain this would be to assume that the off rate of gp120 binding to CCR5 is much lower than the on rate of mAb binding to CCR5. Thus, every time a mAb detaches itself from a co-receptor molecule, a virion-associated gp120 molecule replaces it in a quasi-irreversible fashion since this interaction leads to membrane fusion.

Synergy between combinations of anti-CCR5 mAbs is probably a result of their interactions with distinct epitopes that are involved in inter-dependent, consecutive steps of HIV-1 entry. The degree of synergy observed between PA12 and 2D7 (CI<0.1 under many circumstances) is extraordinary since CI values <0.2 are rarely observed for combinations of anti-HIV-1 antibodies (33, 35, 61), reverse transcriptase inhibitors (29), or protease inhibitors (44). Because of its potency, the PA12:2D7 combination was examined in multiple assay formats and concentration ratios, for which consistently high levels of synergy were observed. Moderate synergy was observed for PA12 combined with PA14. We also observed moderate synergy between PA12 and CD4-IgG2. The CD4/gp120 complex is metastable and if it is unable to interact with a co-receptor, decays into a non-fusogenic state (45-48). Since PA12 directly blocks the gp120-binding site on CCR5, its presence may shift the equilibrium towards inactivation of the gp120/CD4 complex. This would explain why we observe synergy between CD4-IgG2 and mAb PA12 with respect to inhibition of fusion and entry. The lack of synergy between mAb PA14 and CD4-IgG2 suggests that they act on two non-consecutive and independent steps of viral entry. A combination of further studies will be needed to determine the precise mechanisms of synergy of the different compounds with respect to inhibition of viral fusion and entry.

The above results are consistent with a model wherein HIV-1 entry occurs in three distinct steps involving receptor binding, co-receptor binding, and co-receptor mediated membrane fusion. Separate co-receptor binding and fusion events are suggested by the lack of correlation between the monoclonal antibodies' abilities to block gp120 binding and HIV-1 fusion/entry. The chronology of events during fusion is further suggested by the patterns of synergies observed. Agents, such as PA12, that potently inhibit the middle step of the process, namely gp 120 binding, act synergistically with inhibitors of prior and subsequent steps.

REFERENCES FOR FIRST SERIES OF EXPERIMENTS

1. Allaway, G. P., K. L. Davis-Bruno, B. A. Beaudry, E. B. Garcia, E. L. Wong, A. M. Ryder, K. W. Hasel, M. C. Gauduin, R. A. Koup, J. S. McDougal and P. J. Maddon. 1995. Expression and characterization of CD4-IgG2, a novel heterotetramer that neutralizes primary HIV type 1 isolates. AIDS Res Hum Retroviruses 11: 533-539.
2. Allaway, G. P., A. M. Ryder, G. A. Beaudry and P. J. Maddon. 1993. Synergistic inhibition of HIV-1 envelope-mediated cell fusion by CD4-based molecules in combination with antibodies to gp120 or gp41. AIDS Res Hum Retroviruses 9: 581-587.
3. Amara, A., S. L. Gall, O. Schwartz, J. Salamero, M. Montes, P. Loetscher, M. Baggiolini, J. L. Virelizier and F. Arenzana-Seisdedos. 1997. HIV coreceptor downregulation as antiviral principle: SDF-1a-dependent internalization of the chemokine receptor CXCR4 contributes to inhibition of HIV replication. J. Exp. Med. 186: 139-146.
4. Berger, E. A. 1997. HIV entry and tropism: the chemokine receptor connection. AIDS 11 (suppl A) S3-S16.
5. Bieniasz, P. D. and B. R. Cullen. 1998. Chemokine receptors and human immunodeficiency virus infection. Frontiers in Bioscience 3: d44-58.
6. Bieniasz, P. D., R. A. Fridell, I. Aramori, S. S. G. Ferguson, M. C. Caron and B. R. Cullen. 1997. HIV-1 induced cell fusion is mediated by multiple regions within both the viral envelope and the CCR5 co-receptor. EMBO 16: 2599-2609.
7. Brelot, A., N. Heveker, O. Pleskoff, N. Sol and M. Alizon. 1997. Role of the first and third extracellular domains of CXCR4 in human immunodeficiency virus coreceptor activity. J. Virol. 71: 4744-4751.
8. Chan, D. C. and P. S. Kim. 1998. HIV entry and its inhibition. Cell 93: 681-684.
9. Chou, T. C. and D. C. Rideout. Synergism and antagonism in chemotherapy. New York: Academic Press, 1991
10. Cocchi, F., A. L. DeVico, A. Garzino-Demo, S. K. Arya, R. C. Gallo and P. Lusso. 1995. Identification of RANTES, MIP-1α and MIP-1β as the major HIV-suppressive factors produced by CD8 T-cells. Science 270: 1811-1815.
11. Connor, R. I., K. E. Sheridan, D. Ceradini, S. Choe and N. R. Landau. 1997. Change in co-receptor use correlates with disease progression in HIV-1 infected individuals. J. Exp. Med. 185: 621-628.
12. Crump, M. P., J. H. Gong, P. Loetscher, K. Rajarathnam, A. Amara, F. Arenzana-Seisdedos, J. L. Virelizier, M. Baggiolini, B. D. Sykes and I. Clark-Lewis. 1997. Solution structure and basis for functional activity of stromal-cell derived factor-1; disassociation of CXCR4 activation from binding and inhibition of HIV-1. EMBO 16: 6996-7007.

13. Dalgleish, A. G., P. C. L. Beverly, P. R. Clapham, D. H. Crawford, M. F. Greaves and R. A. Weiss. 1984. The CD4 (T4) antigen is an essential component of the receptor for the AIDS retrovirus. Nature 312: 763-766.

14. Deng, H. K., R. Liu, W. Ellmeier, S. Choe, D. Unutmaz, M. Burkhart, P. DiMarizio, S. Marmon, R. E. Sutton, C. M. Hill, S. C. Peiper, T. J. Schall, D. R. Littman and N. R. Landau. 1996. Identification of a major co-receptor for primary isolates of HIV-1. Nature 381: 661-666.

15. Dimitrov, D. S. 1997. How do viruses enter cells? The HIV Co-receptors teach us a lesson of complexity. Cell 91: 721-730.

16. Donzella, G. A., D. Schols, S. W. Lin, K. A. Nagashima, P. J. Maddon, G. P. Allaway, T. P. Sakmar, E. D. Clercq and J. P. Moore. 1998. JM3100, a small molecule that interacts with the CXCR4 co-receptor to prevent HIV-1 entry. Nat. Med. 4: 72-77.

17. Doranz, B. J., K. Grovit-Ferbas, M. P. Sharron, S. H. Mao, M. B. Goetz, E. S. Daar, R. W. Doms and W. A. O'Brien. 1997. A small molecule inhibitor directed against the chemokine receptor CXCR4 prevents its use as an HIV-1 co-receptor. J. Ex. Med. 186: 1395-1400.

18. Doranz, B. J., Z. -H. Lu, J. Rucker, T. -Y. Zhang, M. Sharron, Y. -H. Cen, Z. -X. Wang, H. -H. Guo, J. -G. Du, M. A. Accavitti, R. W. Doms and S. C. Peiper. 1997. Two distinct CCR5 domains can mediate co-receptor usage by human immunodeficiency virus type 1. J. Virol. 71: 6305-6314.

19. Dragic, T., V. Litwin, G. P. Allaway, S. R. Martin, Y. Huanh, K. A. Nagashima, C. Cayanan, P. J. Maddon, R. A. Koup, J. P. Moore and W. A. Paxton. 1996. HIV-1 entry into CD4+ cells is mediated by the chemokine receptor CC-CKR-5. Nature 381: 667-673.

20. Dragic, T., A. Trkola, X. W. Lin, K. A. Nagashima, F. Kajumo, L. Zhao, W. C. Olson, L. Wu, C. R. Mackay, G. P. Allaway, T. P. Sakmar, J. P. Moore and P. J. Maddon. 1998. Amino terminal substitutions in the CCR5 co-receptor impair gp120 binding and human immunodeficiency virus type 1 entry. J. Virol. 72: 279-285.

21. Dragic, T., A. Trkola and J. P. Moore. 1997. HIV coreceptors: Gateways to the cell. Advances in Research and Therapy 7: 2-13.

22. Farzan, M., H. Choe, L. Vaca, K. Martin, Y. Sun, E. Desjardins, N. Ruffing, L. Wu, R. Wyatt, N. Gerard, C. Gerard and J. Sodroski. 1998. A tyrosine-rich region in the N-terminus of CCR5 is important for human immunodeficiency virus type 1 entry and mediates an association between gp120 and CCR5. J. Virol. 72: 1160-1164.

23. Fuerst, T. R., E. G. Niles, F. W. Studier and B. Moss. 1986. Eukaryotic transient-expression system based on recombinant vaccinia virus that synthesizes bacteriophage T7 RNA polymerase. Proc. Natl. Acad. Sci. USA. 83: 8122-8126.

24. ;Genoud, S., F. Kajumo, Y. Guo, D. A. D. Thompson and T. Dragic. CCR5-mediated human immunodeficiency virus entry depends on an amino-terminal domain gp120-binding site and on the conformational integrity of all four extracellular domains. J. Virol. submitted.

25. Gether, U. and B. K. Kobilka. 1998. G protein-coupled receptors. J. Biol. Chem 273: 17979-17982.

26. Gordon, C., M. Muesing, A. E. I. Proudfoot, C. A. Power, J. P. Moore and A. Trkola. 1998. Enhancement of human immunodeficiency virus type 1 infection by the CC-chemokine RANTES is independent of the mechanism of virus-cell fusion. J. Virol. in press.

27. Heveker, N., M. Montes, L. Germeroth, A. Amara, A. Trautmann, M. Alizon and J. Schneider-Mergener. 1998. Dissociation of the signaling and antiviral properties of SDF-1-derived small peptides. Current Biology 8: 369-376.

28. Hill, C. M., D. Kwon, M. Jones, C. B. Davis, S. Marmon, B. L. Daugherty, J. A. DeMartino, M. S. Springer, D. Unutmaz and D. R. Littman. 1998. The amino terminus of human CCR5 is required for its function as a receptor for diverse human and simian immunodeficiency virus envelope glycoproteins. Virology 248: 357-371.

29. Johnson, V. A., D. P. Merrill, J. A. Videler, T. C. Chou, R. E. Byington, J. J. Eron, R. T. D'Aquila and M. S. Hirsch. 1991. Two-drug combinations of zidovudine, didanosine, and recombinant interferon-alpha A inhibit replication of zidovudine-resistant human immunodeficiency virus type 1 synergistically in vitro. J Infect Dis 164: 646-655.

30. Klatzmann, D., E. Champagne, S. Chamaret, J. M. Gruest, D. Guetard, T. Hercend, J. C. Gluckman and L. Montagnier. 1984. T-lymphocyte T4 molecule behaves as the receptor for human retrovirus LAV. Nature 312: 382-385.

31. Kuhmann, K. E., E. J. Platt, S. L. Kozak and D. Kabat. 1997. Polymorphism in the CCR5 genes of African green monkeys and mice implicate specific amino acids in infections by simian and human immunodeficiency viruses. J. Virol. 71: 8642-8656.

32. Kwong, P. D., R. Wyatt, J. Robinson, R. W. Sweet, J. Sodroski and W. A. Hendrickson. 1998. Structure of an HIV gp120 envelope glycoprotein in complex with the CD4 receptor and a neutralizing human antibody. Nature 393: 648-659.

33. Laal, S., S. Burda, M. K. Gorny, S. Karwowska, A. Buchbinder and S. Zolla-Pazner. 1994. Synergistic neutralization of human immunodeficiency virus type 1 by combinations of human monoclonal antibodies. J. Virol. 68: 4001-4008.

34. Labrosse, B., A. Brelot, N. Heveker, N. Sol, D. Schols, E. D. Clercq and M. Alizon. 1998. Determinants for sensitivity of human immunodeficiency virus co-receptor CXCR4 to the bicyclam AMD3100. J. Virol. 72: 6381-6388.

35. Li, A., H. Katinger, M. R. Posner, L. Cavacini, S. Zolla-Pazner, M. K. Gorny, J. Sodroski, T. C. Chou, T. W. Baba and R. M. Ruprecht. 1998. Synergistic neutralization of simian-human immunodeficiency virus SHIV-vpu+by triple and quadruple combinations of human monoclonal antibodies and high-titer anti-human immunodeficiency virus type 1 immunoglobulins. J. Virol. 72: 3235-3240.

36. Littman, D. R. 1998. Chemokine receptors: keys to AIDS pathogenesis. Cell 93: 677-680.

37. Litwin, V. unpublished results.

38. Litwin, V., K. Nagashima, A. M. Ryder, C. H. Chang, J. M. Carver, W. C. Olson, M. Alizon, K. W. Hasel, P. J. Maddon and G. P. Allaway. 1996. Human immunodeficiency virus type 1 membrane fusion mediated by a laboratory-adapted strain and a primary isolate analyzed by resonance energy transfer. J. Virol. 70: 6437-6441.

39. Loetscher, P., J. H. Gong, B. Dewald, M. Baggiolini and I. Clark-Lewis. 1998. N-terminal peptides of stromal cell derived factor-1 with CXC chemokine receptor 4 agonist and antagonist activities. J. Biol. Chem. 273: 22279-22283.

40. Mack, M., B. Luckow, P. J. Nelson, J. Cihak, G. Simmons, P. R. Clapham, N. Signoret, M. Marsh, M. Stangassinger, F. Borlat, T. N. C. Wells, D. Schlondorff and A. E. I. Proudfoot. 1998. Aminooxypentane- 40. RANTES induces CCR5 internalization but inhibits recycling: a novel inhibitory mechanisms of HIV infectivity. J. Ex. Med. 187: 1215-1224.
41. Maddon, P. J., A. G. Dalgleish, J. S. McDougal, P. R. Clapham, R. A. Weiss and R. Axel. 1986. The T4 gene encodes the AIDS virus receptor and is expressed in the immune system and the brain. Cell 47: 333-348.
42. McDougal, J. S., M. S. Kennedy, J. M. Sligh, S. P. Cort, A. Mawle and J. K. A. Nicholson. 1986. Binding of HTLVIII/LAV to T4$^+$ T cells by a complex of the 110K viral protein and the T4 molecule. Science 231: 382-385.
43. McKnight, A., D. Wilkinson, G. Simmons, S. Talbot, L. Picard, M. Ahuja, M. Marsh, J. A. Hoxie and P. R. Clapham. 1997. Inhibition of human immunodeficiency virus fusion by a monoclonal antibody to a co-receptor (CXCR4) is both cell type and virus strain dependent. J. Virol. 71: 1692-1696.
44. Merrill, D. P., D. J. Manion, T. C. Chou and M. S. Hirsch. 1997. Antagonism between human immunodeficiency virus type 1 protease inhibitors indinavir and saquinavir in vitro. J Infect Dis 176: 265-268.
45. Moore, J. P., Y. Cao, L. Qing, Q. J. Sattentau, J. Pyati, R. Koduri, J. Robinson, C. F. Barbas, D. R. Burton and D. D. Ho. 1995. Primary isolates of human immunodeficiency virus type 1 are relatively resistant to neutralization by monoclonal antibodies to gp120 and their neutralization is not predicted by studies with monomeric gp120. J. Virol. 69: 101-109.
46. Moore, J. P., B. A. Jameson, R. A. Weiss and Q. J. Sattentau.The HIV-cell fusion reaction. Boca Raton: CRC Press Inc., 1993 (J. Bentz, ed. Viral Fusion Mechanisms)
47. Moore, J. P., J. A. McKeating, Y. Huang, A. Ashkenazi and D. D. Ho. 1992. Virions of primary human immunodeficiency virus type 1 isolates resistant to soluble CD4 (sCD4) neutralization differ in sCD4 binding and glycoprotein gp120 retention from sCD4-sensitive isolates. J. Virol. 66: 235-243.
48. Moore, J. P. and R. W. Sweet. 1993. The HIV gp120-CD4 interaction: a target for pharmacological and immunological intervention. Prospect in Drug Discovery and Design 1: 235-250.
49. Murakami, T., T. Nakajima, Y. Koyanagi, K. Tachibana, N. Fujii, H. Tamamura, N. Yoshida, M. Waki, A. Matsumoto, O. Yoshie, T. Kishimoto, N. Yamamoto and T. Nagasawa. 1997. A small molecule CXCR4 inhibitor that blocks T cell line-tropic HIV-1 infection. J. Ex. Med. 186: 1389-1393.
50. Olson, W. C. unpublished results.
51. Pantaleo, G., C. Poli, L. Butini, C. Fox, A. I. Dayton and A. S. Fauci. 1991. Dissociation between syncytia formation and HIV spreading. Suppression of syncytia does not necessarily reflect inhibition of HIV infection. Eur. J. Immunol. 21: 1771-1774.
52. Rabut, G. E. E., J. A. Konner, F. Kajumo, J. P. Moore and T. Dragic. 1998. Alanine substitutions of polar and nonpolar residues in the amino-terminal domain of CCR5 differently impair entry of macrophage- and dual-tropic isolates of the human immunodeficiency virus type 1. J. Virol. 72: 3464-3468.
53. Rizzuto, C., R. Wyatt, N. Hernandez-Ramos, Y. Sun, P. Kwong, W. Hendrickson and J. Sodroski. 1998. Identification of a conserved human immunodeficiency virus gp120 glycoprotein structure important for chemokine receptor binding. Science 280: 1949-1953.
54. Rucker, J., M. Samson, B. J. Doranz, F. Libert, J. F. Berson, Y. Yi, R. J. Smyth, R. G. Collman, C. C. Broder, G. Vassart, R. W. Doms and M. Parmentier. 1996. Regions in the β-chemokine receptors CCR-5 and CCR-2b that determine HIV-1 cofactor specificity. Cell 87: 437-446.
55. Schols, D., S. Struyf, J. V. Damme, J. A. Este, G. Henson and E. D. Clercq. 1997. Inhibition of T-tropic HIV strains by selective antagonization of the chemokine receptor CXCR4. J. Ex. Med. 186: 138-356.
56. Simmons, G., P. R. Clapham, L. Picard, R. E. Offord, M. M. Rosenkilde, T. W. Schwartz, R. Buser, T. N. C. Wells and A. E. I. Proudfoot. 1997. Potent inhibition of HIV-1 infectivity in macrophages and lymphocytes by a novel CCR5 antagonist. Science 276: 276-279.
57. Simmons, G., D. Wilkinson, J. D. Reeves, M. T. Dittmar, S. Beddows, J. Weber, G. Carnegie, U. Desselberger, P. W. Gray, R. A. Weiss and P. R. Clapham. 1996. Primary, syncytium-inducing human immunodeficiency virus type-1 isolates are dual-tropic and most can use either LESTR or CCR5 as co-receptor for virus entry. J. Virol. 70: 8355-8360.
58. Strizki, J. M., J. Davis-Turner, R. G. Collman, J. Hoxie and F. Gonzalez-Scarano. 1997. A monoclonal antibody (12G5) directed against CXCR4 inhibits infection with the dual-tropic human immunodeficiency virus type 1 isolate HIV-1 89.6 but not the T-tropic isolate HIV-1 HxB. J. Virol. 71: 5678-5683.
59. Trkola, A., T. Dragic, J. Arthos, J. Binley, W. C. Olson, G. P. Allaway, C. Cheng-Mayer, J. Robinson, P. J. Maddon and J. P. Moore. 1996. CD4-dependent, antibody sensitive interactions between HIV-1 and its co-receptor CCR-5. Nature 384: 184-187.
60. Trkola, A., W. A. Paxton, S. P. Monard, J. A. Hoxie, M. A. Siani, D. A. Thompson, L. Wu, C. R. Mackay, R. Horuk and J. P. Moore. 1997. Genetic subtype-independent inhibition of human immunodeficiency virus type-1 replication by CC- and CXC chemokines. J. Virol. 72: 396-404.
61. Vijh-Warrier, S., A. Pinter, W. J. Honnen and S. A. Tilley. 1996. Synergistic neutralization of human immunodeficiency virus type 1 by a chimpanzee monoclonal antibody against the V2 domain of gp120 in combination with monoclonal antibodies against the V3 loop and the CD4-binding site. J. Virol. 70: 4466-4473.
62. Ward, S. G., K. bacon and J. Westwick. 1998. Chemokines and lymphocytes: more than an attraction. Immunity 9: 1-11.
63. Wu, L., N. P. Gerard, R. Wyatt, H. Choe, C. Parolin, N. Ruffing, A. Borsetti, A. A. Cardoso, E. Desjardin, W. Newman, C. Gerard and J. Sodroski. 1996. CD4-induced interaction of primary HIV-1 gp120 glycoproteins with the chemokine receptor CCR-5. Nature 384: 179-183.
64. Wu, L., G. LaRosa, N. Kassam, C. J. Gordon, H. Heath, N. Ruffing, H. Chen, J. Humblias, M. Samson, M. Parmentier, J. P. Moore and C. R. Mackay. 1997. Interaction of chemokine receptor CCR5 with its ligands: multiple domains for HIV-1 gp120 binding and a single domain for chemokine binding. J. Exp. Med. 186: 1373-1381.
65. Wyatt, R., P. D. Kwong, E. Desjardins, R. Sweet, J. Robinson, W. Hendrickson and J. Sodroski. 1998. The antigenic structure of the human immunodeficiency virus gp120 envelope glycoprotein. Nature 393: 705-711.
66. Wyatt, R. and J. Sodroski. 1998. The HIV-1 envelope glycoproteins: fusogens, antigens and immunogens. Science 280: 1884-1888.
67. Ylisastigui, L., J. J. Vizzavona, E. Drakopoulou, P. Paindavoine, C. F. Calvo, M. Parmentier, J. C. Gluckman, C. Vita and A. Benjouad. 1998. Synthetic full length and truncated RANTES inhibit HIV-1 infection of primary macrophages. AIDS 12: 977-984.

68. Zhang, J. L., H. Choe, B. J. Dezube, M. Farzan, P. L. Sharma, X. C. Zhou, L. B. Chen, M. Ono, S. Gillies, Y. Wu, J. G. Sodroski and C. S. Crumpacker. 1998. The bis-azo compound FP-21399 inhibits HIV-1 replication by preventing viral entry. Virology 244: 530-541.
69. Cairns, J. S., D'Souza. M. P., 1998. Chemokines and HIV-1 second receptors: the therapeutic connection. Nature Medicine. 1998. Vol 4, No. 5: 563.
70. Kilby, J.Michael, et al. 1998. Potent suppression of HIV-1 replication in humans by T-20, a peptide inhibitor of gp41-medicated virus entry. Nature Medicine. Vol. 3, No. 11: 1302.
71. U.S. Pat. No. 4,816,567, issued Mar. 28, 1989 to Cabilly et al.
72. U.S. Pat. No. 5,225,539, issued Jul. 6, 1993 to Gregory Winter.
73. U.S. Pat. No. 5,585,089, issued Dec. 17, 1996 to Queen et al.
74. U.S. Pat. No. 5,693,761, issued Dec. 2, 1997 to Queen et al.
75. PCT International Application No. PCT/US89/05857, filed Dec. 28, 1989, published Jul. 26, 1990, WO 90/07861.

SECOND SERIES OF EXPERIMENTS

Infection of cells by human immunodeficiency virus type 1 (HIV-1) is mediated by the viral envelope (env) glycoproteins gp120 and gp41, which are expressed as a noncovalent, oligomeric complex on the surface of virus and virally infected cells. HIV-1 entry into target cells proceeds at the cell surface through a cascade of events that include (1) binding of the viral surface glycoprotein gp120 to cell surface CD4, which is the primary receptor for HIV-1, (2) env binding to fusion coreceptors such as CCR5 and CXCR4, and (3) multiple conformational changes in gp41. During fusion, gp41 adopts transient conformations that include a prehairpin fusion intermediate that ultimately folds into a conformation capable of mediating fusion. These events culminate in fusion of the viral and cellular membranes and the subsequent introduction of the viral genome into the target cell. A similar sequence of molecular events is required for infection to spread via fusion of infected and uninfected cells. Each stage of the viral entry process can be targeted for therapeutic intervention.

HIV-1 attachment can be inhibited both by agents that bind the viral envelope glycoproteins and by agents that bind human CD4. Notably, HIV-1 attachment can be inhibited by compounds that incorporate the gp120-binding domains of human CD4 and molecular mimics thereof [1-7]. Because this interaction between gp120 and CD4 is essential for virus infection, CD4-based molecules have the potential to target most if not all strains of HIV-1. In addition, viruses have limited ability to develop resistance to such molecules.

The determinants for gp120 binding map to the first extracellular domain (D1) on CD4 [1], and the amino acids critical for binding center on a loop comprising amino acids 36-47. Potent HIV-1 inhibitory activity has been reproduced in a 27-amino acid peptide that mimics this loop and surrounding structures [7].

A number of recombinant CD4-based molecules have been developed and tested for clinical activity in man. The first of these contained the four extracellular domains (D1-D4) of CD4 but lacked the transmembrane and intracellular regions. This molecule, termed soluble CD4 (sCD4), demonstrated excellent tolerability when administered to humans at doses ranging to 10 mg/kg [8,9]. Transient reductions in plasma levels of infectious HIV-1 were observed in certain patients treated with sCD4. The short half-life of sCD4 in humans (45 minutes following intravenous administration) was identified as one obstacle to using this agent for chronic therapy.

Second-generation CD4-based proteins were developed with increased serum half-life. These CD4-immunoglobulin fusion proteins comprised the D1D2 domains of CD4 genetically fused to the hinge CH2 and CH3 regions of human IgG molecules. These divalent proteins derive HIV-1 neutralizing capacity from their CD4 domains and Fc effector functions from the IgG molecule. A CD4-IgG1 fusion protein was shown to have excellent tolerability and improved pharmacokinetics in Phase I clinical testing [10]. The antiviral evaluations were inconclusive.

More recently, a third-generation tetravalent CD4-IgG2 fusion protein was developed that comprises the D1D2 domains of CD4 genetically fused to the heavy and light chain constant regions of human IgG2. This agent binds the HIV-1 envelope glycoprotein gp120 with nanomolar affinity [5] and may inhibit virus attachment both by receptor blockade and by detaching gp120 from the virion surface, thereby irreversibly inactivating the virus. In standard PBMC-based neutralization assays, CD4-IgG2 neutralized primary HIV-1 isolates derived from all major subtypes and outlier groups. The CD4-IgG2 concentrations required to achieve a 90% reduction in viral infectivity, the in vitro IC90, were approximately 15-20 µg/ml [11], concentrations that are readily achievable in vivo. CD4-IgG2 was similarly effective in neutralizing HIV-1 obtained directly from the plasma of seropositive donors in an ex vivo assay, indicating that this agent is active against the diverse viral quasispecies that are encountered clinically [12]. CD4-IgG2 also provided protection against infection by primary isolates in the hu-PBL-SCID mouse model of HIV-1 infection [13]. Recent analyses have demonstrated that CD4-IgG2's ability to neutralize primary viruses is independent of their coreceptor usage [14].

Compared with mono- or divalent CD4-based proteins, CD4-IgG2 has consistently demonstrated as much as 100-fold greater potency at inhibiting primary HIV-1 isolates [5,12,14,15]. The heightened potency may derive from CD4-IgG2's ability to bind virions with increased valency/avidity and its steric juxtaposition of two gp120 binding sites on each Fab-like arm of the immunoglobulin molecule. The larger Fab-like arms of CD4-IgG2 are also more likely to span HIV-1 envelope spikes on the virion. In a variety of preclinical models, CD4-IgG2's anti-HIV-1 activity has been shown to compare favorably with those of the rare human monoclonal antibodies that broadly and potently neutralize primary HIV-1 isolates [5,11,14,15]. In addition, CD4-IgG2 therapy is in principle less susceptible to the development of drug-resistant viruses than therapies employing anti-env monoclonal antibodies or portions of the highly mutable HIV-1 envelope glycoproteins. These properties suggest that CD4-IgG2 may have clinical utility as an agent that neutralizes cell-free virus before it has the opportunity to establish new rounds of infection. In addition to treatment, CD4-IgG2 may have utility in preventing infection resulting from occupational, perinatal or other exposure to HIV-1.

In Phase I clinical testing, single-dose CD4-IgG2 demonstrated excellent pharmacology and tolerability. In addition, measurable antiviral activity was observed by each of two measures. First, a statistically significant acute reduction in plasma HIV RNA was observed following administration of a single 10 mg/kg dose. In addition, sustained reductions in plasma levels of infectious HIV were observed in each of two patients tested. Taken together, these observations indicate that CD4-IgG2 possesses antiviral activity in humans [16].

In addition to CD4-based proteins and molecular mimics thereof, HIV-1 attachment can also be inhibited by antibodies and nonpeptidyl molecules. Known inhibitors include (1) anti-env antibodies such as IgG1b12 and F105 [17,18], (2) anti-CD4 antibodies such as OKT4A, Leu 3a, and humanized versions thereof [19,20], and (3) nonpeptidyl agents that target either gp120 or CD4 [21], [22-24]. The latter group of compounds includes aurintricarboxylic acids, polyhydroxycarboxylates, sulfonic acid polymers, and dextran sulfates.

Several agents have been identified that block HIV-1 infection by targeting gp41 fusion intermediates. These -inhibitors may interact with the fusion intermediates and prevent them from folding into final fusogenic conformations. The first such agents to be identified comprised synthetic or recombinant peptides corresponding to portions of the gp41 ectodomain predicted to form hydrophobic alpha helices. One such region is present in both the amino and carboxy segments of the extracellular portion of gp41, and recent crystallographic evidence suggests that these regions interact in the presumed fusogenic conformation of gp41 [25,26]. HIV-1 infection can be inhibited by agents that bind to either N- or C-terminal gp41 epitopes that are exposed during fusion. These agents include the gp41-based peptides T-20 (formerly known as DP178), T-1249, DP107, N34, C28, and various fusion proteins and analogues thereof [27-33]. Other studies have identified inhibitors that comprise non-natural D-peptides and nonpeptidyl moieties [34, 35]. Clinical proof-of-concept for this class of inhibitors has been provided by T-20, which reduced plasma HIV RNA levels by as much as 2 logs in Phase I/II human clinical testing [36]. The broad antiviral activity demonstrated for this class of inhibitors reflects the high degree of gp41 sequence conservation amongst diverse strains of HIV-1.

Recent studies [37] have demonstrated the possibility of raising antibodies against HIV-1 fusion intermediates. This work employed "fusion-competent" HIV vaccine immunogens that capture transient fusion intermediates formed upon interaction of gp120/gp41 with CD4 and fusion coreceptors. The immunogens used in these studies were formalin-fixed cocultures of cells that express HIV-1 gp120/gp41 and cells that express human CD4 and CCR5 but not CXCR4. The antibodies elicited by the vaccines demonstrated unprecedented breadth and potency in inhibiting primary HIV-1 isolates regardless of their coreceptor usage, indicating that the antibodies were raised against structures such as gp41 fusion intermediates that are highly conserved and transiently exposed during HIV-1 entry. This class of antibodies does not include the anti-gp41 monoclonal antibody known as 2F5, which interacts with an epitope that is constitutively presented on virus particles prior to fusion [38].

Previously, synergistic inhibition of HIV-1 entry has been demonstrated using certain anti-env antibodies used in combination with other anti-env antibodies [39-44], anti-CD4 antibodies [45], or CD4-based proteins [6]. Similarly, synergies have been observed using anti-CCR5 antibodies used in combination with other anti-CCR5 antibodies, CC-chemokines, or CD4-based proteins [46]. Our prior studies described in U.S. application Ser. No. 09/493,346 examined combinations of fusion inhibitors and attachment inhibitors. Our prior studies described in PCT International Application No. PCT/US99/30345, WO 00/35409, published Jun. 22, 2000 examined combinations of HIV-1 attachment inhibitors and CCR5 coreceptor inhibitors. However, no prior studies have examined the combination of fusion inhibitors and CCR5 coreceptor inhibitors, nor the triple combination of fusion inhibitors, CCR5 coreceptor inhibitors and HIV-1 attachment inhibitors.

Experimental Details

A. Materials and Methods

Reagents

Purified recombinant CD4-IgG2 protein was produced by Progenics Pharmaceuticals, Inc. from plasmids CD4-IgG2-HC-pRcCMV and CD4-kLC-pRcCMV (ATCC Accession Nos. 75193 and 75194, respectively) as described [5]. HeLa-env cells were prepared by transfecting HeLa cells (ATCC Catalog # CCL-2) with HIV-1 gp120/gp41 env-expressing plasmid pMA243 as described [51]. PM1 cells are available from the National Institutes of Health AIDS Reagent Program (Catalog #3038). The T-20 peptide was synthesized using standard solid-phase Fmoc chemistry and purified and characterized as described [31,32].

Inhibition of HIV-1 env-mediated membrane fusion

HIV-1 envelope-mediated fusion between HeLa-Env$_{JR-FL}$ and PM1 cells was detected using a Resonance Energy Transfer (RET) assay. Equal numbers (2×104) of fluorescein octadecyl ester (F18)-labeled envelope-expressing cells and octadecyl rhodamine (R18)-labeled PM1 cells were plated in 96-well plates in 15% fetal calf serum in phosphate buffered saline and incubated for 4 h at 37 (C in the presence of varying concentrations of CD4-IgG2, T-20 or combinations thereof. Fluorescence RET was measured with a Cytofluor plate-reader (PerSeptive Biosystems) and % RET was determined as previously described [19].

Quantitative analysis of the synergistic, additive or antagonistic effects of combining the agents HIV-1 inhibition data were analyzed according to the Combination Index method of Chou and Talay [52,53]. The data are modeled according to the median-effect principle, which can be written $$f=1/[1+(K/c)^m] \quad (1)$$

where f is the fraction affected/inhibited, c is concentration, K is the concentration of agent required to produce the median effect, and m is an empirical coefficient describing the shape of the dose-response curve. Equation (1) is a generalized form of the equations describing Michaelis-Menton enzyme kinetics, Langmuir adsorption isotherms, and Henderson-Hasselbalch ionization equilibria, for which m=1 in all cases. In the present case, K is equal to the IC$_{50}$ value. K and m are determined by curve-fitting the dose-response curves.

After the best-fit parameters for K and m are obtained for the experimental agents and their combination, Equation (1) is rearranged to allow for calculation of c for a given f. The resulting table of values (e.g., FIG. 10) is used to calculate the Combination Index (CI) using the equation $$CI\ C_{1m}/C_1+C_{2m}/C_2+C_{2m}/C_1C_2 \quad (2)$$

where $C_1$=concentration of compound 1 when used alone $C_2$=concentration of compound 2 when used alone $C_{1m}$=concentration of compound 1 in the mixture $C_{2m}$=concentration of compound 2 in the mixture All concentrations are those required to achieve a given degree of inhibition. Equation (2) is used when the molecules are mutually nonexclusive, i.e., have different sites of action. Since this is the likely scenario for inhibitors of HIV-1 attachment and gp41 fusion intermediates, Equation (2) was used for all Combination Index calculations. Mutually nonexclusive calculations provide a more conservative estimate of the degree of synergy that mutually exclusive calculations, for which the $c_{1m}C_{2m}/c_1c_2$ term is dropped. CI<1 indicates synergy, CI=1 indicates purely additive effects, and CI>1 indicates antagonism. In general, CI values are most relevant at the higher levels of inhibition that are required to achieve a measurable clinical benefit.

Results and Discussion

Combinations of inhibitors of HIV-1 attachment and gp41 fusion intermediates were first tested for the ability to inhibit HIV-1 env-mediated membrane fusion in the RET assay. This assay has proven to be a highly successful model of the HIV-1 entry process. In this assay, env-dependent coreceptor usage patterns and cellular tropisms of the parental viruses are accurately reproduced [19]. Indeed, the assay was instrumental in demonstrating that CCR5 functions as a requisite fusion coreceptor and acts at the level of viral entry [54]. The fusion assay and infectious virus are similarly sensitive to inhibition by metal chelators and agents that target the full complement of viral and cellular receptors [19,46,55].

Dose-response curves were obtained for the agents used individually and in combination in both assays. Data were analyzed using the median effect principle [52,53]. The concentrations of single-agents or their mixtures required to produce a given effect were quantitatively compared in a term known as the Combination Index (CI). CI>1 indicates antagonism, CI=1 indicates a purely additive effect, and CI<1 indicates a synergistic effect wherein the presence of one agent enhances the effect of another.

Figure 8:
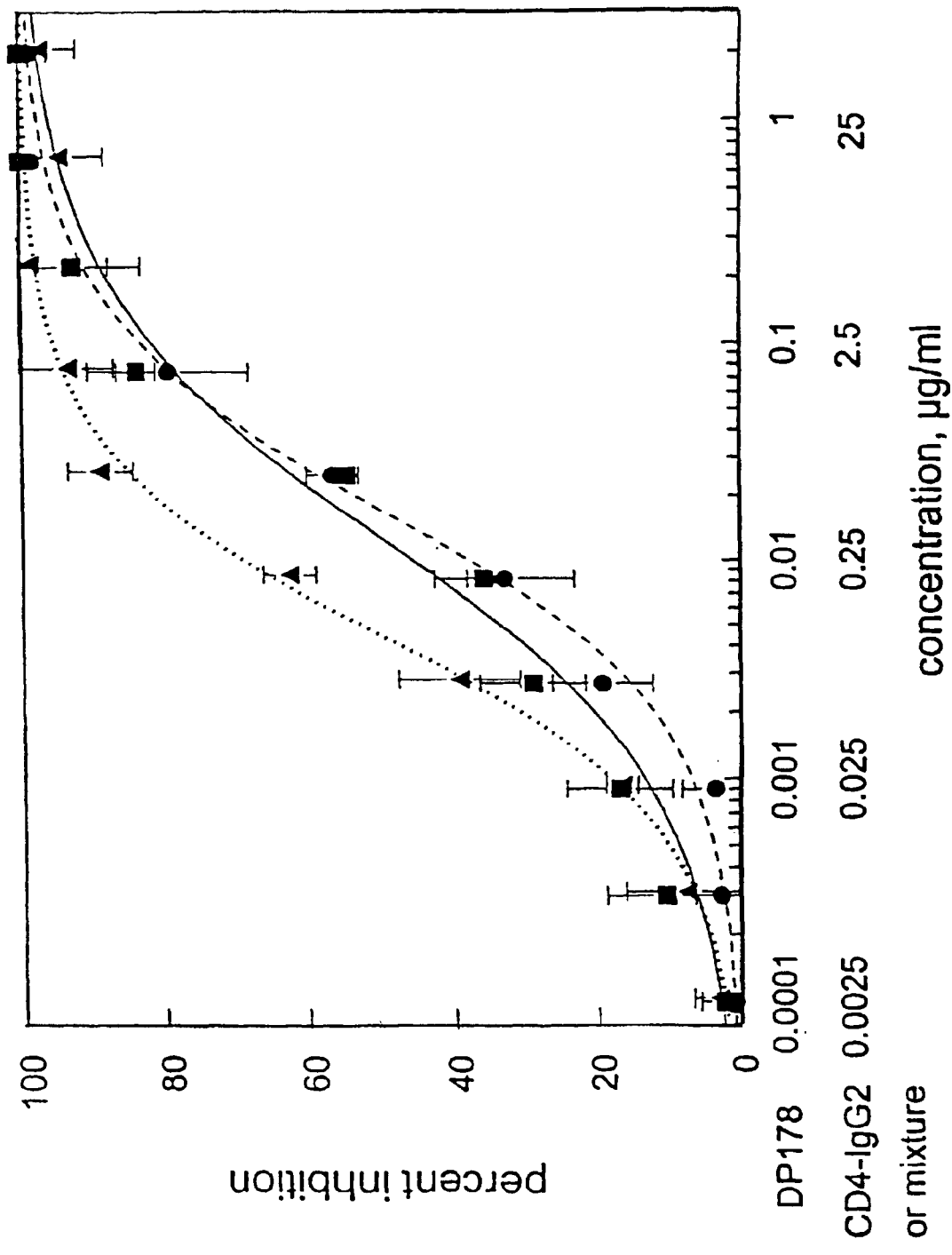

Combinations of CD4-IgG2 and T-20 were observed to be potently synergistic in inhibiting env-mediated membrane fusion. FIG. 8 illustrates representative dose-response curves obtained in the membrane fusion assay for CD4-IgG2, T-20, and combinations of the two. The curve for the combination is highly displaced towards lower inhibitor concentrations and provides qualitative evidence that CD4-IgG2 and T-20 act in a synergistic manner.

To quantitatively calculate the degree of synergy observed between CD4-IgG2 and T-20, we analyzed the dose-response curves according to the Combination Index method [52,53]. The analysis included data obtained at 25:1, 5:1, and 1:1 CD4-IgG2 :T-20 mass ratios. At the 25:1 mass ratio, both high (0-250 µg/ml CD4-IgG2 and 0-10 µg/ml T20) and low (0-50 µg/ml CD4-IgG2 and 0-2 µg/ml T-20) concentration ranges were evaluated. As indicated in FIG. 9, potent synergies were observed over these broad ranges of inhibitor ratios and concentrations, with CI values as low as 0.20 under optimal conditions. This degree of synergy is remarkable since CI values of 0.2 are rarely observed for combinations involving anti-HIV-1 antibodies [41-44], reverse transcriptase inhibitors [56], or protease inhibitors [57]. The observed synergies indicate that HIV-1 attachment and formation of gp41 fusion intermediates are inter-dependent steps. One possibility is that attachment inhibitors, when used at suboptimal concentrations, may slow but not abrogate the binding of gp120 to CD4. In this case, gp41 fusion intermediates may be formed and persist on the virus (or infected cell) for longer periods of time at levels below that required for membrane fusion and thus provide better targets for inhibitory agents.

The observed synergies translate into significant reductions in the amounts of CD4-IgG2 and T-20 needed for inhibition. These reductions are illustrated in FIG. 10 for CD4-IgG2 and T-20 used in a 25:1 mass ratio. By way of example, inhibition of viral entry by 95% requires 0.21 µg/ml of T-20 used alone, 19 µg/ml of CD4-IgG2 used alone and 1.14 µg/ml of a combination containing 0.044 µg/ml of T-20 and 1.1 µg/ml of CD4-IgG2. The combination reduces the respective doses of T-20 and CD4-IgG2 by 5- and 17-fold, respectively. Still greater dose reductions are observed at higher levels of inhibition.

THIRD SERIES OF EXPERIMENTS

HIV-1 entry proceeds via a cascade of at least three sequential events: (1) the attachment of the HIV-1 surface glycoprotein gp120 to CD4, which is the primary cellular receptor for HIV-1, (2) the interaction of the gp120-CD4 complex with fusogenic coreceptors such as CCR5 and CXCR4, and (3) membrane fusion mediated by the HIV-1 transmembrane glycoprotein gp41. PRO 542 (CD4-IgG2) is an antibody-like molecule that binds to gp120 and thereby inhibits attachment of the virus to host cells via CD4. PRO 140 (PA14) and PA12 are monoclonal antibodies to CCR5 that block its function as an HIV-1 coreceptor. Lastly, T-20 is a 36-mer peptide derived from the highly conserved C-terminal ectodomain of gp41. T-20 blocks gp41-mediated membrane fusion events. PRO 542 is thus an attachment inhibitor that blocks the first step of HIV-1 entry; PRO 140 and PA12 are both CCR5 coreceptor inhibitors that block the second step; and T-20 is a fusion inhibitor that blocks the third step. Attachment, coreceptor and fusion inhibitors are all members of a broad category of antiviral agents collectively know as HIV-1 entry inhibitors. CCR5 coreceptor inhibitors and CXCR4 coreceptor inhibitors constitute two distinct subclasses of coreceptor inhibitors.

When used individually, each of these compounds inhibit HIV-1 infection in vitro. PRO 542 and T-20 have also both demonstrated significant antiviral activity when used individually in human clinical trials, providing clinical proof-of-concept for inhibitors of HIV-1 entry (63,64).

The multi-step, inter-dependent nature of HIV-1 entry suggests that combinations of entry inhibitors may act in a non-additive or cooperative manner that either enhances (synergizes) or diminishes (antagonizes) the antiviral effect. Significant synergies have been observed for certain 2-way combinations of entry inhibitors, including attachment inhibitors used with CCR5 coreceptor inhibitors, attachment inhibitors used with fusion inhibitors, CCR5 coreceptor inhibitors used with other CCR5 coreceptor inhibitors, and CXCR4 coreceptor inhibitors used with fusion inhibitors (65,66).

However, whereas synergies are observed with certain members of a given class of inhibitor, purely additive or even antagonistic effects are seen when other members of the same class are used (65), highlighting the complexity of the HIV-1 entry process and the difficulty of predicting synergistic combinations. No prior study has examined either 2-way combinations of CCR5 coreceptor inhibitors and fusion inhibitors or triple or higher combinations that include members of all three classes of HIV-1 entry inhibitors. We have discovered that synergistic inhibition of HIV-1 can be obtained using the CCR5 coreceptor inhibitor PRO 140 in combination with the fusion inhibitor T-20. See FIG. 11D. In addition, remarkable synergies are observed using a triple combination containing an attachment inhibitor (PRO 542), a CCR5 coreceptor inhibitor (either PRO 140 or PA12) and a fusion inhibitor (T-20). See FIGS. 11A-C and FIG. 12. The synergies observed with the triple combination are surprisingly potent and translate into dose reductions ranging to 260-fold.

REFERENCES FOR SECOND AND THIRD SERIES OF EXPERIMENTS

1. Arthos J, Deen K C, Chaikin M A et al. Identification of the residues in human CD4 critical for the binding of HIV. Cell 1989; 57:469-481.

2. Clapham P R., Weber J N., Whitby D. et al. Soluble CD4 blocks the infectivity of diverse strains of HIV and SIV for T cells and monocytes but not for brain and muscle cells. Nature 1989; 337:368-370.
3. Deen K C., McDougal J S., Inacker R. et al. A soluble form of CD4 (T4) protein inhibits AIDS virus infection. Nature 1988; 331:82-84.
4. Capon D J, Chamow S M, Mordenti J et al. Designing CD4 immunoadhesins for AIDS therapy. Nature 1989; 337:525-531.
5. Allaway G P, Davis-Bruno K L, Beaudry G A et al. Expression and characterization of CD4-IgG2, a novel heterotetramer which neutralizes primary HIV-1 isolates. AIDS Research and Human Retroviruses 1995; 11:533-539.
6. Allaway G P, Ryder A M, Beaudry G A, Maddon P J. Synergistic inhibition of HIV-1 envelope-mediated cell fusion by CD4-based molecules in combination with antibodies to gp120 or gp41. AIDS Research & Human Retroviruses 1993; 9:581-587.
7. Vita C, Drakopoulou E, Vizzavona J et al. Rational engineering of a miniprotein that reproduces the core of the CD4 site interacting with HIV-1 envelope glycoprotein. Proc Natl Acad Sci U S A 1999; 96:13091-13096.
8. Schacker T., Coombs R W., Collier A C. et al. The effects of high-dose recombinant soluble CD4 on human immunodeficiency virus type 1 viremia. Journal of Infectious Diseases 1994; 169:37-40.
9. Schacker T, Collier A C, Coombs R et al. Phase I study of high-dose, intravenous rsCD4 in subjects with advanced HIV-1 infection. J Acquir Immune Defic Syndr Hum Retrovirol 1995; 9:145-152.
10. Collier A C, Coombs R W, Katzenstein D et al. Safety, pharmacokinetics, and antiviral response of CD4-immunoglobulin G by intravenous bolus in AIDS and AIDS-related complex. J Acquir Immune Defic Syndr Hum Retrovirol 1995; 10:150-156.
11. Trkola A., Pomales A P., Yuan H. et al. Cross-clade neutralization of primary isolates of human immunodeficiency virus type 1 by human monoclonal antibodies and tetrameric CD4-IgG2. Journal of Virology 1995; 69:6609-6617.
12. Gauduin M -C., Allaway G P., Maddon P J., Barbas CF3, Burton D R, Koup R A. Effective ex vivo neutralization of plasma HIV-1 by recombinant immunoglobulin molecules. Journal of Virology 1996; 70:2586-2592.
13. Gauduin M -C., Allaway G P, Olson W C, Weir R., Maddon P J, Koup R A. CD4-immunoglobulin G2 protects Hu-PBL-SCID mice against challenge by primary human immunodeficiency virus type 1 isolates. Journal of Virology 1998; 72:3475-3478.
14. Trkola A, Ketas T, KewalRamani V N et al. Neutralization sensitivity of human immunodeficiency virus type 1 primary isolates to antibodies and CD4-based reagents is independent of coreceptor usage. J Virol 1998; 72:1876-1885.
15. Fouts T R, Binley J M, Trkola A, Robinson J E, Moore J P. Neutralization of the human immunodeficiency virus type 1 primary isolate JR-FL by human monoclonal antibodies correlates with antibody binding to the oligomeric form of the envelope glycoprotein complex. Journal of Virology 1997; 71:2779-2785.
16. Jacobson J, Lowy I, Trkola A et al. Results of a Rhase I Trial of Single-Dose PRO 542, a Novel Inhibitor of HIV Entry. Abstracts of the 39th Interscience Conference on Antimicrobial Agents and Chemotherapy 1999; 14.
17. Burton D R, Pyati J, Koduri R et al. Efficient neutralization of primary isolates of HIV-1 by a recombinant human monoclonal antibody. Science 1994; 266:1024-1027.
18. Posner M R., Cavacini L A., Emes C L., Power J., Byrn R. Neutralization of HIV-1 by F105, a human monoclonal antibody to the CD4 binding site of gp120. Journal of Acquired Immune Deficiency Syndromes 1993; 6:7-14.
19. Litwin V, Nagashima K A, Ryder A M et al. Human immunodeficiency virus type 1 membrane fusion mediated by a laboratory-adapted strain and a primary isolate analyzed by resonance energy transfer. Journal of Virology 1996; 70:6437-6441.
20. Poignard P, Peng T, Sabbe R, Newman W. Mosier D E, Burton D R. Blocking of HIV-1 Co-receptor CCR5 in the hu-PBL-SCID Mouse Leads to a Co-receptor Switch. 6th Conference on Retroviruses and Opportunistic Infections 1999;
21. Cushman M, Wang P L, Chang S H et al. Preparation and anti-HIV activities of aurintricarboxylic acid fractions and analogues: direct correlation of antiviral potency with molecular weight. J Med Chem 1991; 34:329-337.
22. Mohan P, Schols D, Baba M, De Clercq E. Sulfonic acid polymers as a new class of human immunodeficiency virus inhibitors. Antiviral Res 1992; 18:139-150.
23. Schols D, Pauwels R, Desmyter J, De Clercq E. Dextran sulfate and other polyanionic anti-HIV compounds specifically interact with the viral gp120 glycoprotein expressed by T-cells persistently infected with HIV-1. Virology 1990; 175:556-561.
24. Schols D, Wutzler P, Klocking R, Helbig B, De Clercq E. Selective inhibitory activity of polyhydroxycarboxylates derived from phenolic compounds against human immunodeficiency virus replication. J Acquir Immune Defic Syndr 1991; 4:677-685.
25. Weissenhorn W, Dessen A, Harrison S C, Skehel J J, Wiley D C. Atomic structure of the ectodomain from HIV-1 gp41. Nature 1997; 387:426-430.
26. Chan D C, Fass D, Berger J M, Kim P S. Core Structure of gp41 from the HIV Envelope Glycoprotein. Cell 1997; 89:263-273.
27. Ji H, Shu W, Burling F T, Jiang S, Lu M. Inhibition of human immunodeficiency virus type 1 infectivity by the gp41 core: role of a conserved hydrophobic cavity in membrane fusion. Journal of Virology 1999; 73:8578-8586.
28. Jiang S, Lin K, Strick N, Neurath A R. HIV-1 inhibition by a peptide. Nature 1993; 365:113.
29. Wild C, Greenwell T, Matthews T. A synthetic peptide from HIV-1 gp41 is a potent inhibitor of virus-mediated cell-cell fusion. AIDS Res Hum Retroviruses 1993; 9:1051-1053.
30. Wild C, Greenwell T, Shugars D, Rimsky-Clarke L, Matthews T. The inhibitory activity of an HIV type 1 peptide correlates with its ability to interact with a leucine zipper structure. AIDS Res Hum Retroviruses 1995; 11:323-325.
31. Wild C, Oas T, McDanal C, Bolognesi D, Matthews T. A synthetic peptide inhibitor of human immunodeficiency virus replication: correlation between solution structure and viral inhibition. Proc Natl Acad Sci U S A 1992; 89:10537-10541.
32. Wild C T, Shugars D C, Greenwell T K, McDanal C B, Matthews T J. Peptides corresponding to a predictive alpha-helical domain of human immunodeficiency virus type 1 gp41 are potent inhibitors of virus infection. Proc Natl Acad Sci U S A 1994; 91:9770-9774.
33. Chan D C, Chutkowski C T, Kim P S. Evidence that a prominent cavity in the coiled coil of HIV type 1 gp41 is an attractive drug target. Proc Natl Acad Sci U S A 1998; 95:15613-15617.

34. Ferrer M, Kapoor T M, Strassmaier T et al. Selection of gp41-mediated HIV-1 cell entry inhibitors from biased combinatorial libraries of non-natural binding elements. Nat Struct Biol 1999; 6:953-960.
35. Eckert D M, Malashkevich V N, Hong L H, Carr P A, Kim P S. Inhibiting HIV-1 entry: discovery of D-peptide inhibitors that target the gp41 coiled-coil pocket. Cell 1999; 99:103-115.
36. Kilby J M, Hopkins S, Venetta T M et al. Potent suppression of HIV-1 replication in humans by T-20, a peptide inhibitor of gp41-mediated virus entry. Nat Med 1998; 4:1302-1307.
37. LaCasse R A, Follis K E, Trahey M, Scarborough J D, Littman D R, Nunberg J H. Fusion-competent vaccines: broad neutralization of primary isolates of HIV. Science 1999; 283:357-362.
38. Neurath A R, Strick N, Lin K, Jiang S. Multifaceted consequences of anti-gp41 monoclonal antibody 2F5 binding to HIV type 1 virions. AIDS Res Hum Retroviruses 1995; 11:687-696.
39. Thali M, Furman C, Wahren B et al. Cooperativity of neutralizing antibodies directed against the V3 and CD4 binding regions of the human immunodeficiency virus gp120 envelope glycoprotein. J Acquir Immune Defic Syndr 1992; 5:591-599.
40. Tilley S A, Honnen W J, Racho M E, Chou T C, Pinter A. Synergistic neutralization of HIV-1 by human monoclonal antibodies against the V3 loop and the CD4-binding site of gp120. AIDS Res Hum Retroviruses 1992; 8:461-467.
41. Laal S, Burda S, Gorny M K, Karwowska S, Buchbinder A, Zolla-Pazner S. Synergistic neutralization of human immunodeficiency virus type 1 by combinations of human monoclonal antibodies. Journal of Virology 1994; 68:4001-4008.
42. Vijh-Warrier S, Pinter A, Honnen W J, Tilley S A. Synergistic neutralization of human immunodeficiency virus type 1 by a chimpanzee monoclonal antibody against the V2 domain of gp120 in combination with monoclonal antibodies against the V3 loop and the CD4-binding site. Journal of Virology 1996; 70:4466-4473.
43. Li A, Baba T W, Sodroski J et al. Synergistic neutralization of a chimeric SIV/HIV type 1 virus with combinations of human anti-HIV type 1 envelope monoclonal antibodies or hyperimmune globulins. AIDS Res Hum Retroviruses 1997; 13:647-656.
44. Li A, Katinger H, Posner M R et al. Synergistic neutralization of simian-human immunodeficiency virus SHIV– vpu+ by triple and quadruple combinations of human monoclonal antibodies and high-titer anti-human immunodeficiency virus type 1 immunoglobulins. Journal of Virology 1998; 72:3235-3240.
45. Burkly L, Mulrey N, Blumenthal R, Dimitrov D S. Synergistic inhibition of human immunodeficiency virus type 1 envelope glycoprotein-mediated cell fusion and infection by an antibody to CD4 domain 2 in combination with anti-gp120 antibodies. Journal of Virology 1995; 69:4267-4273.
46. Olson W C, Rabut G E, Nagashima K A et al. Differential inhibition of human immunodeficiency virus type 1 fusion, gp120 binding, and CC-chemokine activity by monoclonal antibodies to CCR5. J Virol 1999; 73:4145-4155.
47. O'Brien W A., Koyanagi Y., Namazie A. et al. HIV-1 tropism for mononuclear phagocytes can be determined by regions of gp120 outside the CD4-binding domain. Nature 1990; 348:69-73.
48. Trkola A, Matthews J, Gordon C, Ketas T, Moore J P. A cell line-based neutralization assay for primary human immunodeficiency virus type 1 isolates that use either the CCR5 or the CXCR4 coreceptor. J Virol 1999; 73:8966-8974.
49. Fouts T R, Trkola A, Fung M S, Moore J P. Interactions of polyclonal and monoclonal anti-glycoprotein 120 antibodies with oligomeric glycoprotein 120-glycoprotein 41 complexes of a primary HIV type 1 isolate: relationship to neutralization. AIDS Res Hum Retroviruses 1998; 14:591-597.
50. Dreyer K, Kallas E G, Planelles V, Montefiori D, McDermott M P, Hasan M S. Primary isolate neutralization by HIV type 1-infected patient sera in the era of highly active antiretroviral therapy. AIDS Research and Human Retroviruses 1999; 15:1563-1571.
51. Allaway G P, Litwin V M, Maddon P J. Progenics Pharmaceuticals, Inc. Methods for using resonance energy transfer-based assay of HIV-1 envelope glycoprotein-mediated membrane fusion, and kits for practicing same. International Filing Date Jun. 7, 1996. International Patent Application No. PCT/US96/09894. 1996;
52. Chou TC. The median effect principle and the combination index for quantitation of synergism and antagonism. Synergism and Antagonism in Chemotherapy 1991; 61-102.
53. Chou T C, Talalay P. Quantitative analysis of dose-effect relationships: the combined effects of multiple drugs or enzyme inhibitors. Advances in Enzyme Regulation 1984; 22:27-55.
54. Dragic T., Litwin V., Allaway G P. et al. HIV-1 entry into CD4+ cells is mediated by the chemokine receptor CC-CKR-5. Nature 1996; 381:667.
55. Donzella G A, Schols D, Lin S W et al. AMD3100, a small molecule inhibitor of HIV-1 entry via the CXCR4 co-receptor. Nature Medicine 1998; 4:72-77.
56. Johnson V A, Merrill D P, Videler J A et al. Two-drug combinations of zidovudine, didanosine, and recombinant interferon-alpha A inhibit replication of zidovudine-resistant human immunodeficiency virus type 1 synergistically in vitro. Journal of Infectious Diseases 1991; 164:646-655.
57. Merrill D P, Manion D J, Chou T C, Hirsch M S. Antagonism between human immunodeficiency virus type 1 protease inhibitors indinavir and saquinavir in vitro. Journal of Infectious Diseases 1997; 176:265-268.
58. U.S. Pat. No. 4,816,567, issued Mar. 28, 1989 to Cabilly et al.
59. U.S. Pat. No. 5,225,539, issued Jul. 6, 1993 to Gregory Winter.
60. U.S. Pat. No. 5,585,089, issued Dec. 17, 1996 to Queen et al.
61. U.S. Pat. No. 5,693,761, issued Dec. 2, 1997 to Queen et al.
62. PCT International Application No. PCT/US89/05857, filed Dec. 28, 1989, published Jul. 26, 1990, WO 90/07861.
63. Jacobson, J. M. et al. Single-dose safety, pharmacology and antiviral activity of the human immunodeficiency virus (HIV) type 1 entry inhibitor PRO 542 in HIV-infected adults. J. Infect. Dis 182:326-329.
64. Kilby, J. M. et al. 1998 Potent suppression of HIV-1 replication in humans by T-20, a peptide inhibitor of gp-41 mediated virus entry. Nat. Med 4:1302-1307.
65. Olson. W. C. et al. 1999. Differential inhibition of human immunodeficiency virus type 1 fusion, gp120 binding, and CC-chemokine activity by monoclonal antibodies to CCR5. J. Virol 73:4145-4155.
66. Tremblay, C. et al. 2000. Strong in vitro synergy observed between the fusion inhibitor T-20 and a CxCR4 blocker AMD-3100. 7$^{th}$ Conference on Retroviruses and Opportunistic Infections, San Francisco.
67. Litwin, V. et al 1996, J. Virol 70:6437-6441.

FOURTH SERIES OF EXPERIMENTS

In vivo suppression of HIV-1 replication with PA14

CCR5 is a requisite fusion coreceptor for primary HIV-1 isolates and provides a promising target for therapy. PRO 140 (PA14) is an anti-CCR5 monoclonal antibody that potently inhibits HIV-1 entry at concentrations that do not affect CCR5's chemokine receptor activity. PRO 140 (PA14) mediates genetic subtype-independent inhibition of HIV-1 replication in primary T cells and macrophages in vitro (1). However, no published study to date has evaluated the in vivo antiviral activity of PRO 140 (PA14) or any other non-chemokine CCR5-targeting agent.

Methods: PRO 140 (PA14) was examined for activity in a therapeutic animal model of HIV-1 infection (2). SCID mice were reconstituted with normal human peripheral blood mononuclear cells and infected ~2 weeks later with HIV-1 $_{JR-CSF}$, a primary CCR5-using virus. When viral steady state was reached (~8-10 days post-infection), animals were treated intraperitoneally with a single 1 milligram dose of PRO 140 (PA14) or control antibody. Plasma viral loads were monitored pre- and post- injection by RT-PCR Amplicor Assay, which is an assay for measuring the amount of HIV RNA in a subject's plasma by reverse transcribing and thereby amplifying the HIV RNA prior to quantifying the RNA. The RNA may be quantified by hybridization with a labeled probe.

Figure 13:
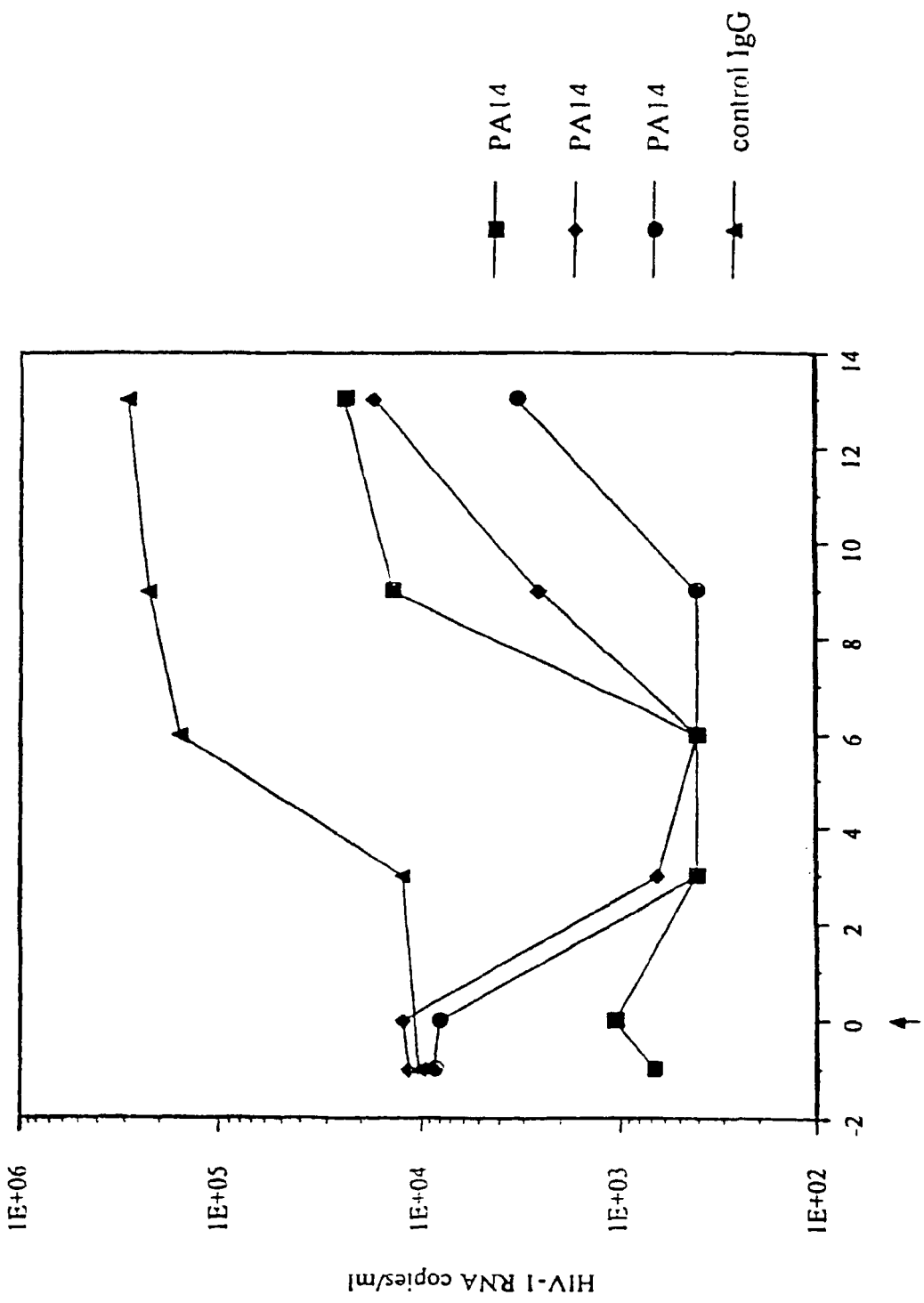

Results:

Viral loads decreased to undetectable levels (<400 copies/mL) in each of the PRO 140 (PA14)-treated animals (median decrease: 1.3 log$_{10}$; n=3) and remained undetectable for 6-9 days post-injection, whereas viral loads remained steady in control animals (FIG. 13).

Conclusions:

In these studies, single-dose PRO demonstrated potent antiviral activity in the hu-PBL-SCID mouse model of HIV infection. It is expected that not only multi-dose PRO 140 (PA14) but also PRO 140 (PA14) when used in combination with other HIV-1 entry inhibitors would inhibit HIV infection in humans.

The efficacy of the PA14 to inhibit HIV-1 infection in vivo in the hu-PBL-SCID may be contrasted with the lack of in vivo efficacy seen for other antibodies such as the anti-gp120 and anti-gp41 antibodies 2G12, b12 and 2F5, which have been demonstrated to inhibit HIV-1 infection in vitro (2).

REFERENCES FOR FOURTH SERIES OF EXPERIMENTS

1. Trkola et al. (2001) J. Virol. 75:579;
2. Poignard et al. (1999) Immunity 10:431-438.

What is claimed:

1. A method of reducing HIV-1 viral load in an HIV-1 infected subject which comprises administering to the subject solely post-infection an effective viral load-reducing amount of an agent which comprises a CDR domain of an anit-CCR5 antibody, which agent is monoclonal antibody PA14 (ATCC Accession No. HB-12610) or competes with PA14 for binding to an epitope on a human CCR5 chemokine receptor, so as to thereby reduce the subject's HIV-1 viral load to 50% or less of the subject's HIV-1 viral load prior to administration of any of the antibody to the subject.

2. The method of claim 1, wherein the subject's HIB-1 viral load is reduced to 33% or less of the subject's HIV-1 viral load prior to administration of any of the antibody to the subject.

3. The method of claim 1, wherein the subject's HIV-1 viral load is reduced to 10% or less of the subject's HIV-1 viral load prior to administration of any of the antibody to the subject.

4. The method of claim 1, wherein the reduction of the subject's HIV-1 viral load is sustained for at least one day.

5. The method of claim 4, wherein the reduction is sustained for at least three days.

6. The method of claim 5, wherein the reduction is sustained for at least seven days.

7. The method of claim 6, wherein the antibody is PA14 (ATCC Acession No. HB-12610).

8. The method of claim 6 or 7, wherein the effective amount of the antibody is between 0.1 mg and 100 mg per kg body weight of the subject.

9. The method of claim 8, wherein the effective amount of the antibody is between 1 and 50 mg per kg body weight of the subject.

10. The method of claim 9, wherein the effective amount of the antibody is between 2 mg and 40 mg per kg body weight of the subject.

11. The method of claim 10, wherein the effective amount of the antibody is between 3 and 30 mg per kg body weight of the subject.

12. The method of claim 11, wherein the effective amount of the antibody is between 4 and 20 mg per kg body weight of the subject.

13. The method of claim 12, wherein the effective amount of the antibody is between 5 and 10 mg per kg body weight of the subject.

14. The method of claim 6 or 7, wherein the antibody is administered at least once per day.

15. The method of claim 14, wherein the antibody is administered daily.

16. The method of claim 6 or 7, wherein the antibody is administered every other day.

17. The method of claim 6 or 7, wherein the antibody is administered every 6 to 8 days.

18. The method of claim 17, wherein the antibody is administered weekly.

19. The method of claim 6 or 7, wherein the antibody is administered intravenously, subcutaneously, intramuscularly, intraperitoneally, orally or topically.

20. The method of claim 6, wherein the subject is a human being and the antibody is a human antibody.

21. The method of claim 6, wherein the subject is a human being and the antibody is a humanized antibody.

22. The method of claim 6, wherein the antibody is a chimeric antibody.

23. The method of claim 1, further comprising administering at least one compound which binds to a gp41 subunit of HIV-1 envelope glycoprotein.

24. The method of claim 23, wherein the at least one compound is the T-20 inhibitor of HIV-1 entry.

* * * * *